(12) United States Patent
Yuan et al.

(10) Patent No.: US 11,191,843 B2
(45) Date of Patent: Dec. 7, 2021

(54) MULTI-ARM TARGETING ANTI-CANCER CONJUGATE

(71) Applicant: BrightGene Bio-Medical Technology Co., Ltd., Jiangsu (CN)

(72) Inventors: Jiandong Yuan, Jiangsu (CN); Yangqing Huang, Jiangsu (CN); Yunsong Song, Jiangsu (CN); Haifeng Ding, Jiangsu (CN)

(73) Assignee: BrightGene Bio-Medical Technology Co., Ltd., Jiangsu (CN)

( * ) Notice: Subject to any disclaimer, the term of this patent is extended or adjusted under 35 U.S.C. 154(b) by 100 days.

(21) Appl. No.: 16/498,765

(22) PCT Filed: Apr. 19, 2018

(86) PCT No.: PCT/CN2018/083746
§ 371 (c)(1),
(2) Date: Sep. 27, 2019

(87) PCT Pub. No.: WO2018/192550
PCT Pub. Date: Oct. 25, 2018

(65) Prior Publication Data
US 2021/0008218 A1   Jan. 14, 2021

(30) Foreign Application Priority Data

Apr. 21, 2017 (CN) .......................... 201710263113.4
Apr. 21, 2017 (CN) .......................... 201710263114.9
Apr. 21, 2017 (CN) .......................... 201710263126.1

(51) Int. Cl.
| | | |
|---|---|---|
| *A61K 47/64* | (2017.01) | |
| *A61K 47/60* | (2017.01) | |
| *A61K 47/65* | (2017.01) | |
| *A61P 35/00* | (2006.01) | |
| *A61K 31/4745* | (2006.01) | |

(52) U.S. Cl.
CPC .......... *A61K 47/60* (2017.08); *A61K 31/4745* (2013.01); *A61K 47/64* (2017.08); *A61K 47/65* (2017.08); *A61P 35/00* (2018.01)

(58) Field of Classification Search
None
See application file for complete search history.

(56) References Cited

FOREIGN PATENT DOCUMENTS

| | | |
|---|---|---|
| CN | 104784699 A | 7/2015 |
| CN | 104906076 A | 9/2015 |
| CN | 105396141 A | 3/2016 |
| CN | 107375288 A | 11/2017 |
| JP | 2010503708 | 2/2010 |
| JP | 2010511744 A | 4/2010 |
| JP | 2016531895 | 10/2016 |
| WO | 2005028539 A2 | 3/2005 |
| WO | WO 2008/066902 | 6/2008 |
| WO | 2011063156 A2 | 5/2011 |
| WO | 2015187540 A1 | 10/2015 |

OTHER PUBLICATIONS

Zhang et al., "Tuning Multiple Arms," Polym. Chem., 2015, 6:2192-2203.
Zhao et al., "Novel Prodrugs of SN38 Using Multiarm Poly(ethylene glycol) Linkers," Bioconjugate Chem., 2008, 19:849-859.
International Search Report for PCT/CN2018/083746, dated Jul. 2, 2018. 4 pages.

*Primary Examiner* — Thomas S Heard
(74) *Attorney, Agent, or Firm* — Fish & Richardson P.C.

(57) ABSTRACT

A multi-branched drug conjugate of formula (I) or a pharmaceutically acceptable salt thereof. In the formula, R is an organic center, POLY is a polymer, L is a multivalent linker, T is a targeting molecule, D is an active agent, and q is any integer between 3 and 8. The symbol "*" in L represents a junction point of the multivalent linker L and the targeting molecule T, "#" represents a junction point of the multivalent linker L and the active agent D, and "%" represents a junction point of the multivalent linker L and POLY. 1 is any integer between 2 and 20, and m and n are each an integer between 0 and 10. T is iRGD, cRGD, tLyp-1, Lyp-1, RPARPAR, Angiopep2, or GE11. D is a camptothecin drug.

18 Claims, 5 Drawing Sheets

MULTI-ARM TARGETING ANTI-CANCER CONJUGATE

TECHNICAL FIELD

The present disclosure relates to a targeted anticancer conjugate modified by a multi-arm polymer, more specifically, the present disclosure relates to attaching a targeting molecule to an anticancer drug via the multi-arm polymer to obtain a conjugate.

BACKGROUND

Over the years, numerous methods for improving the stability and delivery of biologically active agents have been proposed. Challenges associated with the formulation and delivery of a pharmaceutical agent may include poor water solubility, toxicity, low bioavailability, instability, and rapid in vivo degradation of the pharmaceutical agent. Although many approaches have been designed to improve the delivery of the pharmaceutical agent, there is no single approach without its disadvantages. For example, commonly adopted drug delivery methods aim at solving or at least improving one or more of the following problems including drug encapsulation in a liposome, polymer matrix, or monomolecular micelle; covalent attachment to a water-soluble polymer such as polyethylene glycol; use of a gene-targeting agent; structures of salts, and the like.

WO2005028539, WO2010019233, WO2011063156, and WO2011063158 disclose a drug in phase III clinical trials, nktr 102. The drug is mainly used for metastatic breast cancer, and is developed by Nektar Therapeutics. The drug is a water-soluble multi-branched polymeric prodrug aiming at increasing drug loading, and its structure is shown for example, at WO2011063158, p. 3.

This compound is attached to irinotecan using a multi-arm PEG, so as to improve water solubility, increase drug loading, and reduce side effects without changing anticancer effects. However, this drug still has disadvantages, for example, poor targeting property, inability to act on specific cancer cells, and affecting the functions of normal cells while killing cancer cells, thus making the incidence of adverse reactions still high.

SUMMARY

The present disclosure discloses a novel targeting multi-branched drug conjugate, the conjugate has three or more branches, and the conjugate may be represented as the following formula:

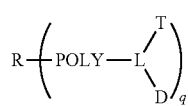

(I)

R is an organic core, POLY is a polymer, L is a multivalent linker, T is a targeting molecule, D is an active agent, and q is any integer between 3 and 8, wherein L is

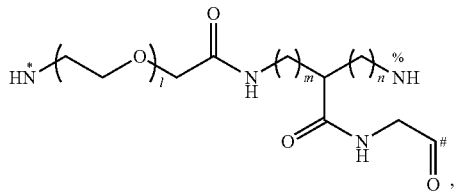

symbol "*" represents an attachment point of the multivalent linker L and the targeting molecule T, "#" represents an attachment point of the multivalent linker L and the active agent D, and "%" represents an attachment point of the multivalent linker L and POLY, wherein l is any integer between 2 and 20, and m and n are any integer between 0 and 10 respectively; D is a camptothecin-based drug as represented by formula (II):

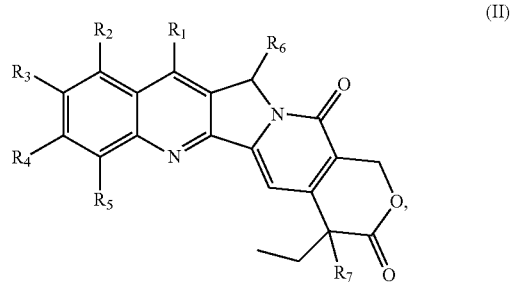

(II)

$R_1$ to $R_5$ are selected from the following groups independently from each other: hydrogen, halogen, acyl, alkyl, substituted alkyl, alkoxy, substituted alkoxy, alkenyl, alkynyl, cycloalkyl, hydroxyl, cyano, nitro, azido, amido, hydrazine, amine group, substituted amine group, hydroxycarbonyl, alkoxycarbonyl, alkoxycarbonyloxy, carbamoyloxy, arylsulfonyloxy, and alkylsulfonyloxy; $R_6$ is H or $OR_8$; $R_8$ is alkyl, alkenyl, cycloalkyl, halogenated alkyl, or hydroxyalkyl; and $R_7$ is hydroxyl, amino group, or thiol.

POLY is a polymer, L is a multivalent linker, T is a targeting molecule, D is an active agent, and these four components constitute a "branch" of this multi-branched drug conjugate together. Each branch and the other branches of this multi-branched drug conjugate are independent from each other. Each branch emanates from the organic core "R". However, in general, each branch of the conjugate is the same.

Each variable portion in structural formula (I) will now be described in detail.

Organic core, "R": In structural formula (I), "R" is an organic core radical of 1 to 100 atoms. Preferably, R comprises 3 to 50 atoms, and more preferably, R comprises about 3 to 30 atoms. R may be a core in which all the atoms are carbon atoms, and may also optionally contain one or more heteroatoms such as O, S, N and P, depending on the particular central molecule used. R may be linear, branched or cyclic, and emanate at least 3 independent polymeric branches. In structural formula (I), "q" corresponds to the number of polymeric branches emanating from "R".

The organic core "R" is derived from a molecule. The molecule provides many sites for the attachment of polymers, and the number of sites is approximately equal to the number of the polymeric branches. More preferably, the main central formula of the multi-branched polymer structure at least carries a residue of a polyhydroxy compound, a polysulfide compound or a polyamine compound with 3 or more hydroxy groups, thiol groups or amino groups, and the residue is suitable as the polymeric branch. A "polyhydroxy compound" is a molecule composed of multiple (more than 2) available hydroxy groups. A "polysulfide compound" is a molecule composed of multiple (more than 2) available thiol groups. A "polyamine compound" is a molecule composed of multiple (more than 2) available amine groups. Depending on the number of polymeric branches, the parent polyhydroxy compound, polyamine compound or polysulfide compound (prior to the covalent binding of POLY) typically comprises 3 to 25 hydroxy groups, thiol groups or amino groups, preferably 3 to 10 hydroxy groups, thiol groups or amino groups, and most preferably from 3 to about 8 (for example, 3, 4, 5, 6, 7, or 8) hydroxy groups, thiol groups or amino groups that are suitable for the covalent binding to POLY.

The parent of the polyhydroxy compound core or polyamine compound core typically has a structural formula of R—(OH)$_p$ or R—(NH$_2$)$_p$ prior to the interaction with polymers. In structural formula (I), the p value corresponds to the q value. This is because if the position of each of the functional groups (typically, —OH and —NH$_2$) in a parent organic molecule is susceptible or liable to reaction, the functional groups may be covalently bound to POLY of the polymeric branches. In structural formula (I), after being attached to POLY, each hydroxy group of the parent polyhydroxy compound of R has been converted to one polymeric branch, and R described herein is the residue after the attachment. For example, if the molecule of the organic core is derived from pentaerythritol, the parent polyhydroxy compound has a structural formula of C(CH$_2$OH)$_4$, and the organic core radical R is represented as

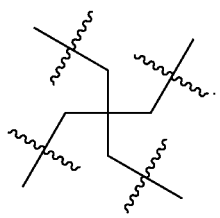 [SMILES: *CC(C*)(C*)C*]

Illustrative polyhydroxy compounds which are preferred as the cores of the polymers include aliphatic polyhydroxy compounds comprising 1 to 10 carbon atoms and 1 to 10 hydroxy groups such as ethylene glycol, alkanediol, hydrocarbyl glycol, alkylene hydrocarbyl glycol, hydrocarbyl cycloalkyl glycol, 1,5-decalindiol, 4,8-di(hydroxymethyl) tricyclodecane, cycloalkylene glycol, dihydroxyalkane, trihydroxyalkane and tetrahydroxyalkane. Cycloaliphatic polyhydroxy compounds include linear or closed-ring saccharides and sugar alcohols such as mannitol, sorbitol, inositol, xylitol, quebrachitol, threitol, arabitol, erythritol, hexanehexol, ribose, arabinose, xylose, lyxose, rhamnose, galactose, glucose, fructose, sorbose, mannose, pyranose, altrose, talose, tagatose, pyranoside, sucrose, lactose and maltose. Aromatic polyhydroxy compounds such as pyrocatechol, hydrocarbyl pyrocatechol, pyrogaelol, fluoroglycine phenol, 1,2,4-benzenetriol, resorcinol, hydrocarbyl resorcinol, dihydrocarbyl resorcinol, orcinol monohydrate, olivetol, hydroquinone, hydrocarbyl hydroquinone and phenyl hydroquinone may also be adopted. Other polyhydroxy compound cores that may be adopted include crown ethers, cyclodextrins, dextrins or other carbohydrates.

In structural formula (I), q corresponds to the number of polymeric branches attached to "R", and the specific number may be 3 to 20. Typically, the specific number of "q" is 3, 4, 5, 6, 7, or 8. Specifically, 3, 4, 5, 6, 7, or 8 polymeric branches emanate from "R" which is the core.

In certain specific embodiments, "R" has 3 polymeric branches, and "R" is preferably

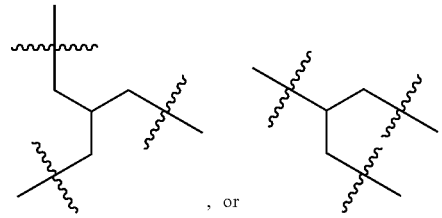

In certain specific embodiments, "R" has 4 polymeric branches, and "R" is preferably

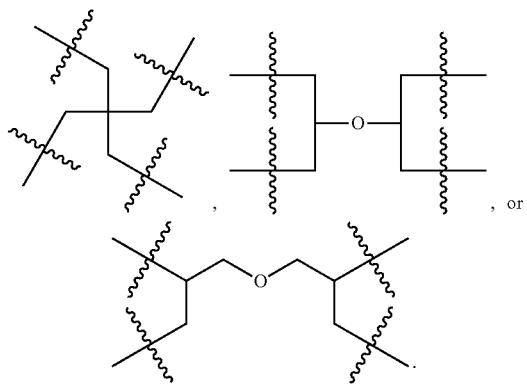

In certain specific embodiments, "R" has 6 polymeric branches, and "R" is preferably

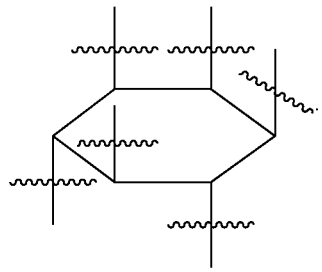

In certain specific embodiments, "R" has 8 polymeric branches, and "R" is preferably

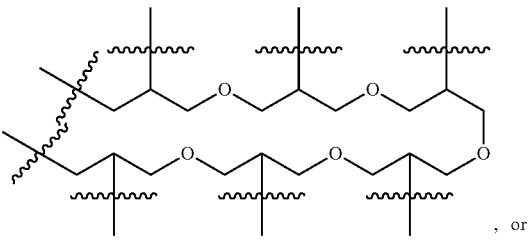

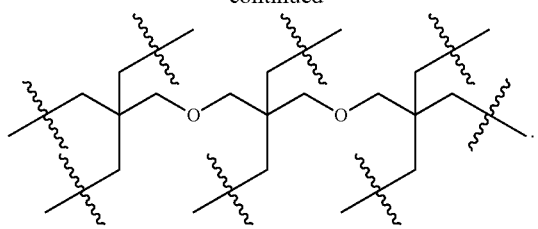

Polymer, "POLY": In structural formula (I), "POLY" is a polymer. POLY in each polymeric branch is selected independently, preferably each polymer is the same polymer, and more preferably each polymeric branch in structural formula (I) is the same. A preferred polymer is water-soluble, any water-soluble polymer may be used to form the conjugates of the present disclosure, and the polymers referred to in the present disclosure may be in any geometric configuration or form. Representative polymers include but are not limited to: polyethylene glycol, polypropylene glycol, poly(vinyl pyrrolidone), poly(hydroxyalkyl methyl acrylamide), poly(hydroxyalkyl methacrylate), poly(saccharide), poly(α-hydroxy acid), poly(acrylic acid), poly(vinyl acetate), polyphosphazine, polyoxazoline, poly(N-acryloyl morpholine), and the like.

In a typical compound, "POLY" is polyethylene glycol (PEG), and may be in any geometric configuration or form, including linear, branched, forked chains, and the like. "Polyethylene glycol" used herein means to encompass any water-soluble poly(ethylene oxide). Typically, PEG used in the present disclosure will comprise one of the following two structures: "$(CH_2CH_2O)_k$—" or "$(CH_2CH_2O)_k$—$CH_2CH_2$—", depending on whether one or more terminal oxygens have been, for example, replaced during synthesis and transformation. The variable k ranges from 5 to about 500, and the structures of these terminal groups as well as the overall PEG may vary. The structure of said polyethylene glycol usually further comprises a portion of terminal residue, which is similar to the terminal group of POLY, and may be ended with H, $NH_2$, OH, $CO_2H$, $C_{1-6}$ alkyl (for example, methyl, ethyl, or propyl), $C_{1-6}$ alkoxy (for example, methoxy or ethoxy), acyl, or aryl.

The preferred "POLY" of the present disclosure is a linear polyethylene glycol, and the typical structure is

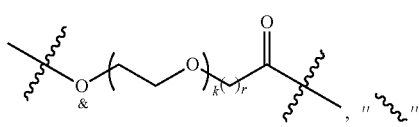

represents a site for attachment of atoms, and the oxygen atom marked with "&" is the atom attached to the organic core "R", wherein the value of k ranges from about 5 to 500, most preferably, from 50 to 200, and r is any integer between 1 and 10. More preferably, "POLY" of the present disclosure is

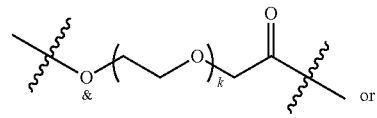

or

POLY of the present disclosure may also be:

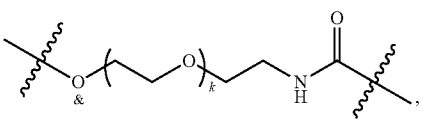

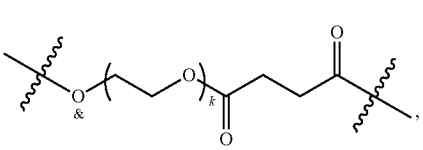

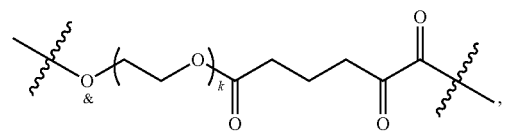

or the like.

The active agent "D" referred to in the present disclosure is a camptothecin-based anticancer agent, and the camptothecin-based drugs are topoisomerase I inhibitors for clinical use. While having high activity, the camptothecin-based drugs have disadvantages such as poor water solubility and great toxic and side effects on normal body tissues, which greatly limit the clinical application of the camptothecin-based anticancer agents.

$R_7$ in the structure of D is the group covalently attached to the multivalent linker L, such as hydroxyl, amino group, or thiol, preferably, hydroxyl. When the active agent D is attached to the multivalent linker L, there should be no significant loss of biological activity.

The active agent of the present disclosure is preferably irinotecan, SN-38, 10-hydroxycamptothecin, or rubitecan. Among them,

| irinotecan | SN-38 |
|---|---|
| structural formula | |

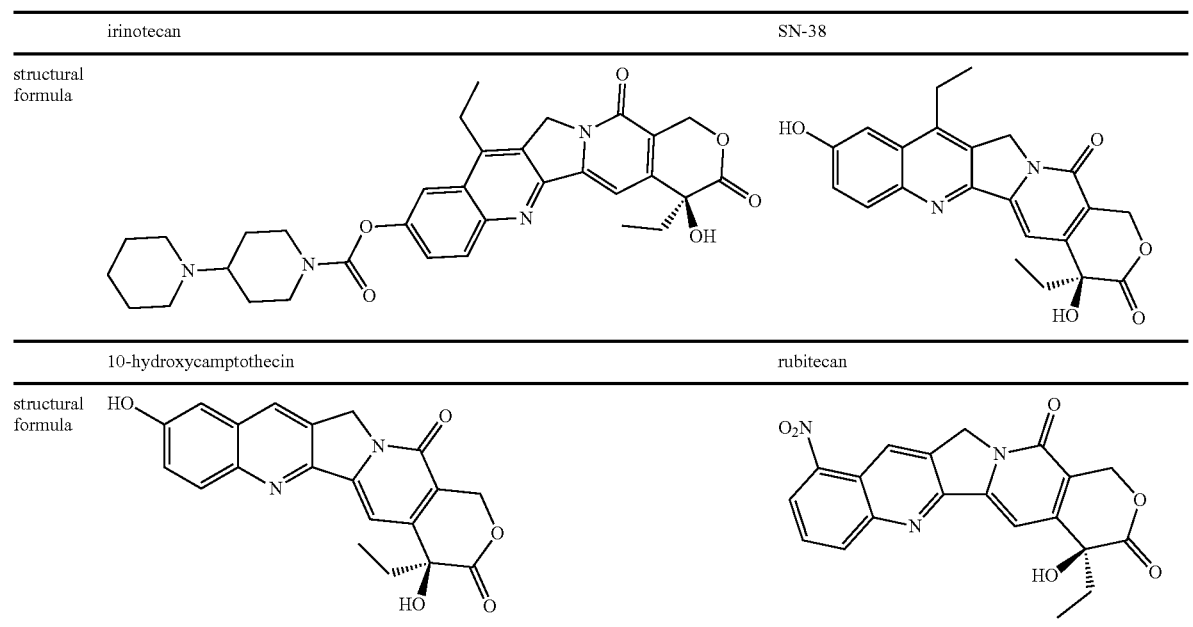

| 10-hydroxycamptothecin | rubitecan |
|---|---|
| structural formula | |

In the present disclosure, "T" is a targeting molecule with or without pharmaceutical effect. The effect of this targeting molecule is to increase the targeting property, such that the concentration of the conjugate in a target tissue is higher and the physiological activity or pharmaceutical effect is enhanced. "T" may be a monofunctional targeting molecule, and may also be a multifunctional targeting molecule. In some alternative embodiments, "T" may also be a targeting moiety composed of two or more targeting molecules. In certain specific embodiments, "T" may be an RGD peptide containing a sequence of "arginine-glycine-aspartic acid", and the RGD peptide is the recognition site of the interaction between integrin and its ligand protein. A preferred RGD peptide includes iRGD, cRGD, and the like. T may also be Lyp-1, Lyp-1, RPARPAR, Angiopep2, or GE11.

The structure of iRGD is as follows:

cRGD is a series of compounds, and the typical compounds include:

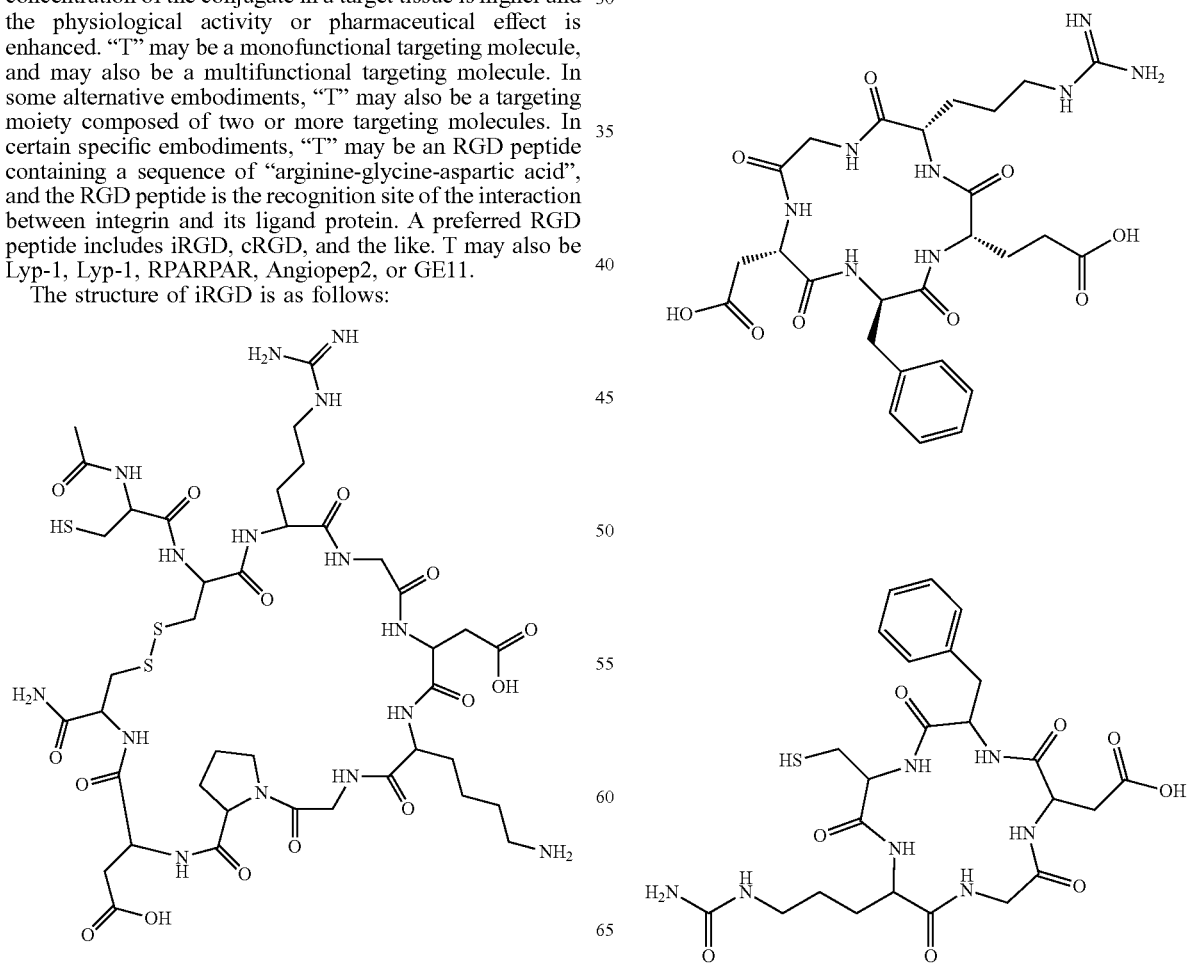

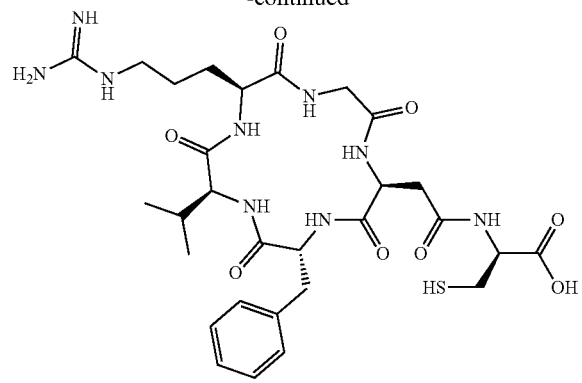
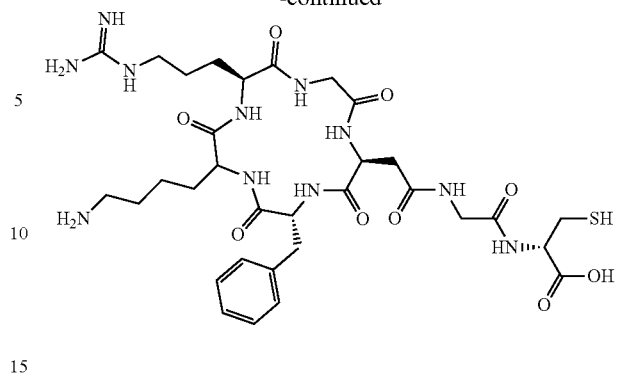
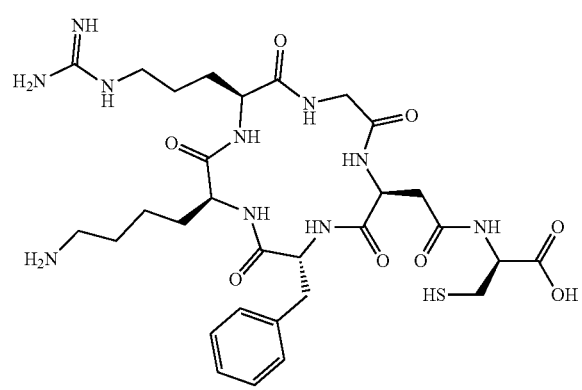
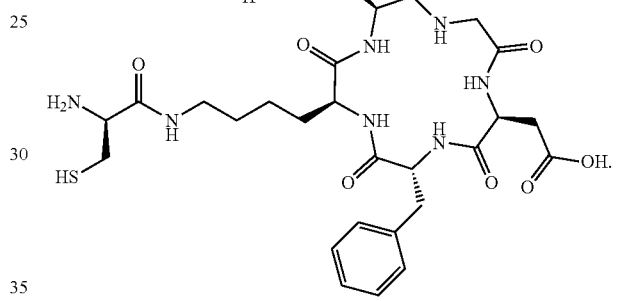
The preferred cRGD is
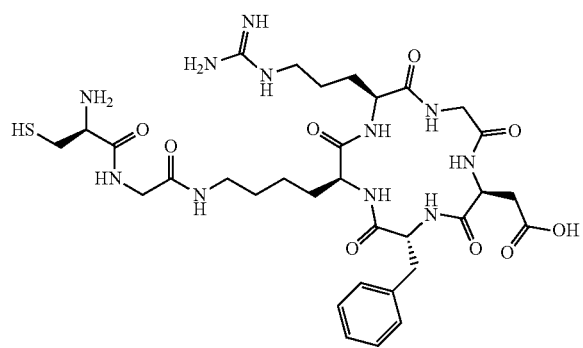
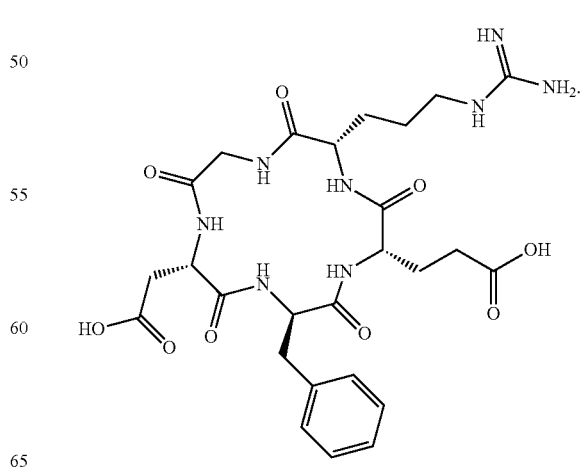

The structure of tLyp-1 is as follows:
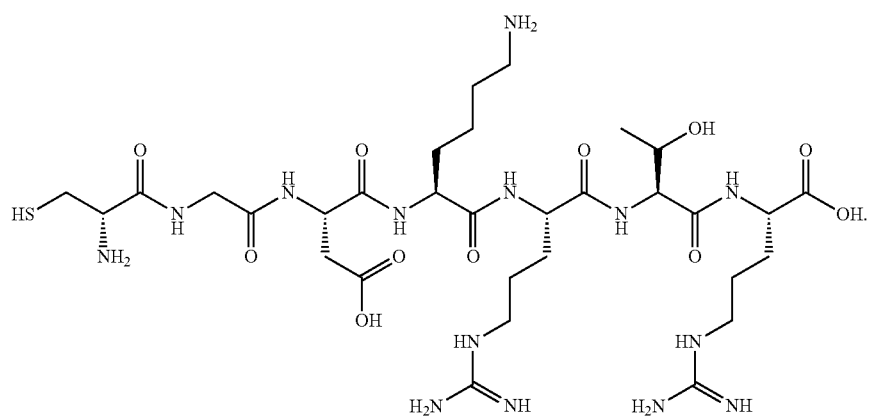 [SMILES: CC(O)[C@H](NC(=O)[C@H](CCCNC(=N)N)NC(=O)[C@H](CCCCN)NC(=O)[C@H](CC(=O)O)NC(=O)CNC(=O)[C@H](N)CS)C(=O)N[C@@H](CCCNC(=N)N)C(=O)O]
The structure of Lyp-1 is as follows:
The polypeptide sequence of RPARPAR is arginine-proline-alanine-arginine-proline-alanine-arginine, and its structure is as follows:
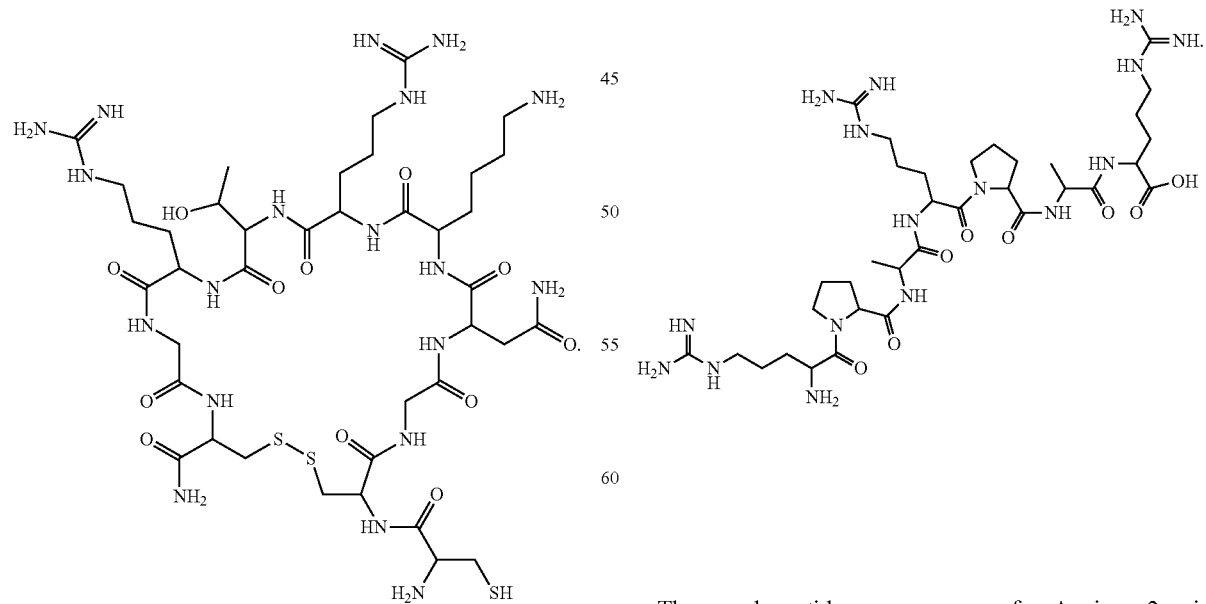
The polypeptide sequence of Angiopep2 is TFFYGGSRGKRNNFKTEEY, and its structure is as follows:

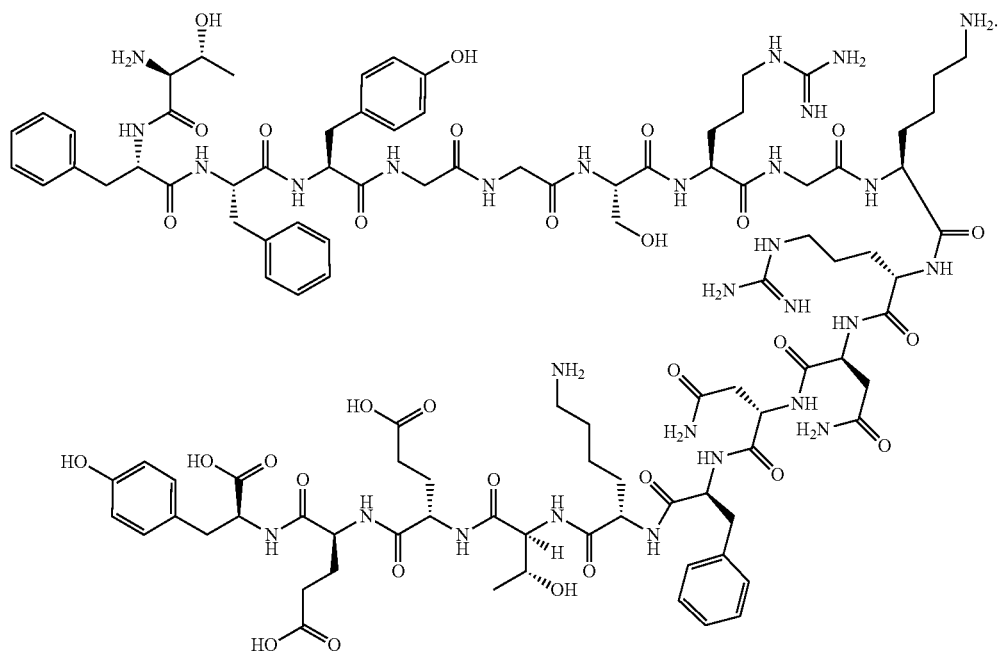 [SMILES: C[C@@H](O)[C@H](N)C(=O)N[C@@H](Cc1ccccc1)C(=O)N[C@@H](Cc1ccccc1)C(=O)N[C@@H](Cc1ccc(O)cc1)C(=O)NCC(=O)NCC(=O)N[C@@H](CO)C(=O)N[C@@H](CCCNC(=N)N)C(=O)NCC(=O)N[C@@H](CCCCN)C(=O)N[C@@H](CCCNC(=N)N)C(=O)N[C@@H](CC(N)=O)C(=O)N[C@@H](CC(N)=O)C(=O)N[C@@H](Cc1ccccc1)C(=O)N[C@@H](CCCCN)C(=O)N[C@H](C(=O)N[C@@H](CCC(=O)O)C(=O)N[C@@H](CCC(=O)O)C(=O)N[C@@H](Cc1ccc(O)cc1)C(=O)O)[C@@H](C)O]

The polypeptide sequence of GE11 is YHWYGYTPQNVI, and its structure is

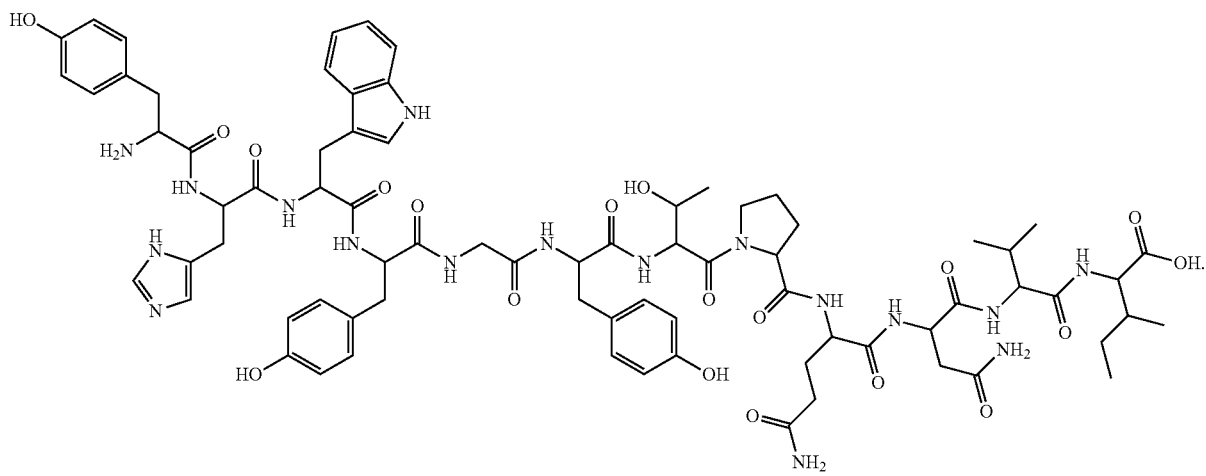 [SMILES: CCC(C)C(NC(=O)C(NC(=O)C(CC(N)=O)NC(=O)C(CCC(N)=O)NC(=O)C1CCCN1C(=O)C(NC(=O)C(Cc1ccc(O)cc1)NC(=O)CNC(=O)C(Cc1ccc(O)cc1)NC(=O)C(Cc1c[nH]c2ccccc12)NC(=O)C(Cc1cnc[nH]1)NC(=O)C(N)Cc1ccc(O)cc1)C(C)O)C(C)C)C(=O)O]

The active agent "D" referred to in the present disclosure refers to a part of an unmodified parent active agent, or a residue of the unmodified parent active agent prior to the formation of a covalent chain (or its activated or chemically modified form) by the covalent attachment of a drug to the multivalent linker of the present disclosure. When the linking group between the active agent moiety and the multivalent linker is hydrolyzed or digested, the active agent itself is released.

According to the purpose of the present disclosure, the term "residue" should be understood as a part of the compound, and it refers to the remainder after undergoing a substitution reaction with another compound.

When the conjugate of the present disclosure enters an organism and reaches a target cell or a target tissue, the active agent D is cleaved from the multivalent linker L. The active agent D is released in an unmodified form, i.e., a form in which no covalent bond is formed, and separated from the parent, so as to exert physiological activity.

In preferred embodiments of the present disclosure, "POLY" is a linear polyethylene glycol linking arm, that is, the conjugates of the present disclosure include the following types of compounds:

four-arm:

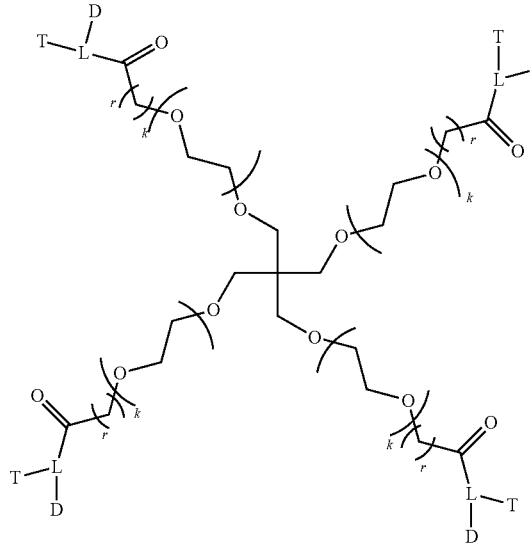
(III)

eight-arm:

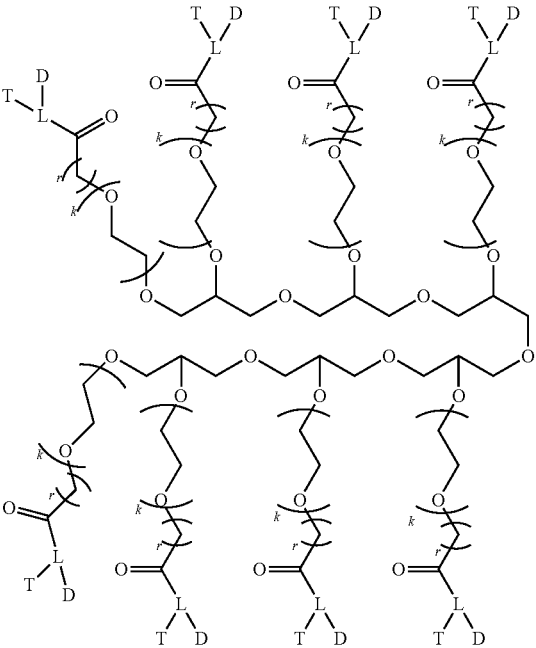
(V)

wherein the value of k ranges from about 5 to 500, most preferably, from 50 to 200, and r is any integer between 1 and 10.

The compound of formula (III) is preferred in the present disclosure, and on the basis of formula (III), k is preferably 113. It should be understood by those skilled in the art that in the field of polymers, k represents the degree of polymerization of the polymer, and it depends on the molecular weight of said polymer and is not an absolute numerical value. When the value of k is 113, it means that the mean value is 113.

In a more preferred embodiment, the targeting moiety "T" of the conjugate of the present disclosure is one selected from iRGD, cRGD, tLyp-1, Lyp-1, RPARPAR, Angiopep2, or GE11, and the active agent "D" is one selected from irinotecan, SN-38, 10-hydroxycamptothecin, or rubitecan.

In a more preferred embodiment, L is one selected from three-arm:

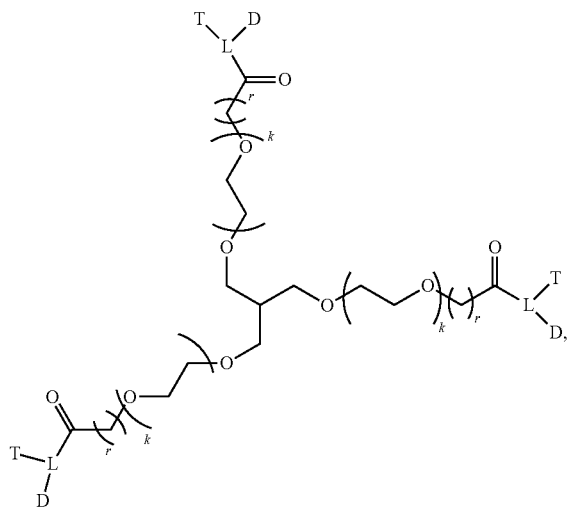
(IV)

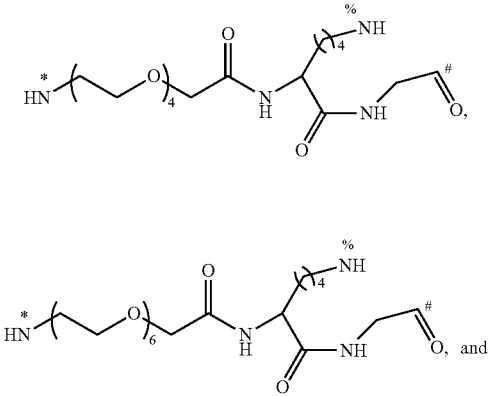

-continued
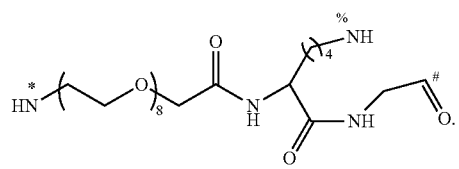
5
Based on formula (III), in certain specific embodiments, the compound of the present disclosure is as follows:
Compound a: D is irinotecan, and T is cRGD.
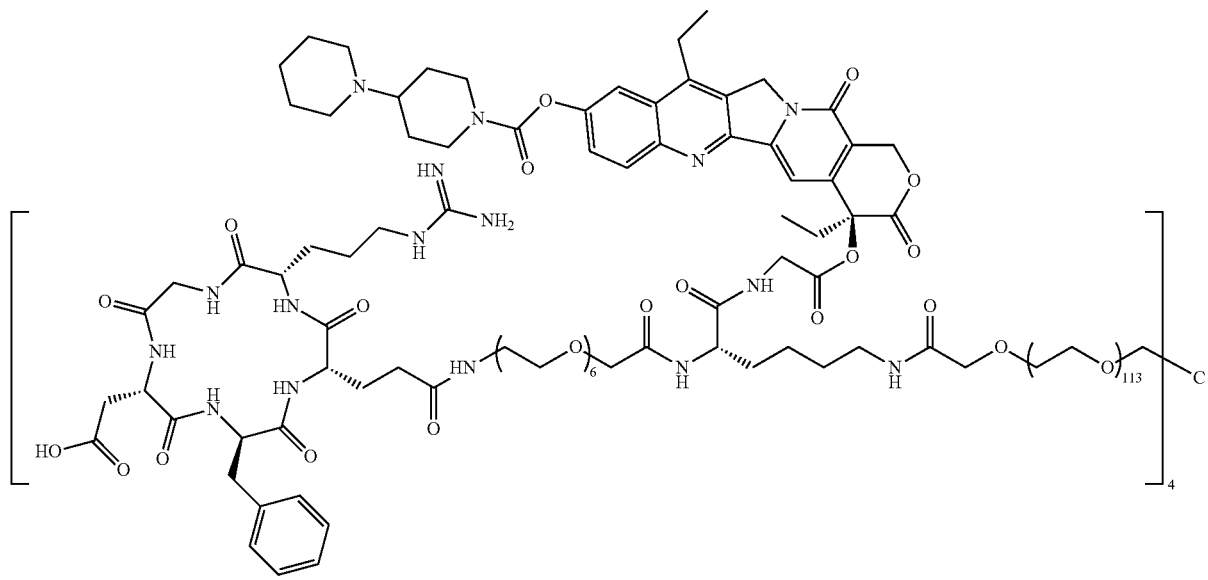
Compound a may also be written in the form depicted in FIG. 1.
Compound A is the hydrochloride salt of Compound a:
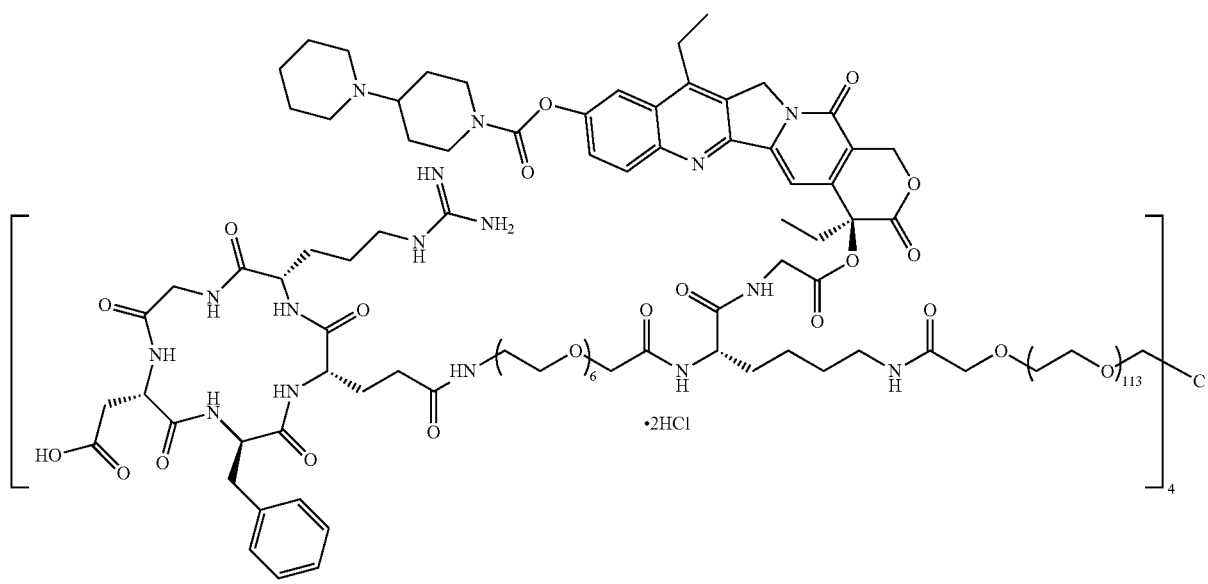

Compound b: D is irinotecan, and T is iRGD.
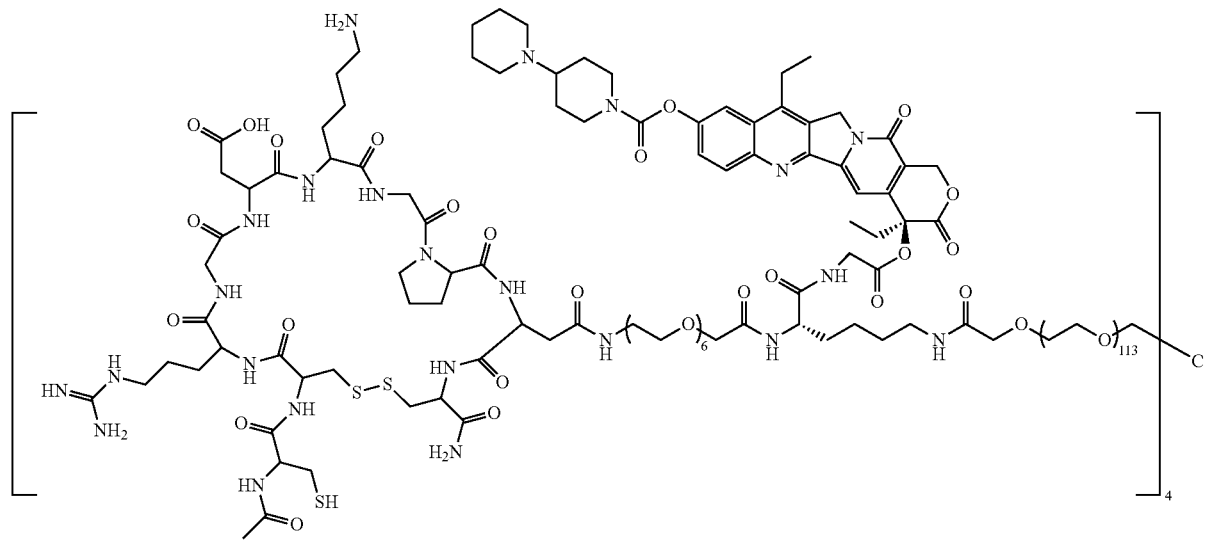
Compound B is the hydrochloride salt of Compound b:
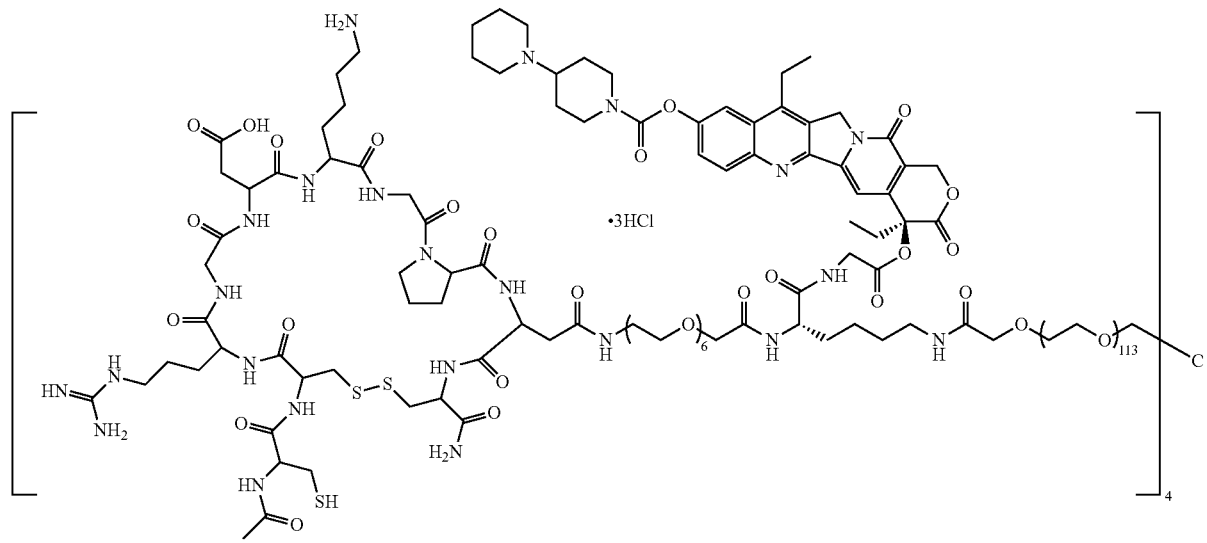

Compound c: D is irinotecan, and T is tLyP-1.
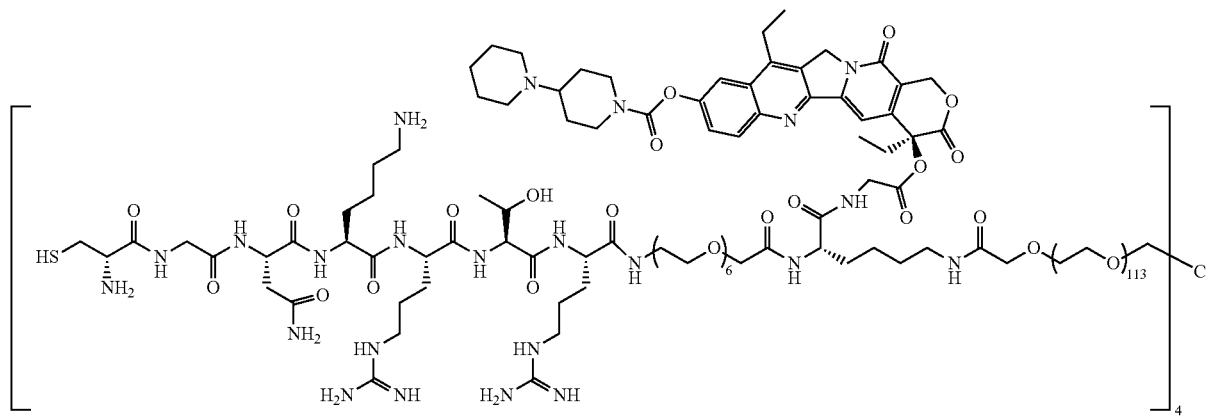
Compound C is the hydrochloride salt of Compound c:
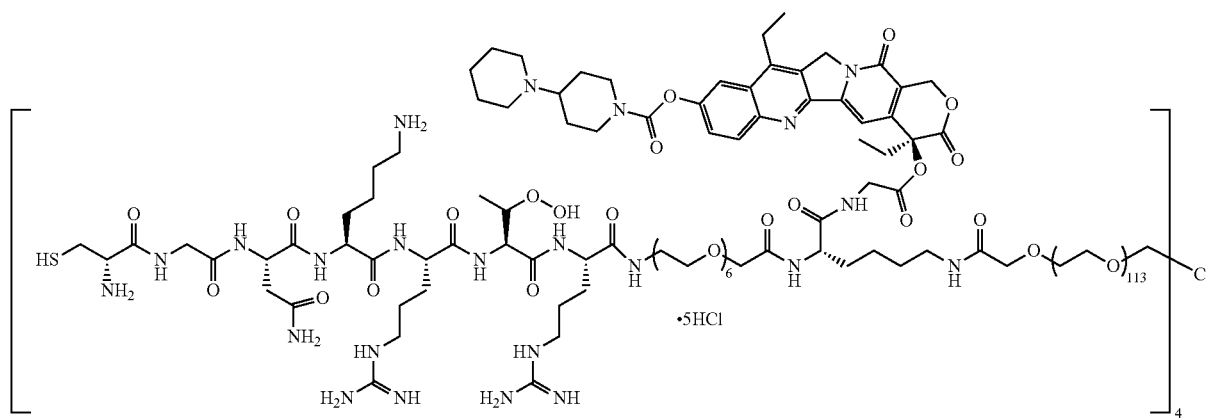
Compound d: D is irinotecan, and T is RPARPAR.
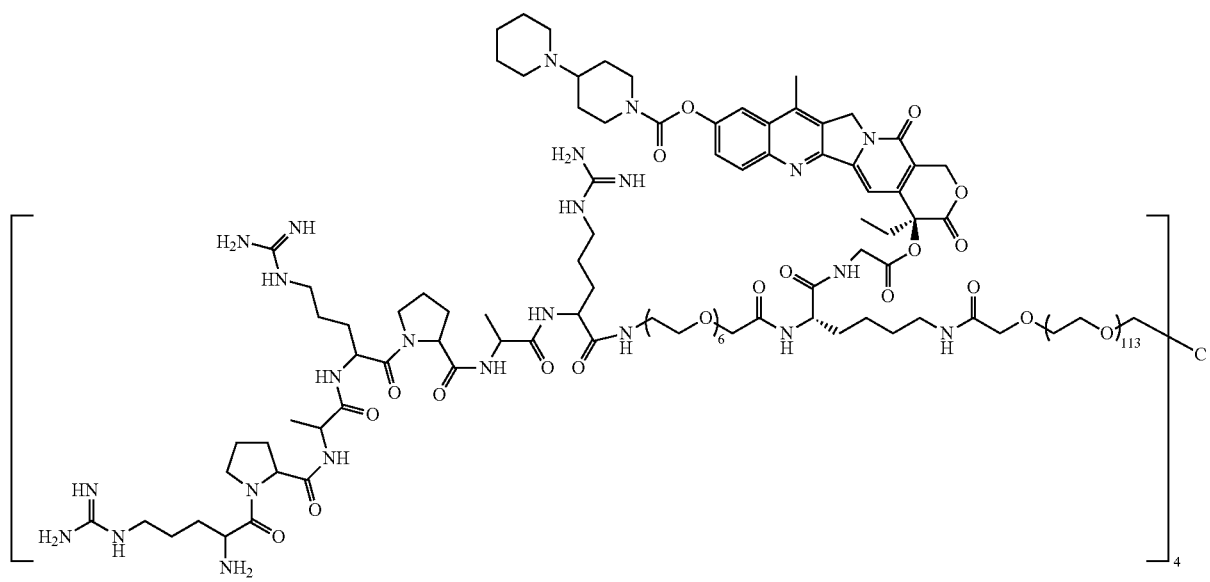

Compound D is the hydrochloride salt of Compound d:
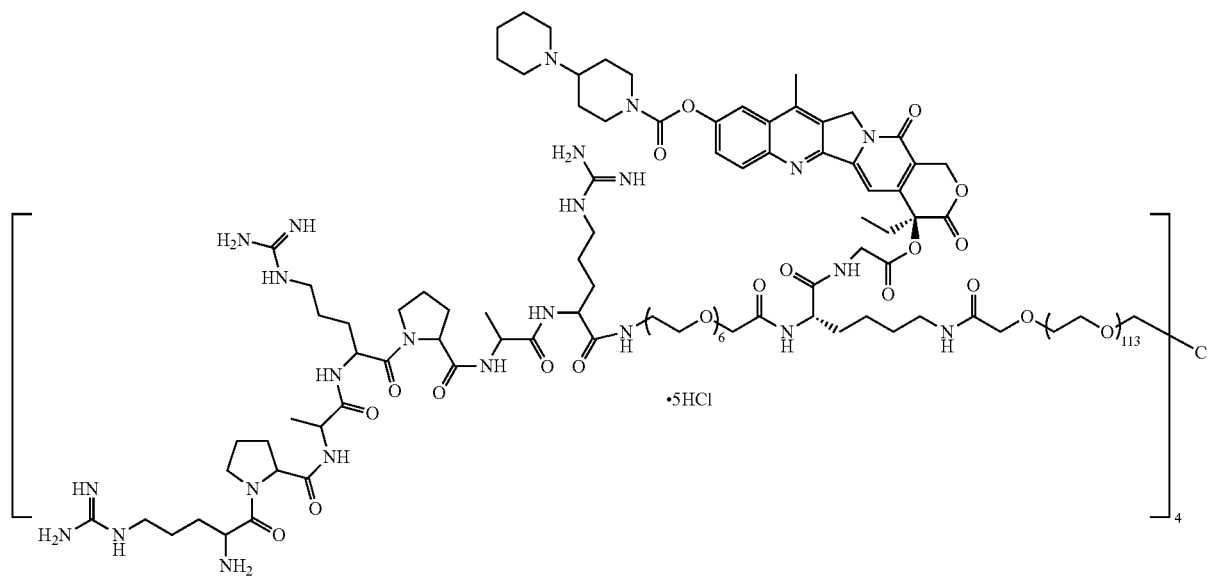
Compound e: D is irinotecan, and T is Angiopep-2.

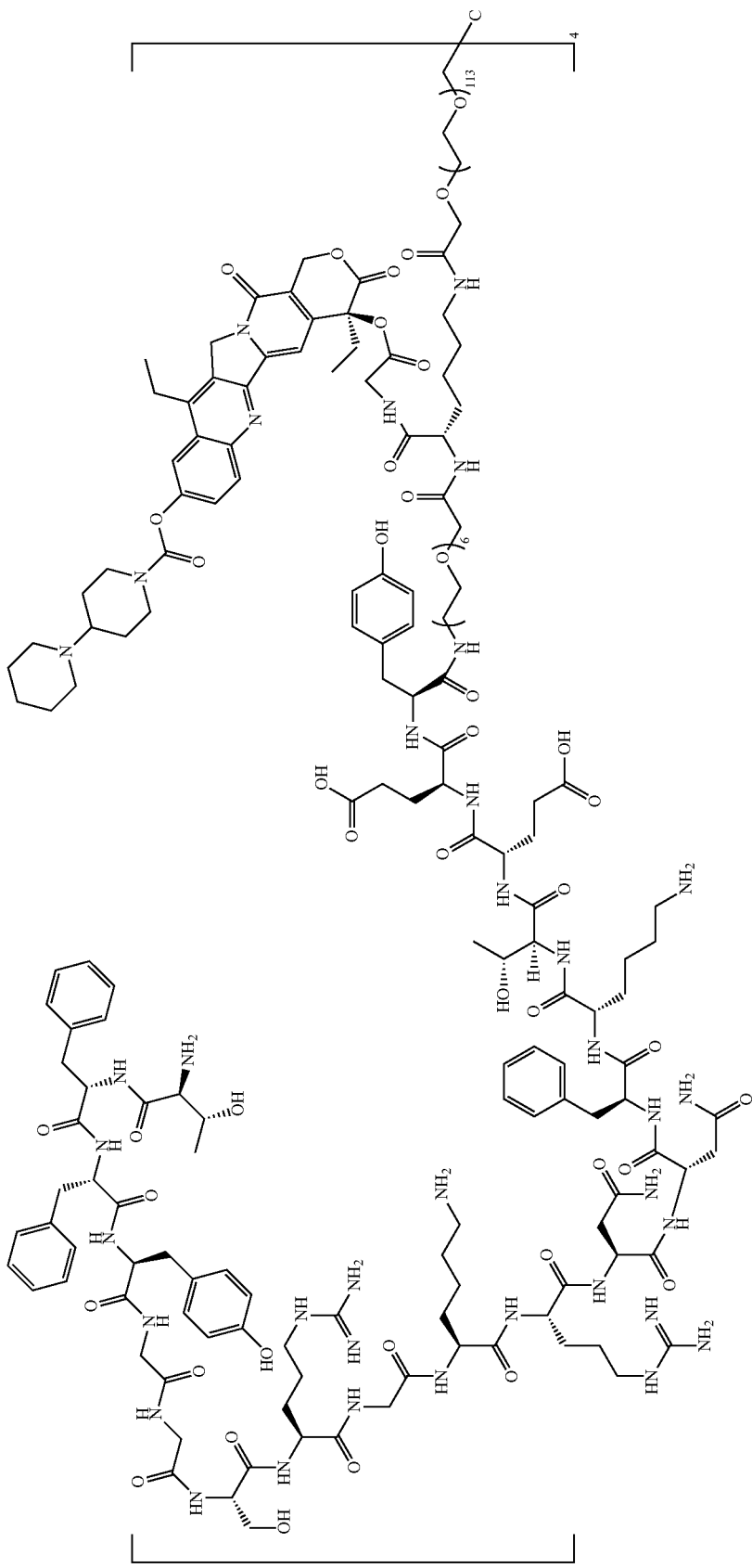

Compound E is the hydrochloride salt of Compound e.

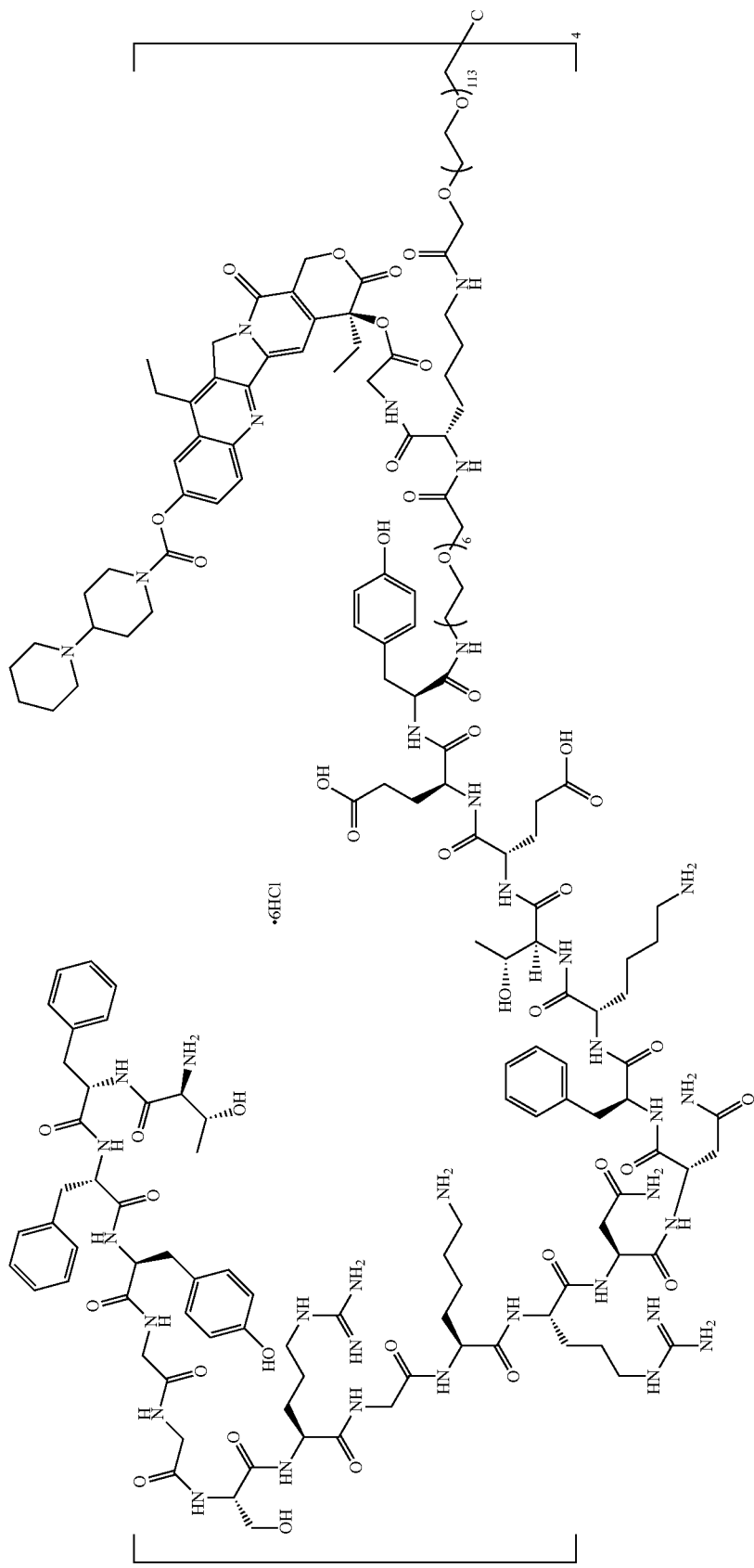

Compound e may also be written in the form depicted in FIG. 2.

Compound f: D is irinotecan, and T is GE11.

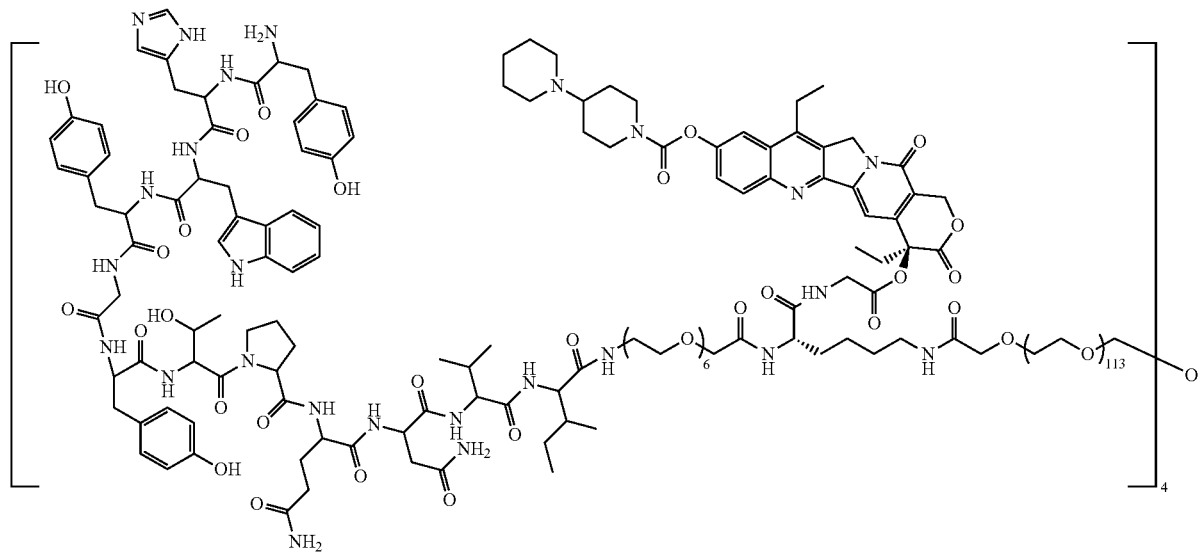

Compound F is the hydrochloride salt of Compound f:

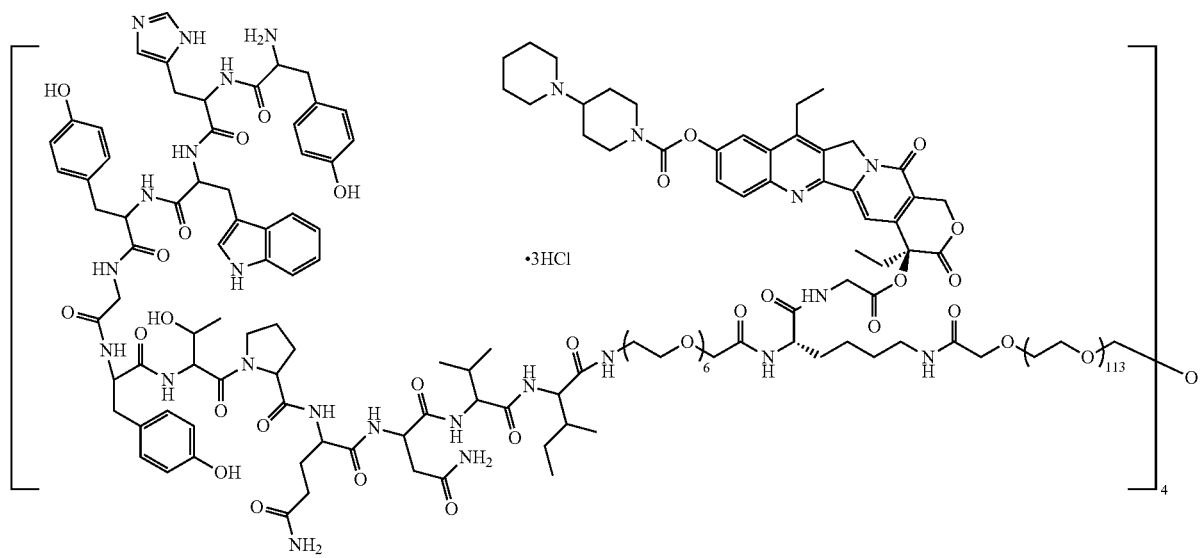

Compound F

Compound f may also be written in the form depicted in FIG. 3.

Here, it needs to be noted that, when forming salts, the branches of the conjugate of the present disclosure form salts separately with HCl. For example, as for Compound A, Compound B, Compound C, and Compound D, each branch has 2 molecules of HCl, and the entire molecule will have 8 molecules of HCl. As for Compound E, each branch has 6 molecules of HCl, and the entire molecule will have 24 molecules of HCL. As for Compound F, each branch has 3 molecules of HCl, and the entire molecule will have 12 molecules of HCl.

According to the inventive spirit of the present disclosure, in addition to the specific compounds disclosed above, those skilled in the art may also be capable of preparing more conjugates according to the technical schemes and preparation methods of the present disclosure, for example, ① D is SN-38, and T is a conjugate of iRGD, cRGD, tLyp-1, Lyp-1, RPARPAR, Angiopep2, or GE11, respectively; ② D is 10-hydroxycamptothecin, and T is a conjugate of iRGD, cRGD, tLyp-1, Lyp-1, RPARPAR, Angiopep2, or GE11, respectively; ③ D is rubitecan, and T is a conjugate of iRGD, cRGD, tLyp-1, Lyp-1, RPARPAR, Angiopep2, or GE11, respectively.

The conjugate of the present disclosure is a typical prodrug. By hydrolysis or enzymolysis, the active agent D is released, separated from the parent, and exerts physiological activity. The conjugate of the present disclosure shows high loading capacity, so that the total dosage may be lowered to treat a particular disease such as cancer. That is to say, the conjugate active agent carrier of the present disclosure is capable of covalently binding to a variety of active agent molecules effectively, allowing a greater amount of therapeutic agent (i.e., the active agent moiety) to be administered per certain amount of the conjugate. The conjugate of the present disclosure is modified by a water-soluble polymer, and the conjugate is also hydrophilic in nature. The bioavailability of the conjugate is enhanced especially when the active agent is a water-insoluble drug. As compared with an unconjugated drug, the conjugate of the present disclosure is capable of exhibiting a stronger effect and are more enriched in the tissues of the body of human or other animals.

The conjugate prodrug of the present disclosure possesses many unique properties, especially in the case where the active agent is an anticancer compound. This kind of prodrug is able to inhibit the tumor growth with higher efficiency. This small molecule used herein is a small molecule known to have anticancer properties. However, by binding to the multi-branched polymer as described above, the efficacy and pharmacokinetics of the conjugate are greatly improved as compared with this small molecule (for example, anticancer compound itself). The types of suitable solid tumors include colon cancer, breast cancer, ovarian cancer, pancreatic cancer, gastric cancer, brain glioma, and a malignant sarcoma, a cancer and a lymphoma of breast, ovary, colon, kidney, bile duct, lung and brain.

In summary, the present disclosure concerns a targeting anticancer conjugate modified by a multi-arm polymer, wherein the modification of a water-soluble polymer may enhance the water solubility of the conjugate so as to increase drug loading; the targeting property of the targeting molecule is increased, which enables the concentration of the conjugate to be higher in a target tissue; and L is an arbitrary linker, the role of which is to first link the targeting molecule to an anticancer drug, then link the targeting molecule and the anticancer drug to the polymer arm, enabling the entire conjugate to form an organic whole.

The pharmaceutically acceptable salts of the conjugate of the present disclosure are preferably hydrochlorides, and the salt formation may be carried out by conventional means in the field of medicinal chemistry. The pharmaceutically acceptable salts may also be trifluoroacetates, sulfates, phosphates, acetates, and the like.

In another aspect, the present disclosure provides a preparation method of said conjugate. During the preparation process of the conjugate of the present disclosure, POLY and the organic core R actually constitute a multi-arm polymer. In a preferred example of the present disclosure, this multi-arm polymer is multi-arm polyethylene glycol, which may be obtained from commercially available raw materials. For example, various types of four-arm, three-arm and eight-arm polyethylene glycol derivatives may be purchased from Beijing Jenkem Technology Co., Ltd. These commercially available multi-arm PEGs may participate in a reaction directly.

When preparing the conjugate of formula (III), the four-arm polyethylene glycol which is preferably used is as follows:

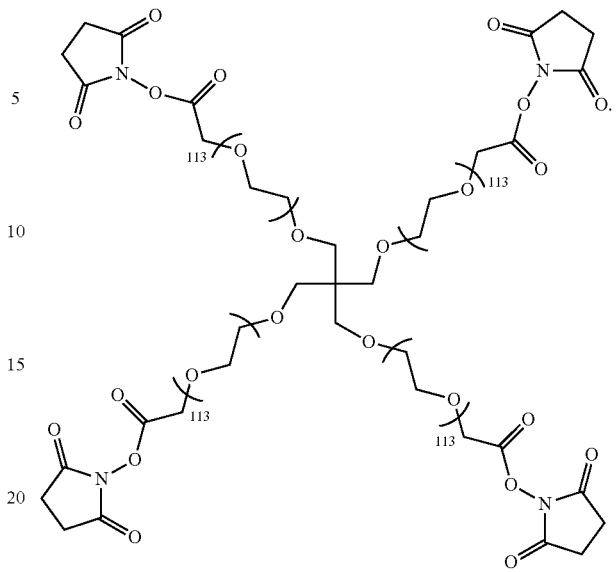

This preferred four-arm polyethylene glycol is referred to as 4ARM-PEG20K-SCM, and its molecular weight is approximately 20 kDa. Similarly, when preparing the conjugates of formula (IV) and formula (V), the molecular weights of the three-arm polyethylene glycol and the eight-arm polyethylene glycol which are used are also preferably about 20 kDa.

DESCRIPTION OF DRAWINGS

FIG. 1 shows the chemical structure of Compound a.

DETAILED DESCRIPTION

Figure 1:
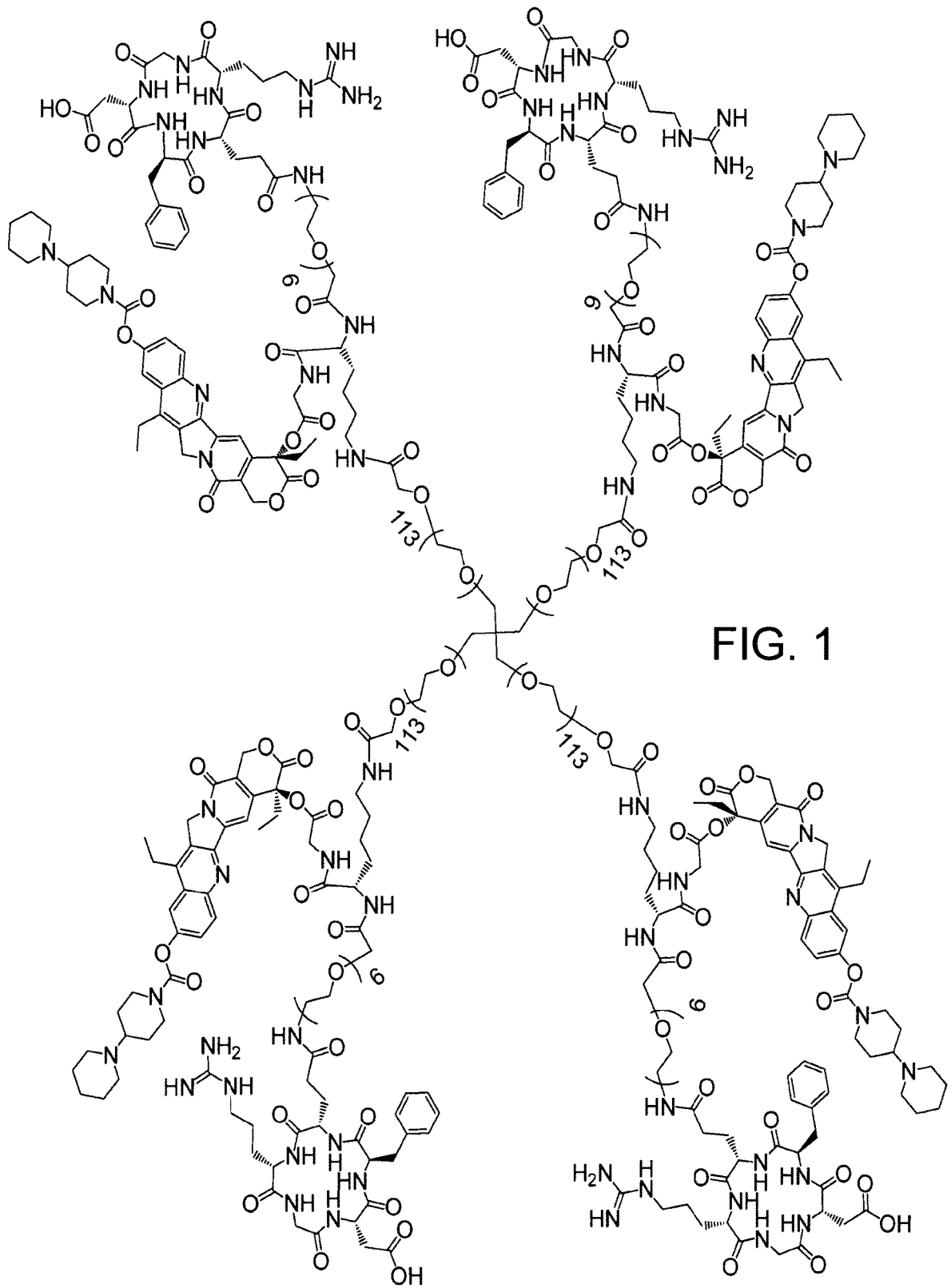
Figure 2:
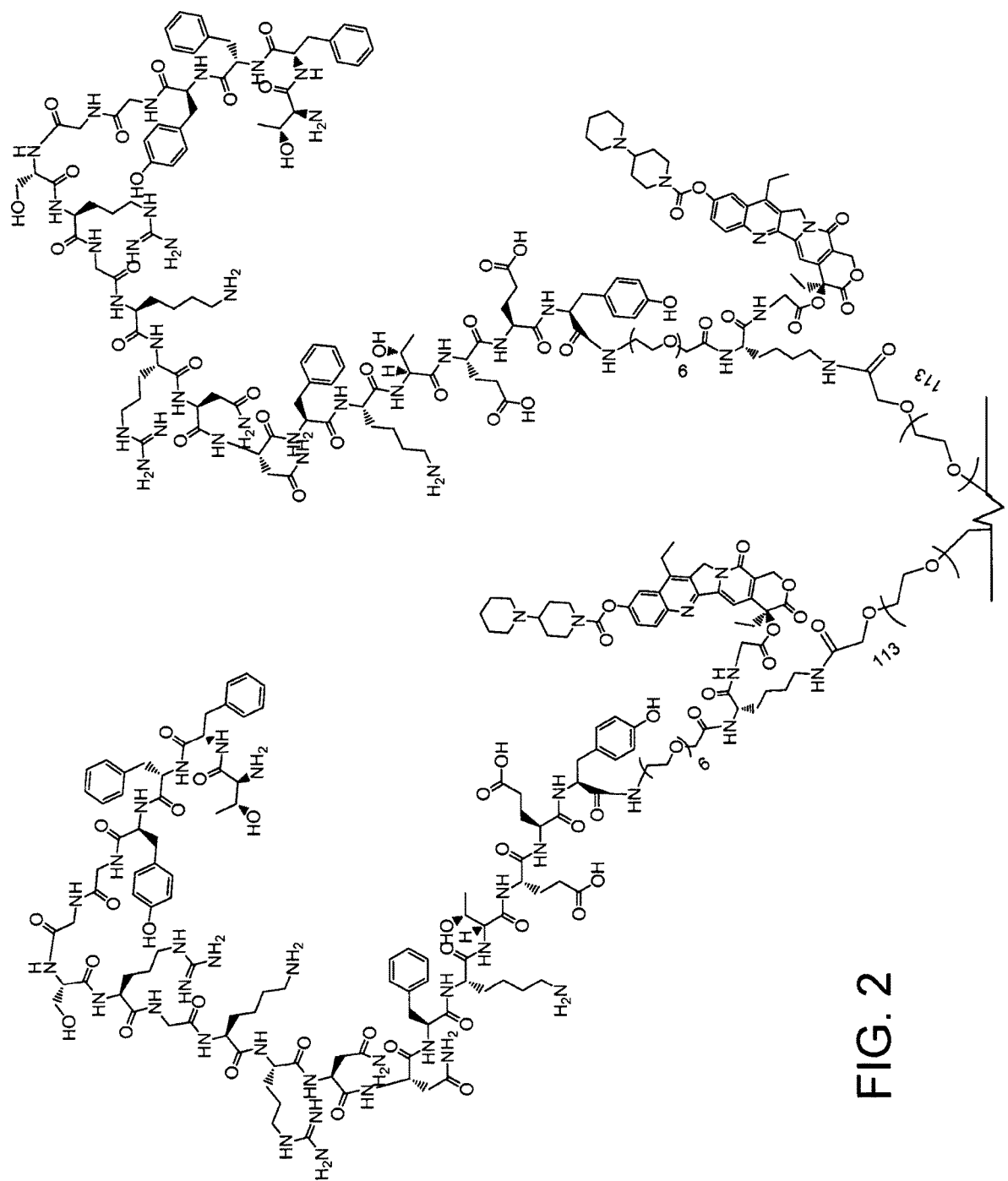
FIG. 2 shows the chemical structure of Compound e.
Figure 2:
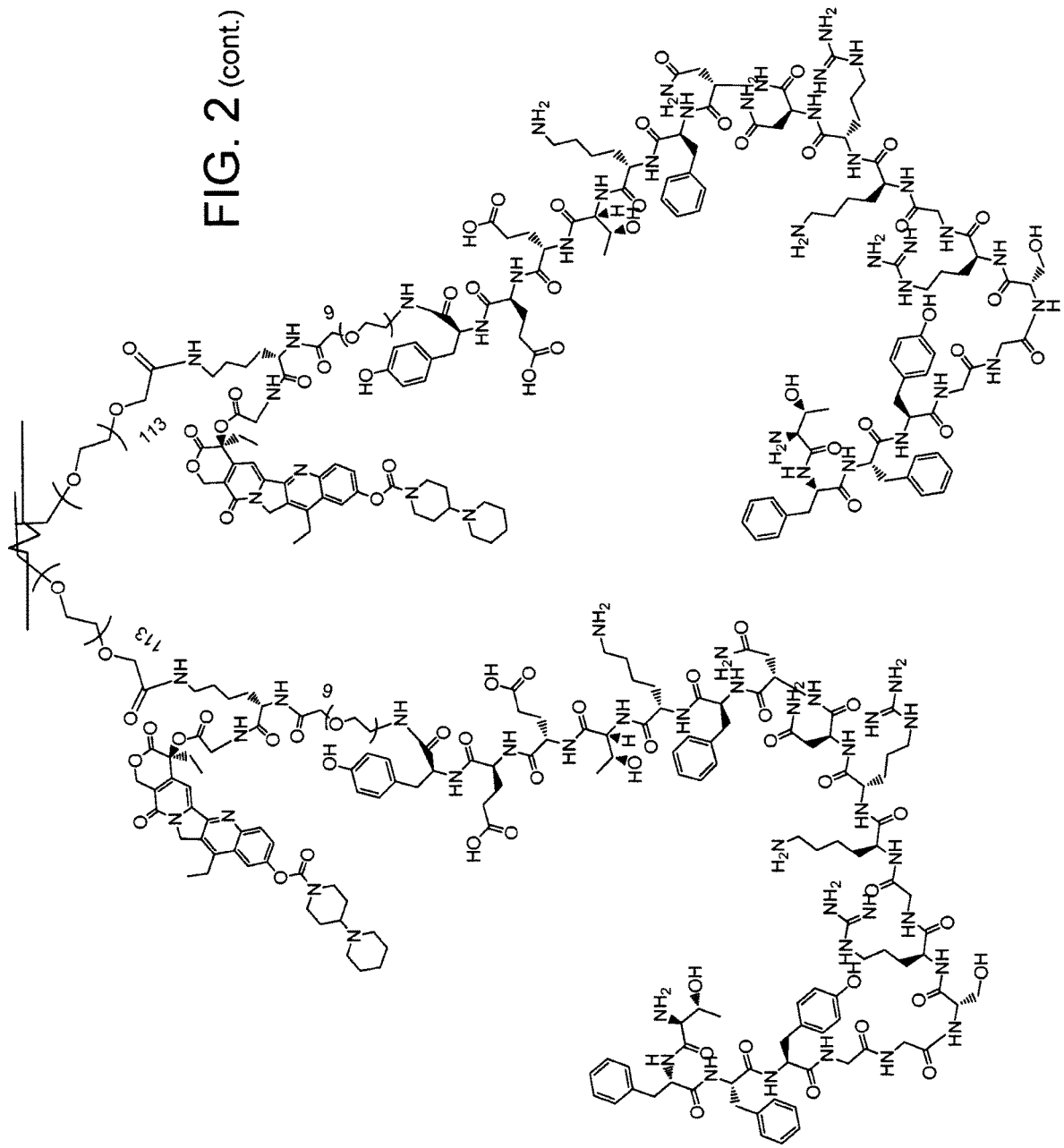
Figure 3:
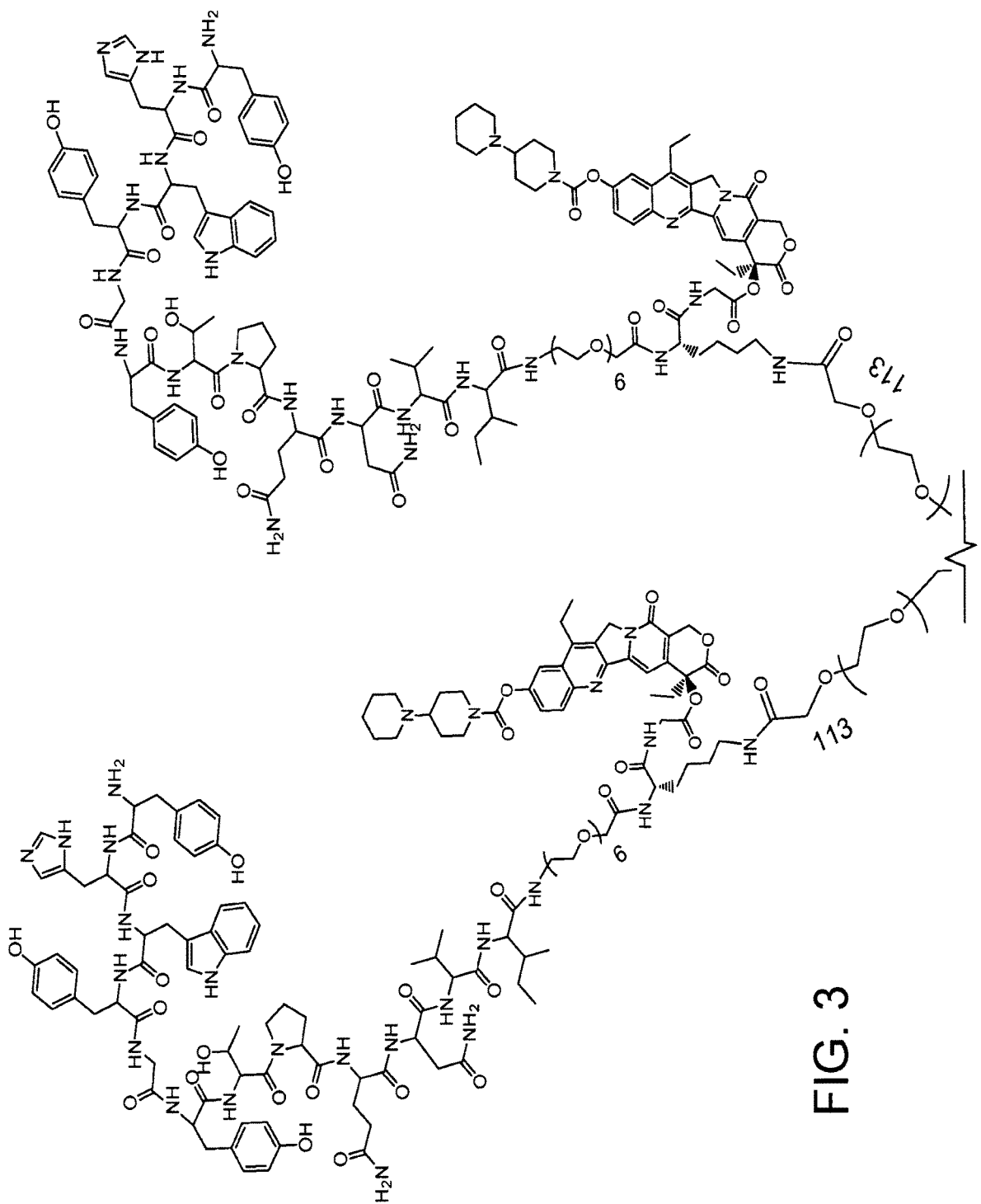
FIG. 3 shows the chemical structure of Compound f.
Figure 3:
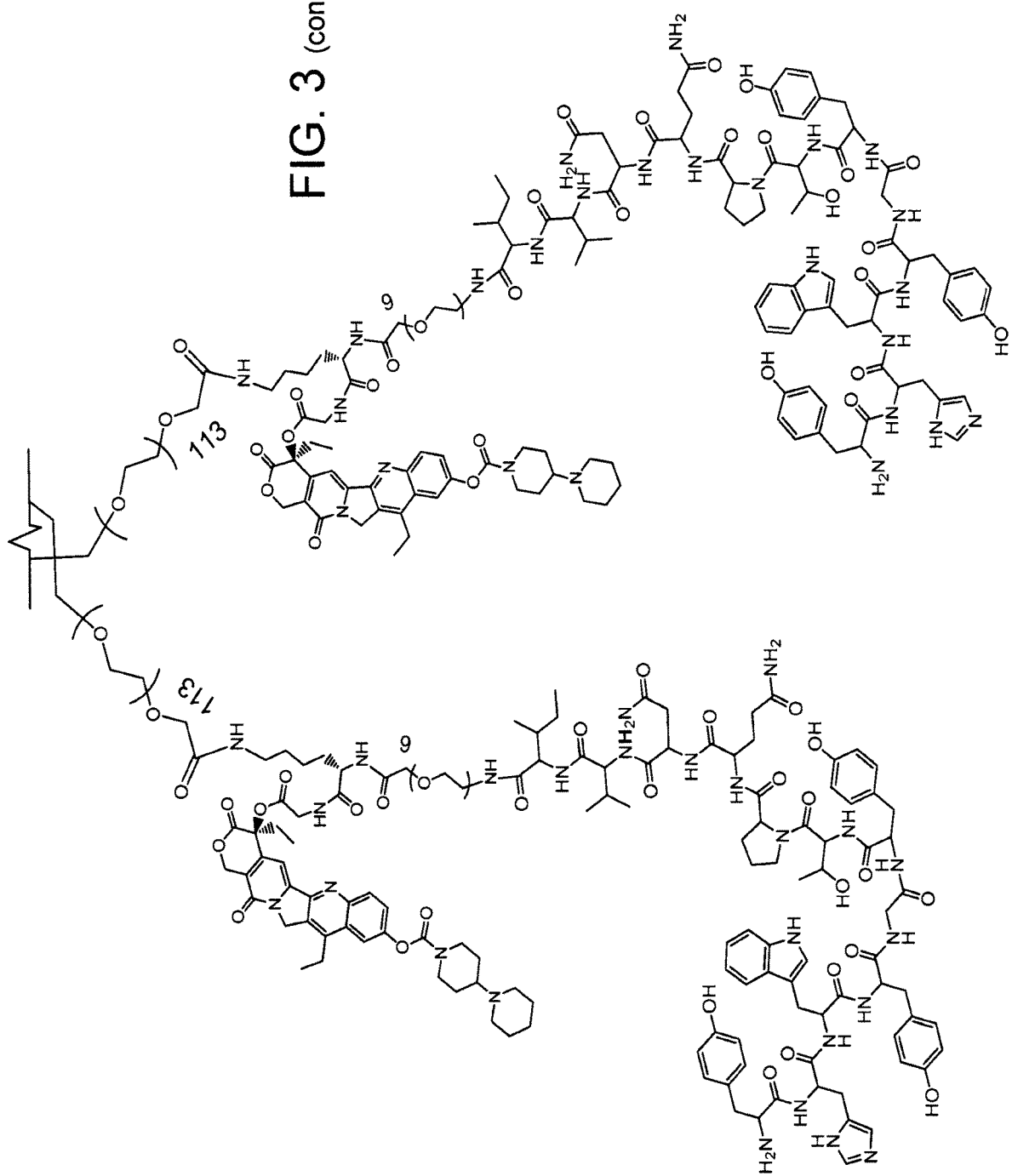

The present disclosure will be described in detail below. However, the present disclosure may be specifically embodied in many different forms, and it should not be limited to the examples described herein. The purpose of providing these examples is to make the disclosed content more complete and more comprehensive. The reagents and raw materials used are all commercially available except for those with preparation method provided. Among them, 4ARM-PEG20K-SCM is purchased from Beijing Jenkem Technology Co., Ltd.

Noun Explanations

| Abbreviations | Noun explanations |
|---|---|
| DMF | N,N-dimethylformamide |
| DCM | dichloromethane |
| Boc-Gly-OH | |
| DMAP | 4-dimethylaminopyridine |
| DCC | dicyclohexylcarbodiimide |
| IPA | isopropanol |
| EA | ethyl acetate |

| Abbreviations | Noun explanations |
|---|---|
| DEPC | diethyl cyanophosphonate |
| Pbf | 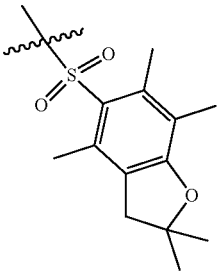 [SMILES: *S(=O)(=O)c1c(C)c(C)c2c(c1C)CC(C)(C)O2] |
| DIC | N,N-diisopropylcarbodiimide |
| DPPA | diphenyl phosphorazidate |
| NMM | N-methylmorpholine |
| MTBE | tert-butyl methyl ether |
| TFA | trifluoroacetic acid |
| TBME | tert-butyl methyl ether |

| Abbreviations | Noun explanations |
|---|---|
| Fmoc-OSU | 9-fluorenylmethyl-N-succinimidyl carbonate |
| DME | ethylene glycol dimethyl ether |
| HOBT | 1-hydroxybenzotriazole |
| THF | tetrahydrofuran |
| DIEA | N,N-diisopropylethylamine |
| DEA | triethylamine |
| H-Lys (Boc)-OBzl·HCl | 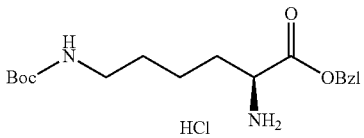 |
| TFE | trifluoroethanol |
| SPPS | solid-phase peptide synthesis |
| TIS | triisopropylsilane |

Example 1

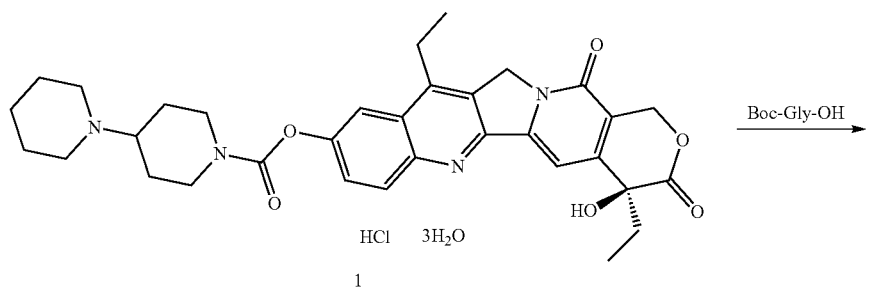

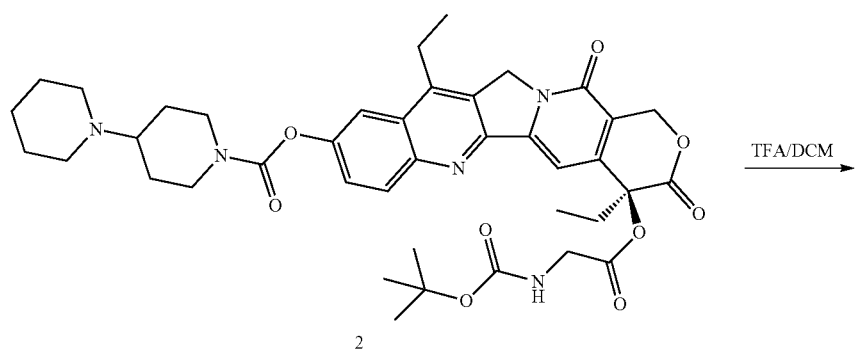

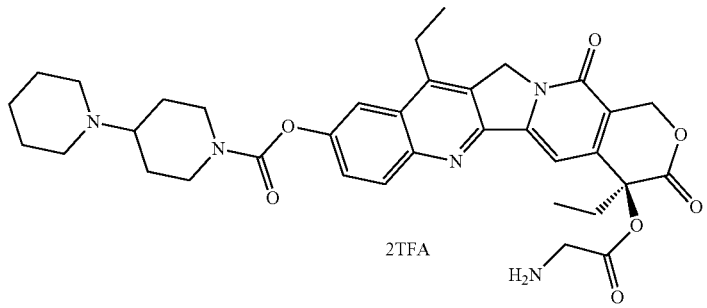

Preparation of Compound 2

To a 250 mL round-bottom flask, 3.50 g of Compound 1 (1.0 eq) and 52.5 mL of DMF were added and heated to 60° C. for dissolution. After 5 to 10 min, DMF was removed by distillation under reduced pressure. 300 mL of n-heptane was added and distilled under reduced pressure, and the procedure was repeated three times. After the mixture was dried by rotary evaporation, 105 mL of DCM, 1.08 g of Boc-Gly-OH (1.2 eq) and 63 mg of DMAP (0.1 eq) were added, a solution of 1.59 g of DCC (1.5 eq) in 10 mL of DCM was added dropwise, and the mixture was reacted at 20° C. for 4 hours. After the completion of the reaction was monitored by TLC, the mixture was filtered, and 120 mL of IPA was added when the mixture was concentrated to 25% of its total volume. 75% of the solvent was removed by distillation, and 150 mL of n-heptane was added. The mixture was stirred at room temperature for 1 hour, filtered, washed twice with n-heptane, and dried to obtain 4.02 g of Compound 2 as a pale yellow solid.

Preparation of Compound 3

To a 100 mL three-necked flask, 4.02 g of Compound 2 and 50 mL of DCM were added. After the mixture was stirred and dissolved, 11.6 mL of TFA was added dropwise, and the mixture was reacted at room temperature for 2 h. After the completion of the reaction was monitored by TLC, 150 mL of acetonitrile was added. After 120 mL of the solvent was distilled under reduced pressure, the mixture was poured into 320 mL of TBME solution, stirred for 30 min, and filtered. The filter cake was washed with TBME to obtain 4.00 g of Compound 3 as a pale yellow solid.

Example 2

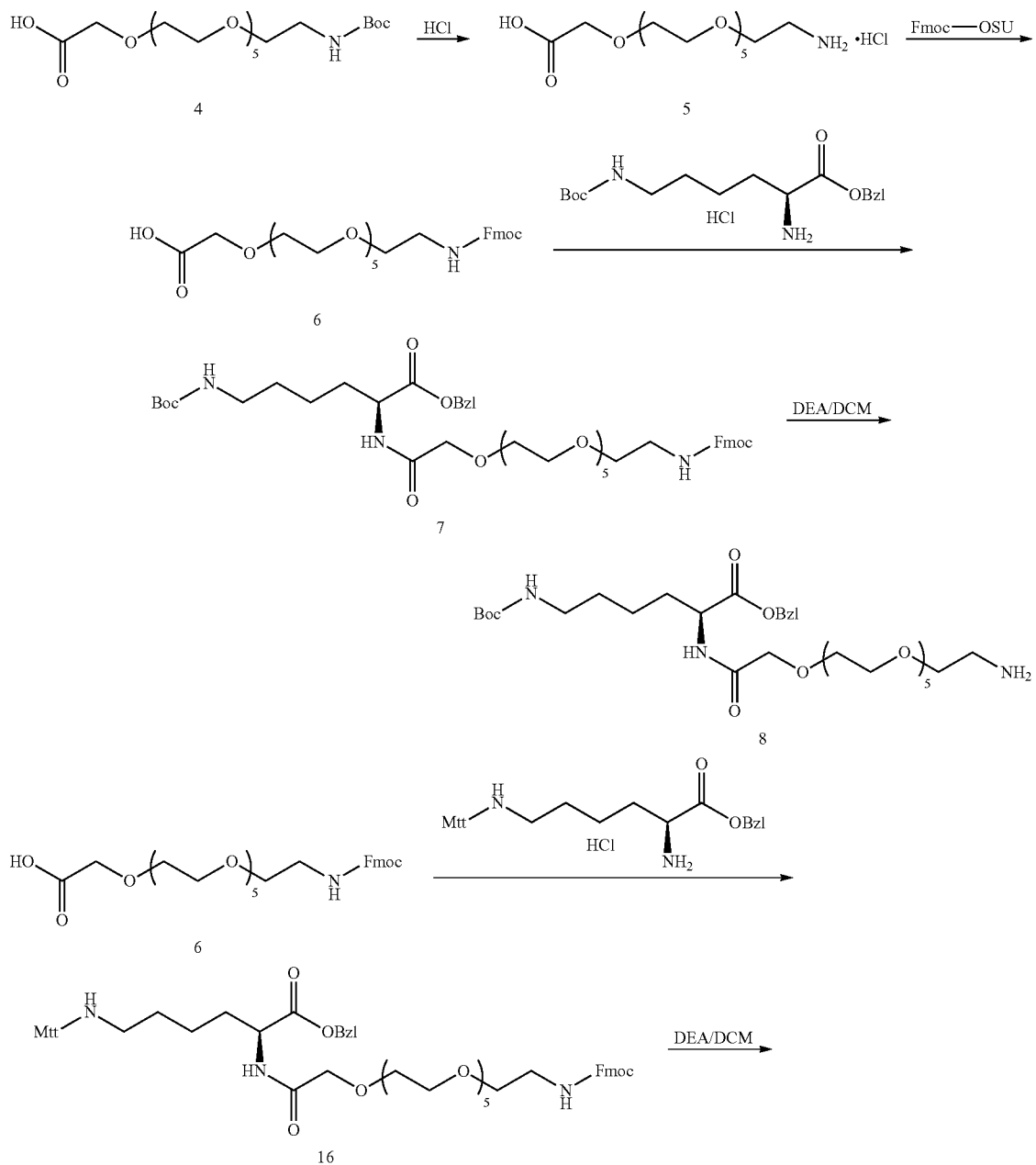

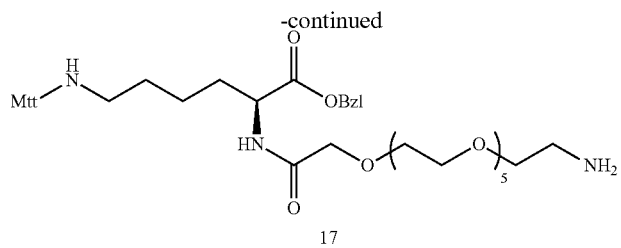

17

Preparation of Compound 5

To a 250 mL three-necked flask, 6.9 g of Compound 4 and 30 mL of EA were added, stirred and dissolved, and then cooled to 0° C. 40 mL of 0.3 M HC/EA was added, and the reaction was carried out for 2 h while the temperature was kept still. The completion of the reaction was monitored by TLC, and the mixture was concentrated to dryness so as to obtain Compound 5, which was directly subjected to the next reaction.

Preparation of Compound 6

Compound 5 (1.0 eq) was dissolved in 50 mL of purified water, and 3.96 g of sodium bicarbonate (2.0 eq) was added. 5.30 g of Fmoc-OSU (1.0 eq) was dissolved in 50 mL of DME, the mixture was added to the reaction flask containing Compound 5, 25 mL of THF was added additionally, and the mixture was stirred at room temperature for 2 hours. After the completion of the reaction was monitored by TLC, the organic solvent was removed by distillation, and EA was used to extract the impurities. The pH of the aqueous phase was adjusted to 3 to 4 with dilute hydrochloric acid, the mixture was extracted twice with EA, and the organic phases were combined and washed once with water. After being washed with saturated saline, the mixture was dried over anhydrous sodium sulfate and concentrated to obtain 8.4 g of Compound 6 as a pale yellow oil.

Preparation of Compound 7

To a 100 mL reaction flask, 4.00 g of Compound 6 (1.0 eq) and 2.92 g of H-Lys (Boc)-OBzl.HCl were added, and 40 mL of DCM was used for dissolution. 2.76 g of DIEA (3.0 eq) and 1.74 g of DEPC (1.5 eq) were added, and the mixture was stirred at room temperature for 2 hours. After the completion of the reaction was monitored by TLC, the mixture was washed with an acetic acid aqueous solution, washed with a sodium bicarbonate solution, washed once with water, and washed once with saturated saline. Then, the mixture was dried over anhydrous sodium sulfate and concentrated to obtain 7.0 g of Compound 7 as a pale yellow oil, which was directly subjected to the next reaction without purification. (Compound 16 was prepared by using the same method.)

Preparation of Compound 8

140 mL of 25% DEA/DCM was used to dissolve 7.0 g of Compound 7, and the mixture was stirred at room temperature for 6 hours. After the completion of the reaction was monitored by TLC, the mixture was concentrated to dryness, and 150 mL of EA were added. pH was adjusted to 3 to 4 by dilute hydrochloric acid, the mixture was subjected to liquid separation, and the aqueous phase was extracted twice with EA and then concentrated to dryness, so as to obtain 3.5 g of Compound 8 as a pale yellow solid. (Compound 17 was prepared by using the same method)

Example 3 Preparation of a Targeting Molecule cRGD with an Attached Protecting Group (Compound 11)

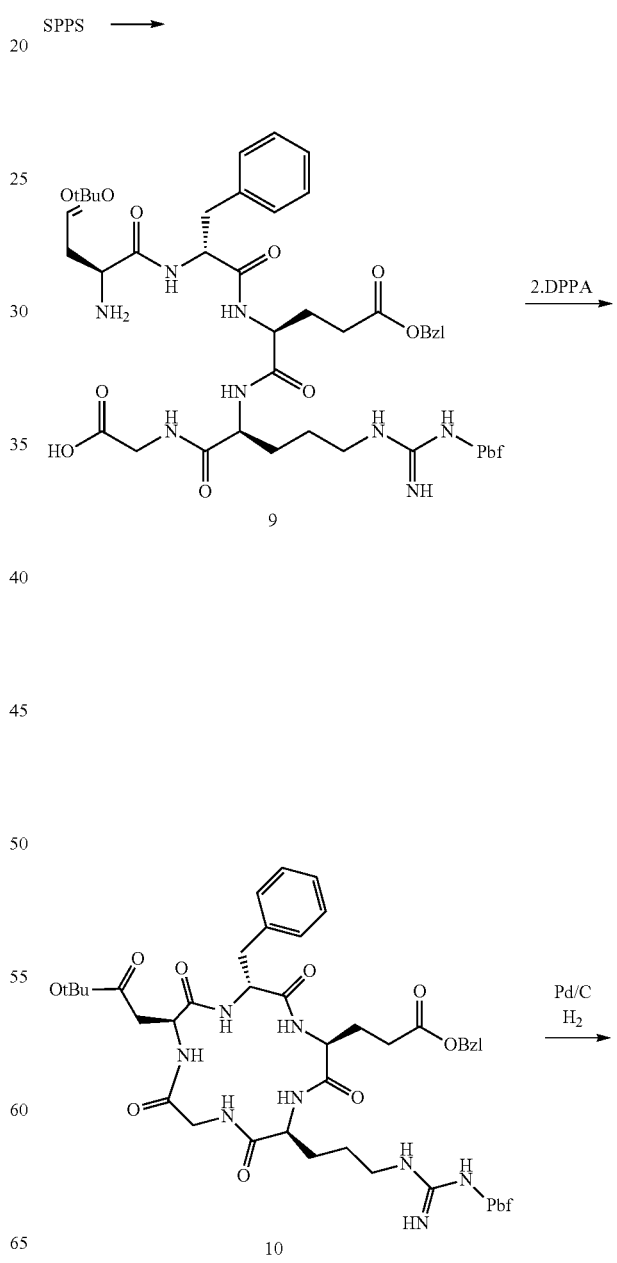

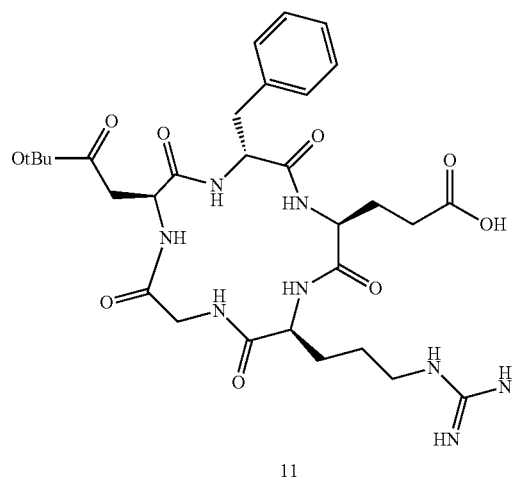

11

Preparation of Compound 9

2Cl-Trt Resin and Fmoc protection method were used, HOBT/DIC was adopted as a coupling reagent, DMF was a reaction solvent, the reaction was monitored by ninhydrin detection, and the following protecting amino acids were sequentially attached to the resin: Fmoc-Gly-OH, Fmoc-Arg(Pbf)-OH, Fmoc-Glu(OBzl)-OH, Fmoc-D-Phe-OH, and Fmoc-Asp(OtBu)OH. Fmoc was removed. The mixture was dried after being washed with DMF, DCM, and methanol. The cleavage reagent (acetic acid/TFE/DCM=1/2/7) was added, and the mixture was reacted for 2 hours. Ice-cold MTBE was used for precipitation, and the mixture was washed and dried to obtain Compound 9 as an off-white solid.

Preparation of Compound 10

To a 2 L three-necked flask, 14.0 g of Compound 9 (1.0 eq) was added, 1 L of DMF was added, the mixture was cooled to 0° C., and 9.2 g of sodium bicarbonate (8.0 eq) was added. After the mixture was dissolved to give a clear solution, 15.1 g of DPPA (4.0 eq) was added, and the temperature of the mixture was kept still overnight. After the completion of the reaction was monitored by TLC, the mixture was poured into 5 L of water, extracted twice with EA, washed with water, and washed with a saturated sodium chloride solution. Afterwards, the mixture was dried over anhydrous sodium sulfate and concentrated to obtain 11.5 g of Compound 10 as an off-white solid.

Preparation of Compound 11

To a 1 L hydrogenation reactor, 11.5 g of Compound 10, 1 L of methanol and 2.5 g of Pd/C were added, and the mixture was subjected to hydrogenation overnight. After the completion of the reaction was monitored by TLC, the mixture was filtered and concentrated to obtain 11.0 g of Compound 11 as a gray solid.

Example 4 Preparation of a Targeting Molecule iRGD with an Attached Protecting Group (Compound 20)

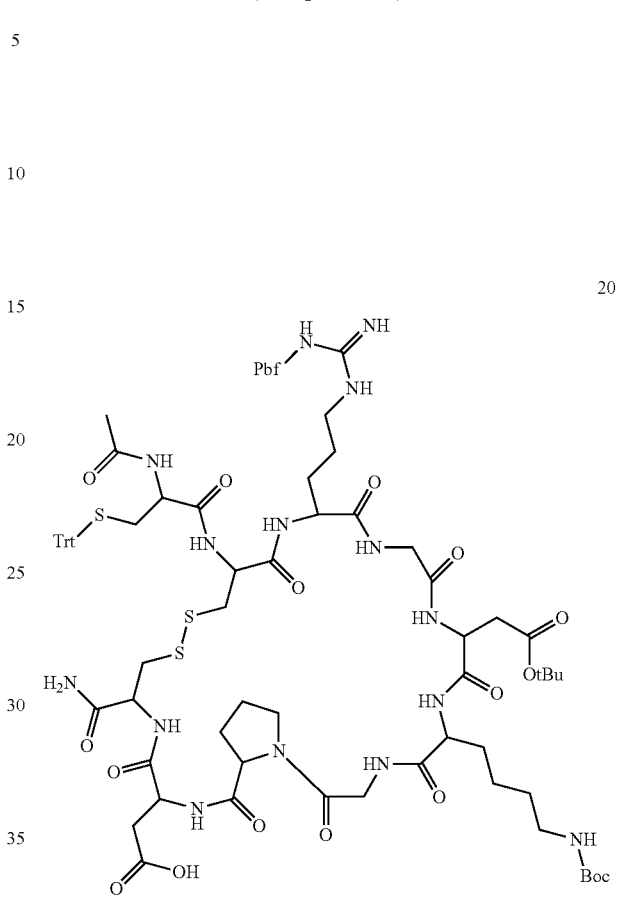

20

Fmoc-Sieber Resin was used, HOBT/DIC was adopted as a coupling reagent, DMF was a reaction solvent, the reaction was monitored by ninhydrin detection method, and the following protecting amino acids were sequentially attached to the resin: Fmoc-Cys(Acm)-OH, Fmoc-Asp(Alloc)OH, Fmoc-Pro-OH, Fmoc-Gly-OH, Fmoc-Lys(Boc)-OH, Fmoc-Asp(OtBu)OH, Fmoc-Gly-OH, Fmoc-Arg(Pbf)-OH, and Fmoc-Cys(Acm)-OH. After being washed with DMF, thallium trifluoroacetate (2.0 eq) was added. After being stirred for 18 hours, the mixture was washed with DMF, and Fmoc was removed. Fmoc-Cys(Trt)-OH was condensed, the mixture was washed with DMF, and Fmoc was removed. Acetic anhydride and pyridine were added to react for 20 min, and the mixture was washed with DMF. A solution of 3 eq of Pd(PPh$_3$)$_4$ in CHCl$_3$:AcOH:NMM (18:1:0.5) was added, the reaction was carried out for 2 h, and Alloc was removed. Then the mixture was washed with chloroform (6×20 mL), a solution of 20% HOAc in DCM, DCM, and DMF. The mixture was dried after being washed with DMF, DCM and methanol. 1% TFA/DCM was added, and the reaction was carried out for 2 hours. Ice-cold MTBE was used for precipitation, and the mixture was washed and dried to obtain Compound 20 as an off-white solid.

Example 5 Preparation of a Targeting Molecule tLyP-1 with an Attached Protecting Group (Compound 30)

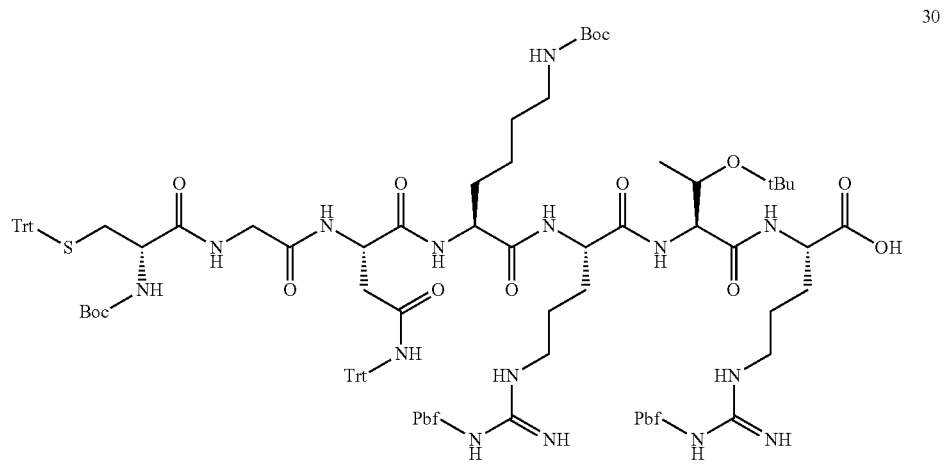

30

2Cl-Trt Resin was used, HOBT/DIC was adopted as a coupling reagent, DMF was a reaction solvent, the reaction was monitored by ninhydrin detection method, and the following protecting amino acids were sequentially attached to the resin: Fmoc-Arg(Pbf)-OH, Fmoc-Thr (tBu)-OH, Fmoc-Arg(Pbf)-OH, Fmoc-Lys (Boc)-OH, Fmoc-Asn(Trt)-OH, Fmoc-Gly-OH, and Boc-Cys(Trt)-OH. The cleavage reagent (acetic acid/TFE/DCM=1/2/7) was added, and the reaction was carried out for 2 hours. Ice-cold MTBE was used for precipitation, and the mixture was washed and dried to obtain Compound 30 as an off-white solid.

Example 6 Preparation of a Targeting Molecule RPARPAR with an Attached Protecting Group (Compound 40)

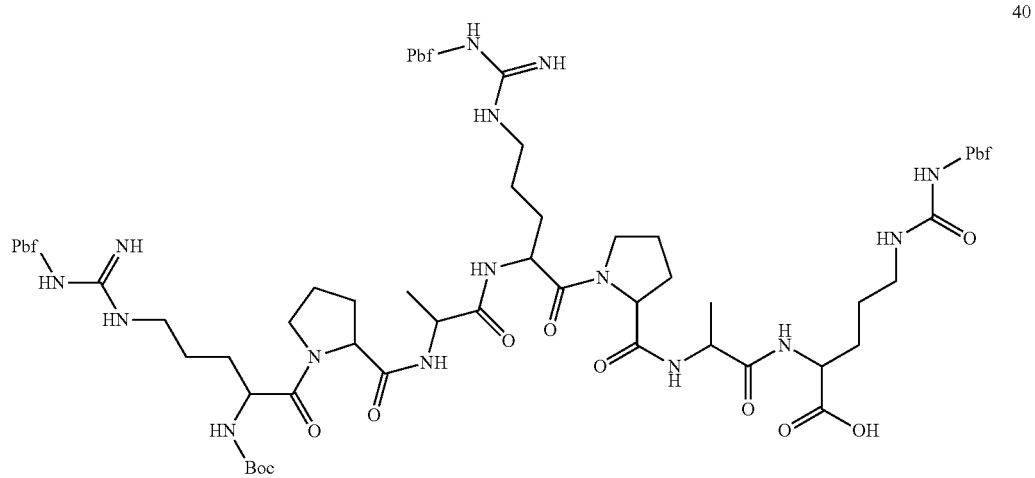

40

2Cl-Trt Resin was used, HOBT/DIC was adopted as a coupling reagent, DMF was a reaction solvent, the reaction was monitored by ninhydrin detection method, and the following protecting amino acids were sequentially attached to the resin: Fmoc-Arg(Pbf)-OH, Fmoc-Ala-OH, Fmoc-Pro-OH, Fmoc-Arg(Pbf)-OH, Fmoc-Ala-OH, Fmoc-Pro-OH, and Boc-Arg(Pbf)-OH. The cleavage reagent (acetic acid/TFE/DCM=1/2/7) was added, and the reaction was carried out for 2 hours. Ice-cold MTBE was used for precipitation, and the mixture was washed and dried to obtain Compound 40 as an off-white solid.

Example 7 Preparation of a Targeting Molecule Angiopep-2 with an Attached Protecting Group (Compound 50)

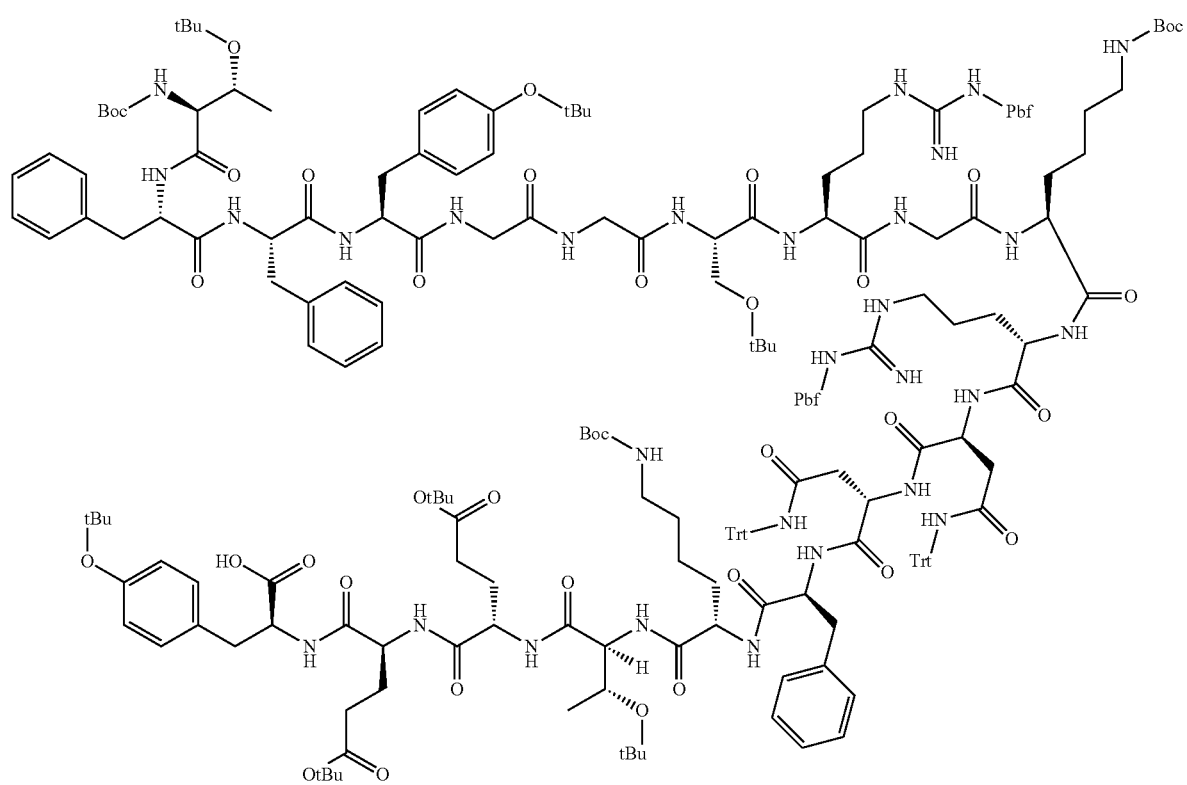

The sequence of Angiopep-2 was TFFYGGSRGKRNNFKTEEY.

2Cl-Trt Resin was used, HOBT/DIC was adopted as a coupling reagent, DMF was a reaction solvent, the reaction was monitored by ninhydrin detection method, and the following protecting amino acids were sequentially attached to the resin: Fmoc-Tyr(tBu)-OH, Fmoc-Glu(OtBu)-OH, Fmoc-Glu(OtBu)-OH, Fmoc-Thr(tBu)-OH, Fmoc-Lys(Boc)-OH, Fmoc-Phe-OH, Fmoc-Asn(Trt)-OH, Fmoc-Asn(Trt)-OH, Fmoc-Arg(Pbf)-OH, Fmoc-Lys(Boc)-OH, Fmoc-Gly-OH, Fmoc-Arg(Pbf)-OH, Fmoc-Ser(tBu)-OH, Fmoc-Gly-OH, Fmoc-Gly-OH, Fmoc-Tyr(tBu)-OH, Fmoc-Phe-OH, Fmoc-Phe-OH, and Boc-Thr(tBu)-OH. The cleavage reagent (acetic acid/TFE/DCM=1/2/7) was added, and the reaction was carried out for 2 hours. Ice-cold MTBE was used for precipitation, and the mixture was washed and dried to obtain Compound 50 as an off-white solid.

Example 8 Preparation of a Targeting Molecule GE11 with an Attached Protecting Group (Compound 60)

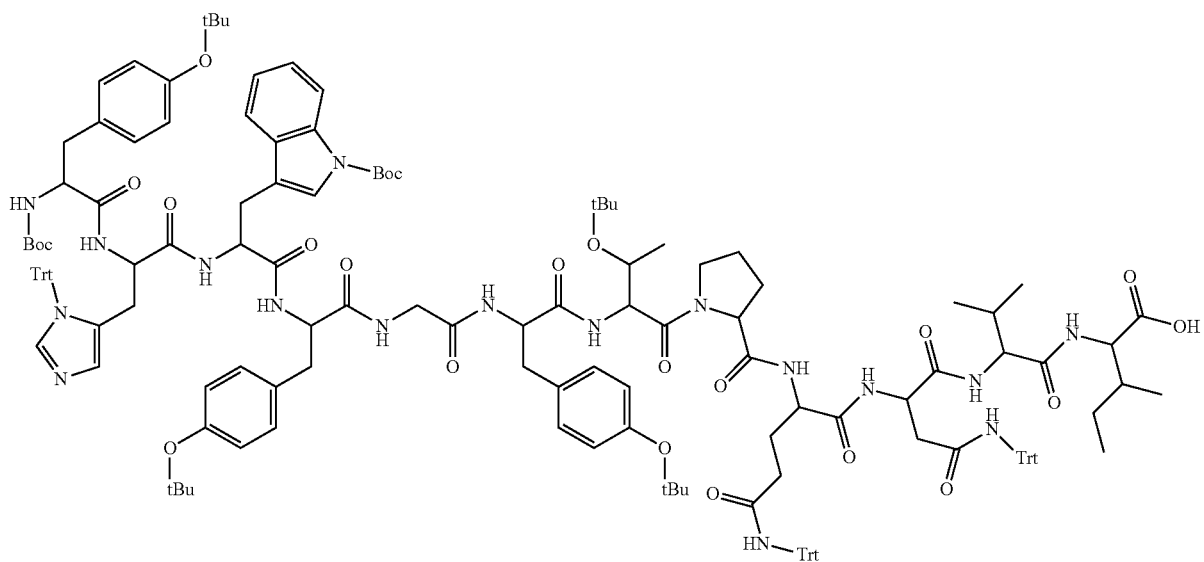

The sequence of GE11 was YHWYGYTPQNVI.

2Cl-Trt Resin was used, HOBT/DIC was adopted as a coupling reagent, DMF was a reaction solvent, the reaction was monitored by ninhydrin detection method, and the following to protecting amino acids were sequentially attached to the resin: Fmoc-Ile-OH, Fmoc-Val-OH, Fmoc-Asn(Trt)-OH, Fmoc-Gln(Trt)-OH, Fmoc-Pro-OH, Fmoc-Thr(tBu)-OH, Fmoc-Tyr(tBu)-OH, Fmoc-Gly-OH, Fmoc-Tyr(tBu)-OH, Fmoc-Trp(Boc)-OH, Fmoc-His(Trt)-OH, and Boc-Tyr(tBu)-OH. The cleavage reagent (acetic acid/TFE/DCM=1/2/7) was added, and the reaction was carried out for 2 hours. Ice-cold MTBE was used for precipitation, and the mixture was washed and dried to obtain an off-white solid 60.

Example 9 Preparation of Compound a and Compound A

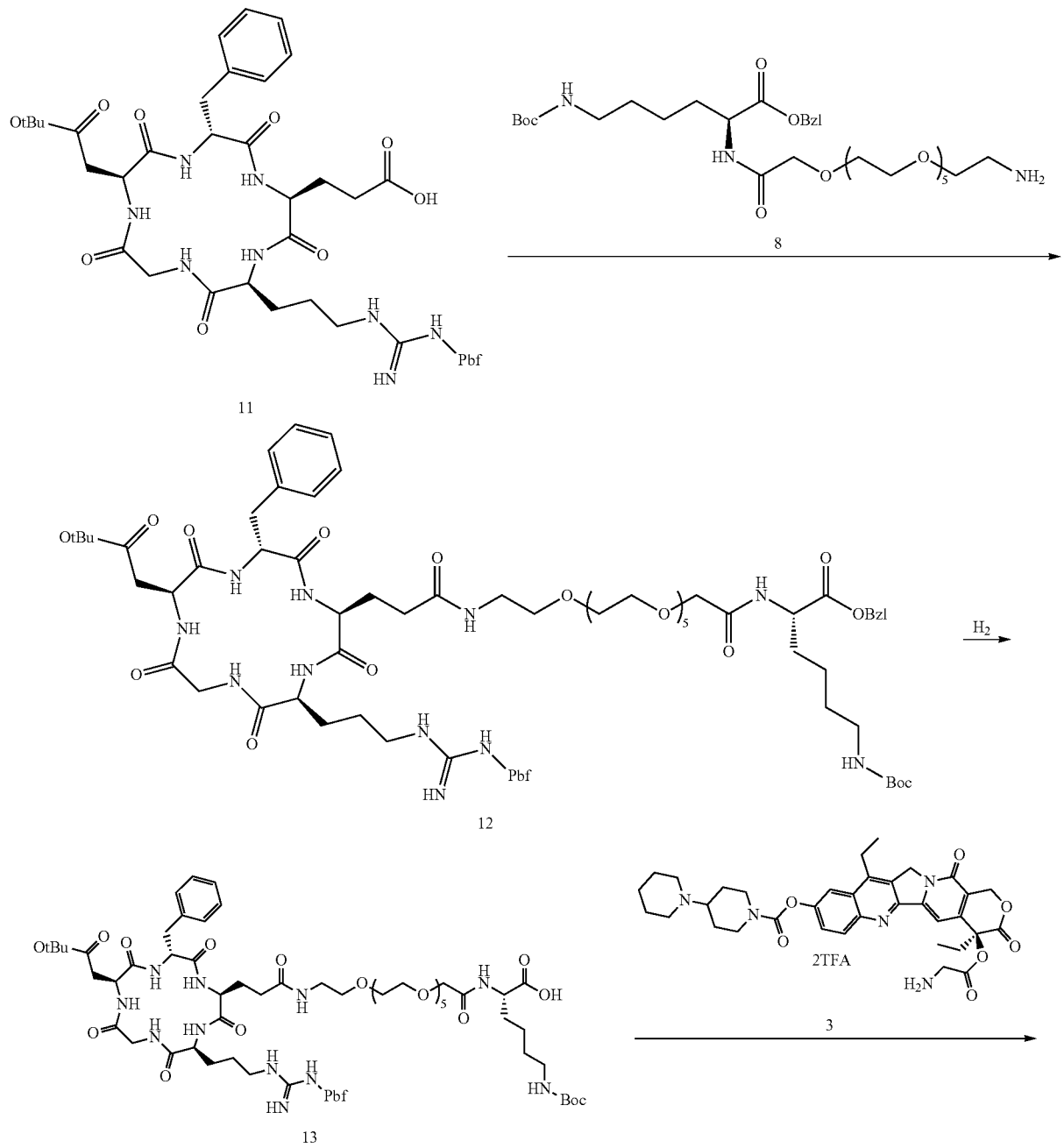

-continued
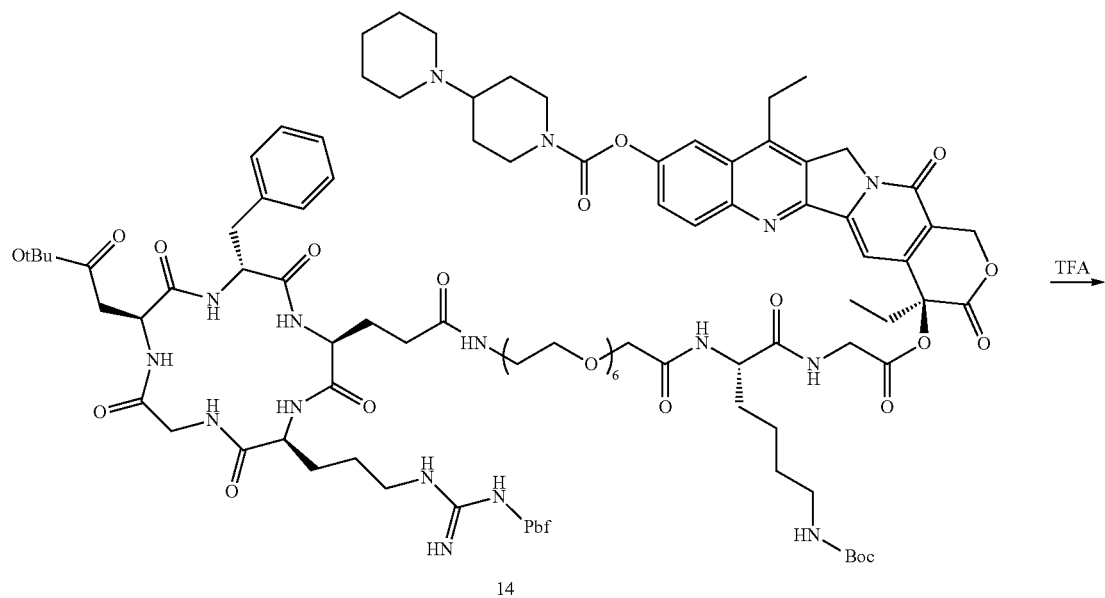
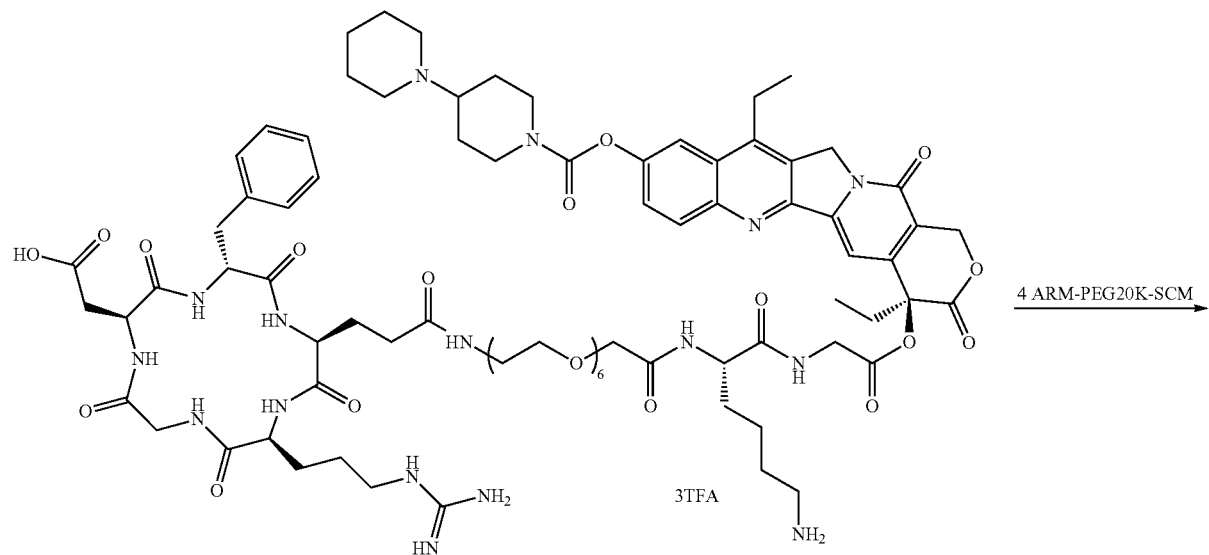

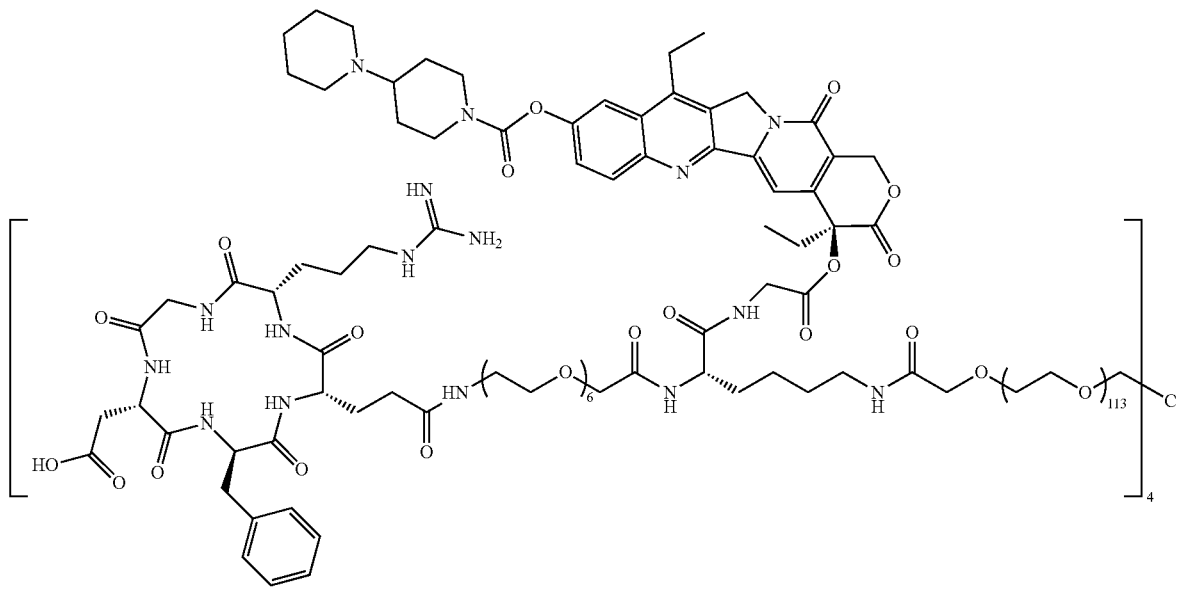

Preparation of Compound 12

To a 5 mL reaction flask, 480 mg of Compound 11 (1.0 eq), 380 mg of Compound 8 (1.1 eq), 1 mL of DMF, 203 mg of DIEA (3.0 eq) and 128 mg of DEPC (1.5 eq) were added, and the mixture was reacted at room temperature for 2 h. After the completion of the reaction was monitored by TLC, the mixture was poured into 10 mL of water, extracted twice with EA, and washed with dilute hydrochloric acid, a sodium bicarbonate solution and a saturated sodium chloride solution. Afterwards, the mixture was dried over anhydrous sodium sulfate and concentrated to obtain 0.8 g of Compound 12 as a jelly-like solid, which was directly subjected to the next reaction.

Preparation of Compound 13

To a 200 mL hydrogenation reactor, 0.8 g of Compound 10, 30 mL of methanol and 0.28 g of Pd/C were added, and the mixture was subjected to hydrogenation overnight. After the completion of the reaction was monitored by TLC, the mixture was filtered and concentrated to obtain 0.66 g of Compound 13 as a gray solid.

Preparation of Compound 14

To a 100 mL reaction flask, 6.60 g of Compound 13 (1.0 eq), 3.59 g of Compound 3 (1.05 eq), 66 mL of DMF, 1.16 g of DIEA (3.0 eq) and 1.10 g of DEPC (1.5 eq) were added, and the mixture was reacted at room temperature for 2 h. After the completion of the reaction was monitored by TLC, the mixture was poured into 700 mL of TBME and subjected to suction filtration after pulping. After the solid was dissolved in 150 mL of DCM, the mixture was poured into 1.5 L of TBME, subjected to pulping and suction filtration, and dried to obtain 9.0 g of Compound 14 as gray powder, which was directly subjected to the next reaction.

Preparation of Compound 15

To a 250 mL reaction flask, 9.0 g of Compound 14 was added, and 92.5% TFA/2.5% water/2.5% TIS was added as a cleavage reagent. The mixture was stirred at room temperature for 2 h, ice-cold MTBE was used for precipitation, and the mixture was centrifuged and washed. The crude product was purified by reverse-phase HPLC and lyophilized to obtain 5.0 g of Compound 15 as a pale yellow floccule.

Preparation of Compound a

To a reaction flask, 2.3 g of Compound 15 (4.5 eq), 6.0 g of 4ARM-PEG20K-SCM (1.0 eq), 60 mL of DMF and 0.27 g of TEA (9.0 eq) were added, and the mixture was reacted at room temperature. After there was no significant reaction progress monitored by HPLC, the mixture was poured into 1000 mL of TBME, and subjected to pulping and suction filtration to obtain 7.6 g of crude product a as off-white powder. The crude product was desalted after being purified by HPLC. The organic solvent was removed by concentration, and the resultant was lyophilized to obtain 3.4 g of Compound a as off-white powder.

Preparation of Compound A

After obtaining a powdery crude product of Compound a, the crude product was desalted after being purified by HPLC. The organic solvent was removed by concentration, pH was adjusted to 5 to 6 by dilute hydrochloric acid, and the resultant was lyophilized to obtain 3.4 g of Compound A as yellow-green powder.

The molecular weight detected by MALDI-TOF was 25480.27.

Example 10 Preparation of Compound b and Compound B
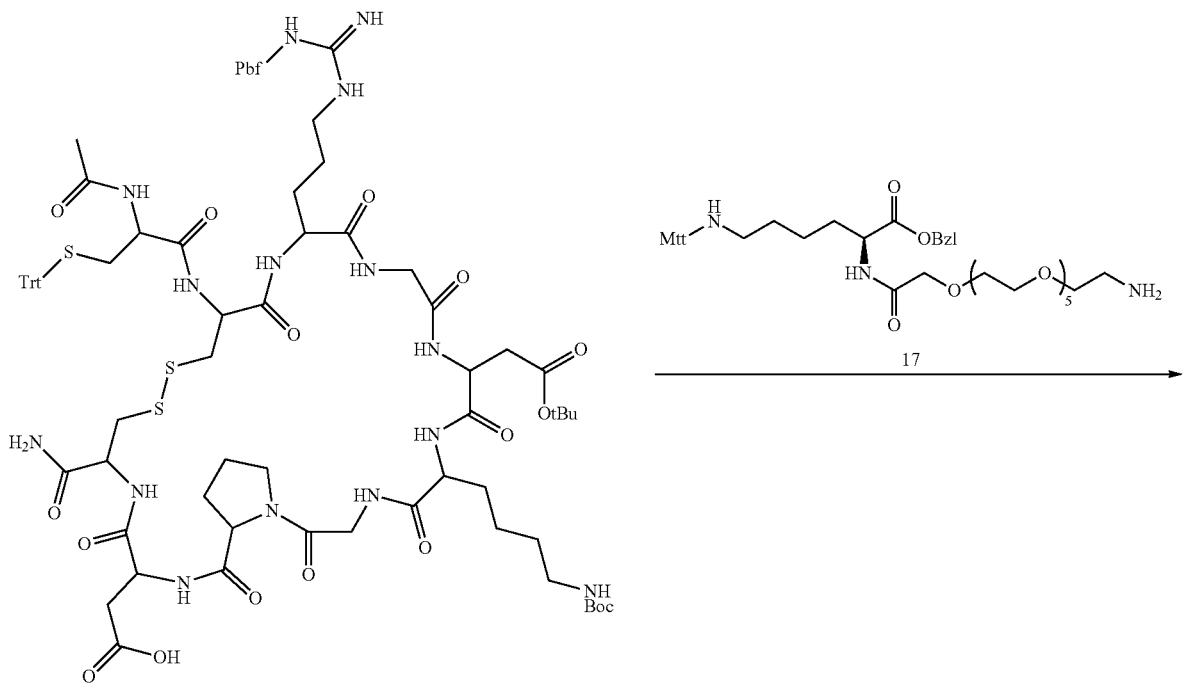
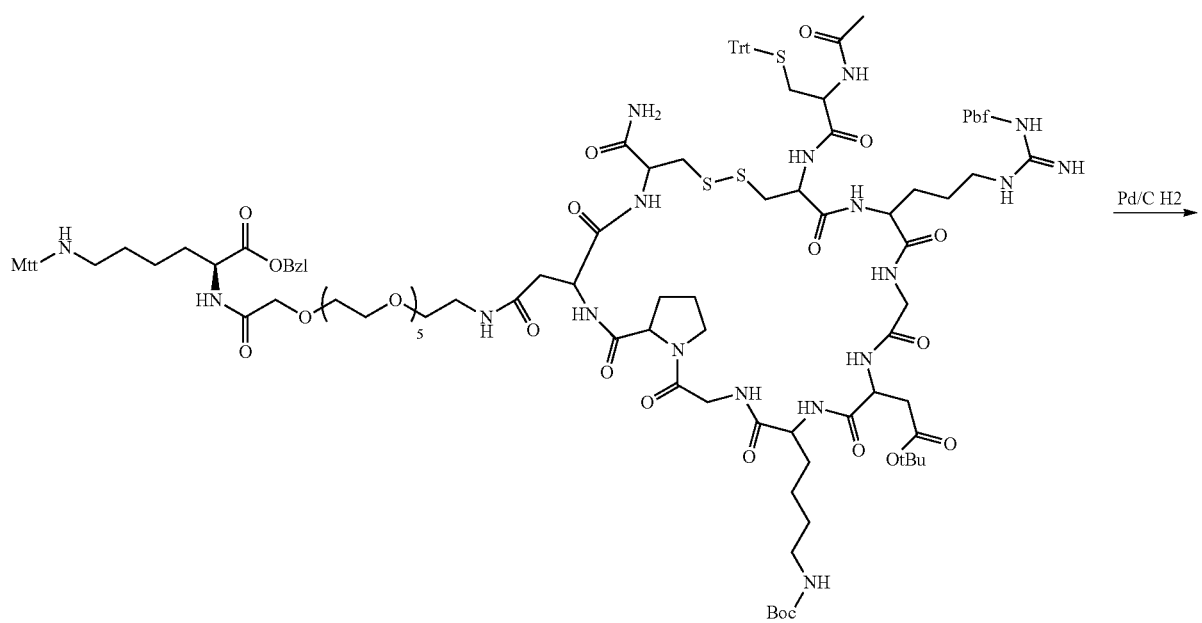

57
58
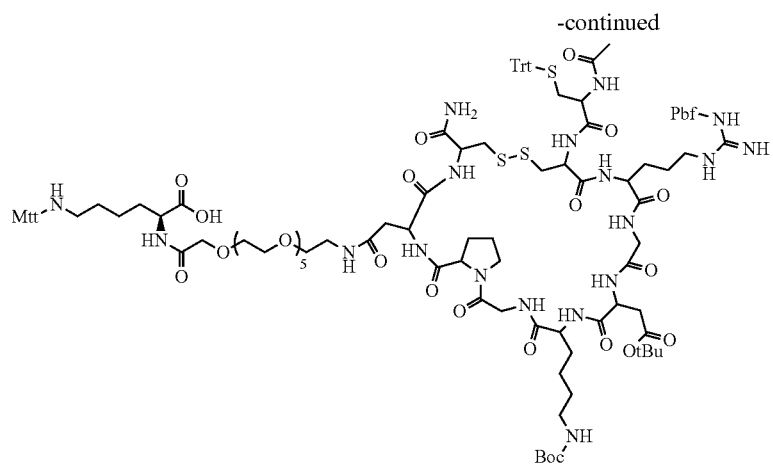
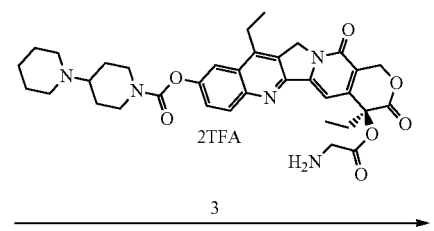
22
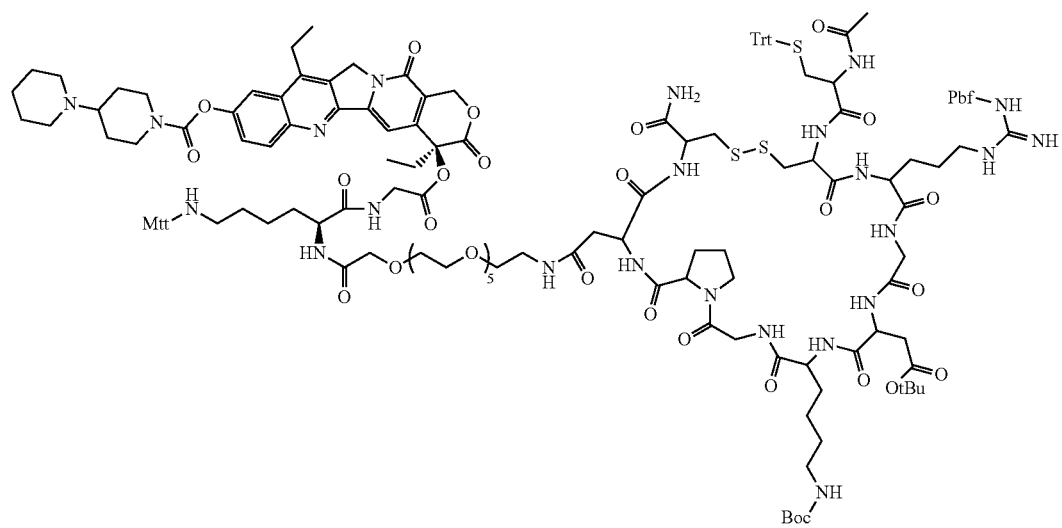
23
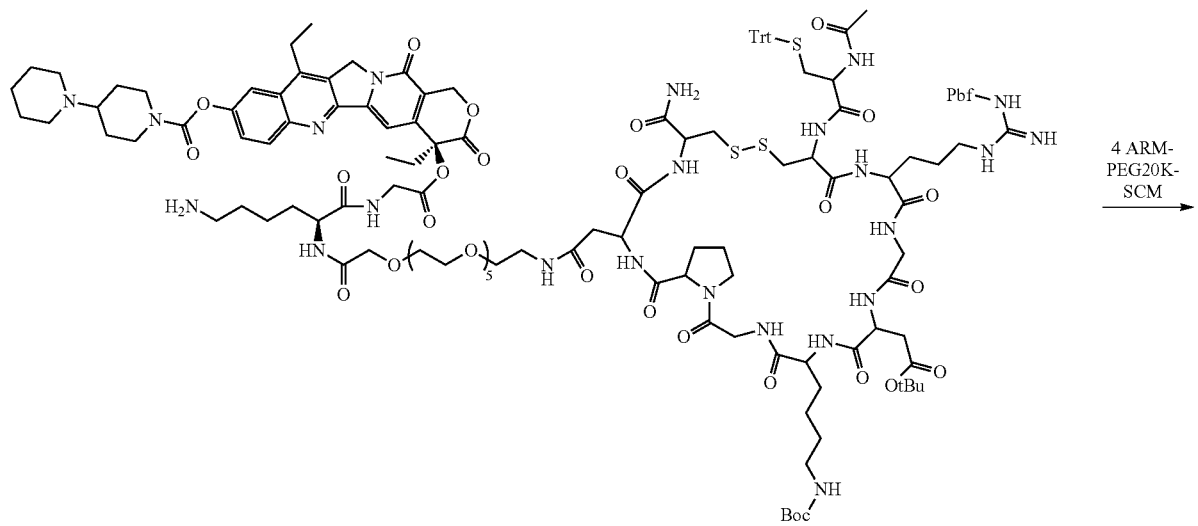
24

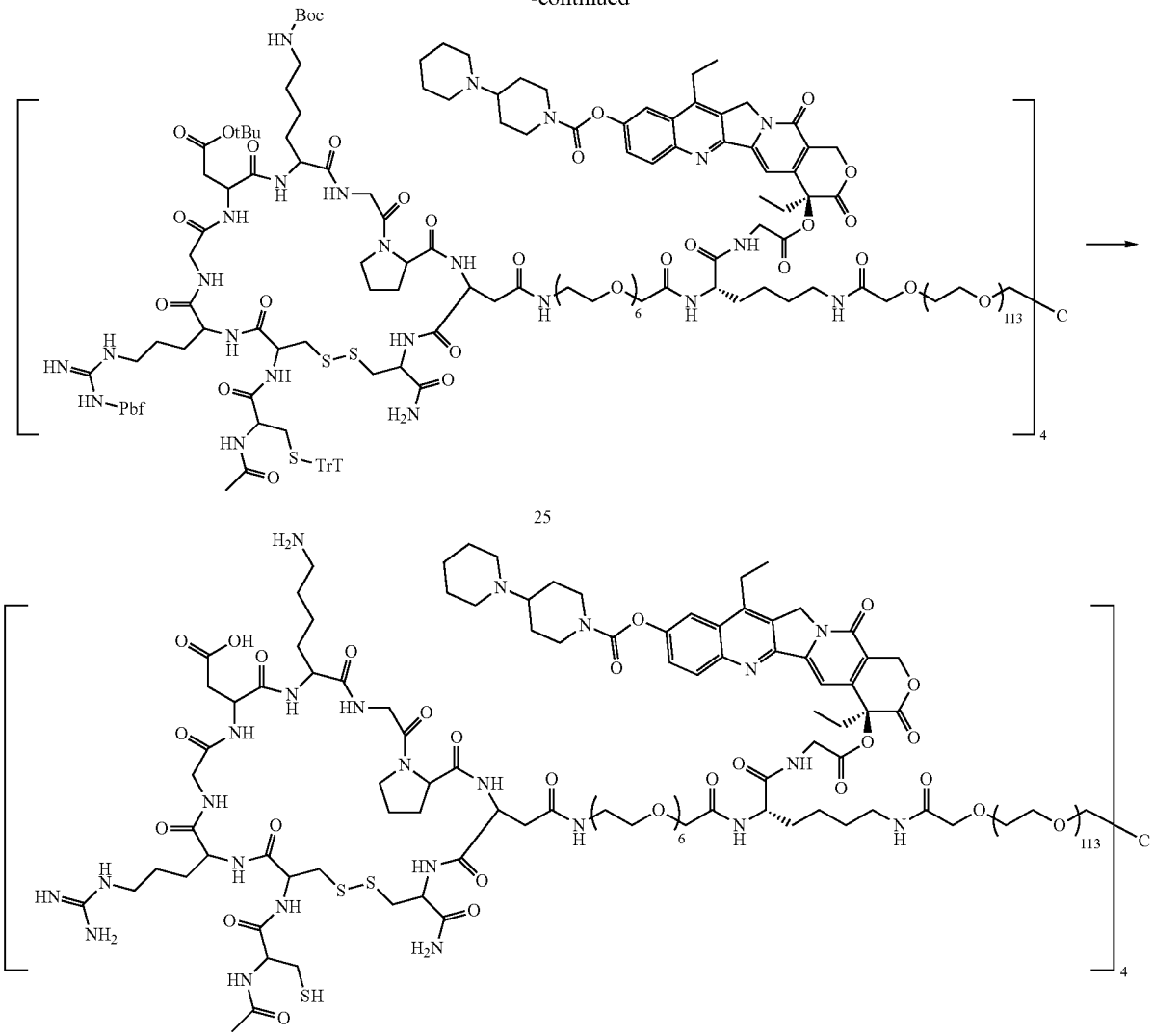

Preparation of Compound 21

To a 100 mL reaction flask, 5.00 g of Compound 20 (1.0 eq), 2.36 g of Compound 17 (1.1 eq), 50 ml of DMF, 1.11 g of DIEA (3.0 eq) and 0.71 g of DEPC (1.5 eq) were added, and the mixture was reacted at room temperature for 2 h. After the completion of the reaction was monitored by TLC, the mixture was poured into 300 mL of water, extracted twice with EA, and washed with an acetic acid aqueous solution, a sodium bicarbonate solution and a saturated sodium chloride solution. Afterwards, the mixture was dried over anhydrous sodium sulfate and concentrated to obtain 7.18 g of pale yellow solid 21, which was directly subjected to the next reaction.

Preparation of Compound 22

To a 200 mL hydrogenation reactor, 7.00 g of Compound 21, 120 mL of methanol and 0.35 g of Pd/C were added, and the mixture was subjected to hydrogenation overnight.

After the completion of the reaction was monitored by TLC, the mixture was filtered and concentrated to obtain 7.05 g of Compound 22 as a gray solid.

Preparation of Compound 23

To a 100 mL reaction flask, 7.00 g of Compound 22 (1.0 eq), 2.22 g of Compound 3 (1.05 eq), 70 mL of DMF, 1.10 g of DIEA (3.0 eq) and 0.70 g of DEPC (1.5 eq) were added, and the mixture was reacted at room temperature for 2 h. After the completion of the reaction was monitored by TLC, the mixture was poured into 700 mL of TBME and subjected to suction filtration after pulping. After the solid was dissolved in 100 mL of DCM, the mixture was poured into 1.0 L of TBME, subjected to pulping and suction filtration, and dried to obtain 8.60 g of Compound 23 as gray powder, which was directly subjected to the next reaction.

Preparation of Compound 24

8.60 g of Compound 23 was added to 200 mL of the cleavage reagent (acetic acid/TFE/DCM=1/2/7), and the reaction was carried out for 2 hours. Ice-cold MTBE was used for precipitation, and the mixture was washed, dried, and purified by HPLC to obtain 2.10 g of off-white solid 24.

Preparation of Compound 25

To a 50 mL reaction flask, 1.23 g of Compound 24 (4.5 eq), 2.00 g of 4ARM-PEG20K-SCM (1.0 eq), 20 mL of DMF and 0.09 g of TEA (9.0 eq) were added, and the mixture was reacted at room temperature. After there was no significant reaction progress monitored by HPLC, the mixture was poured into 400 mL of TBME, and subjected to pulping and suction filtration to obtain 3.05 g of Compound 25, which was directly subjected to the next reaction.

Preparation of Compound b

To a 50 mL reaction flask, 3.0 g of Compound 25 and 30 mL of the cleavage reagent (92.5% TFA/2.5% water/2.5% TIS) were added, and the mixture was stirred at room temperature for 2 h. Ice-cold MTBE was used for precipitation, and the mixture was centrifuged and washed. The crude product was desalted after being purified by reverse-phase HPLC. The organic solvent was removed by concentration, and the resultant was lyophilized to obtain 1.02 g of Compound b as off-white powder.

Preparation of Compound B

The crude product of Compound b was desalted after being purified by reverse-phase HPLC. The organic solvent was removed by concentration, pH was adjusted to 5 to 6 by dilute hydrochloric acid, and the resultant was lyophilized to obtain 1.02 g of Compound B as yellow-green powder.

The molecular weight detected by MALDI-TOF was 29013.19.

Example 11 Preparation of Compound c and Compound C

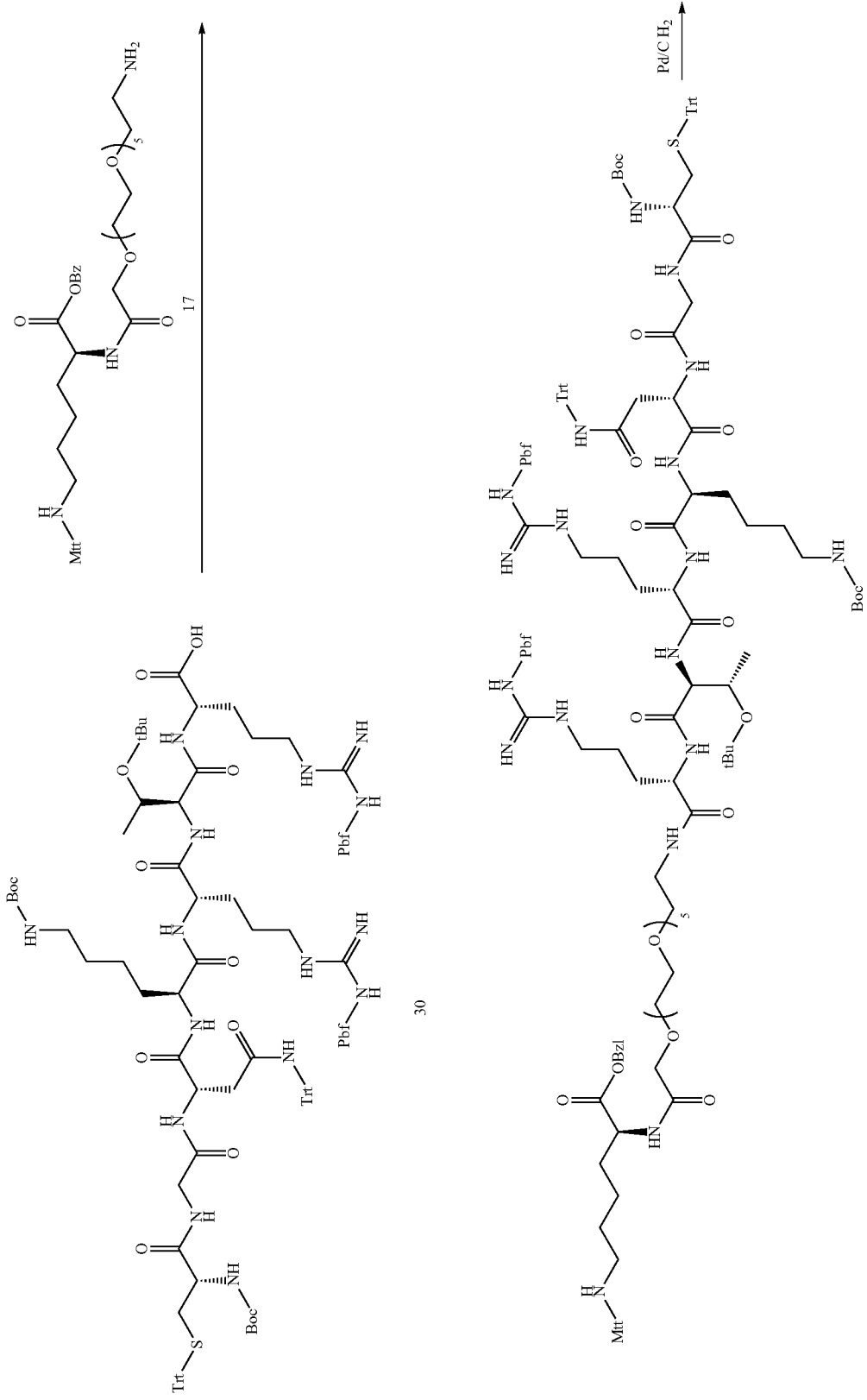

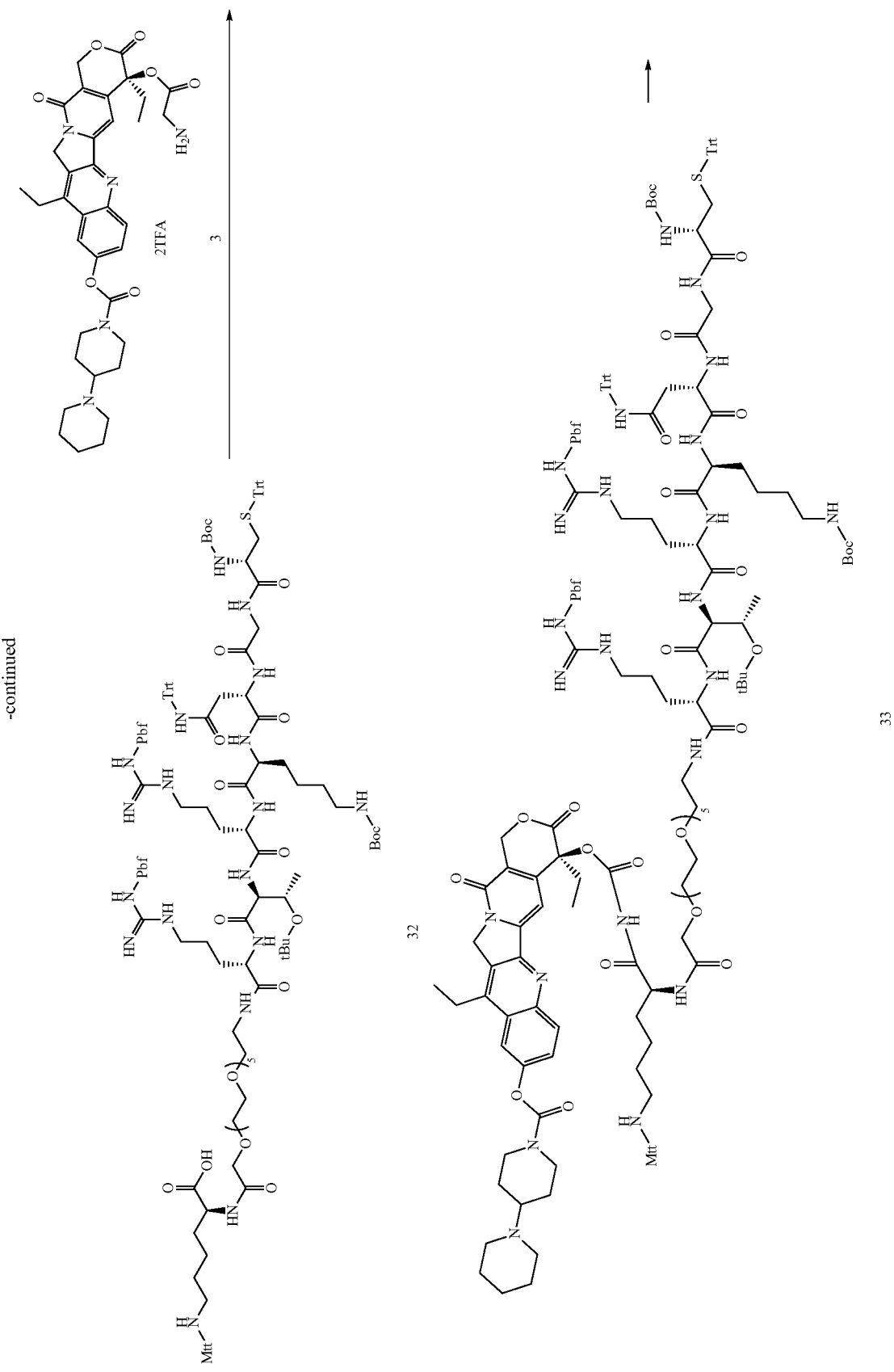

-continued
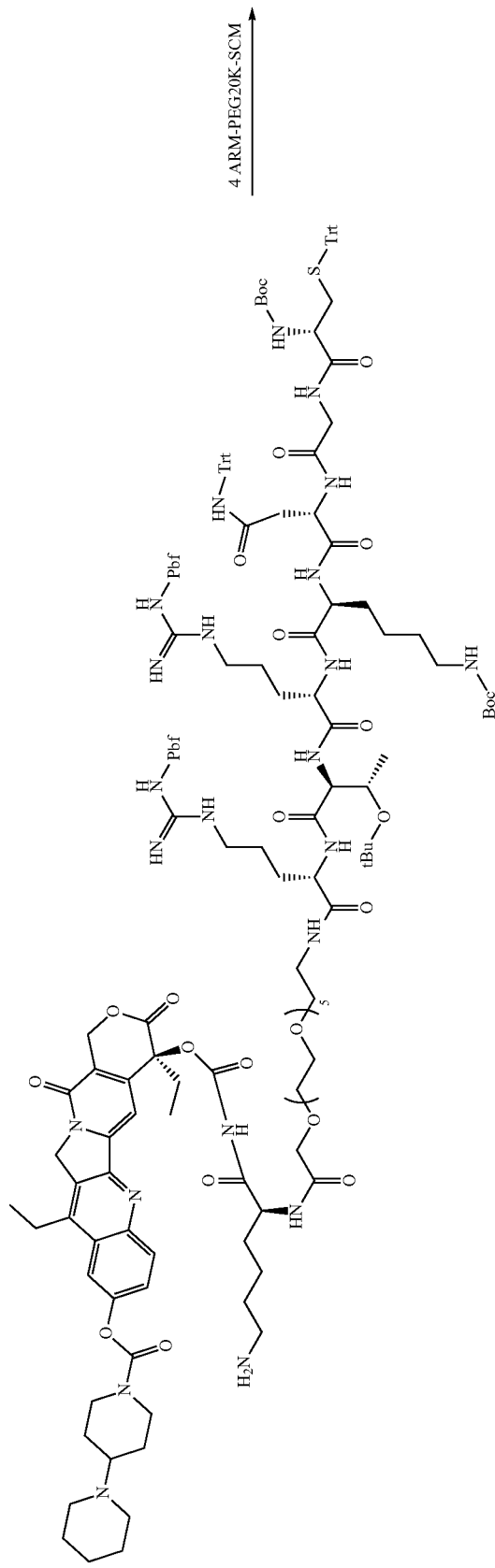

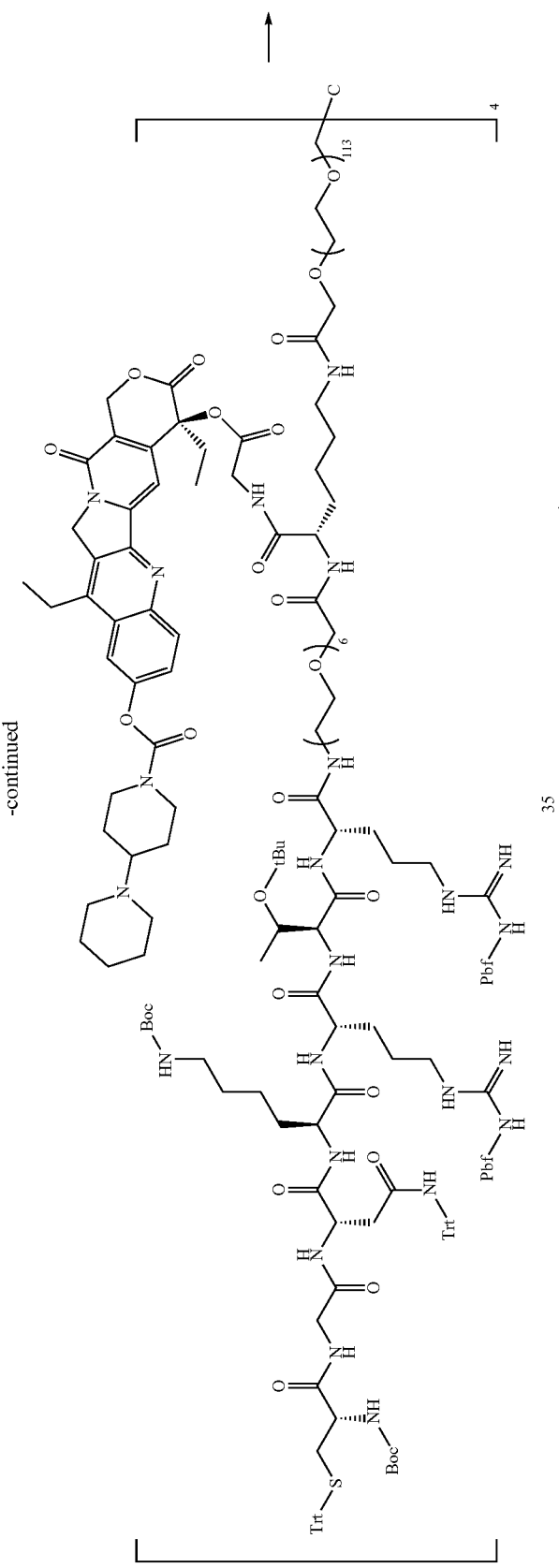
69
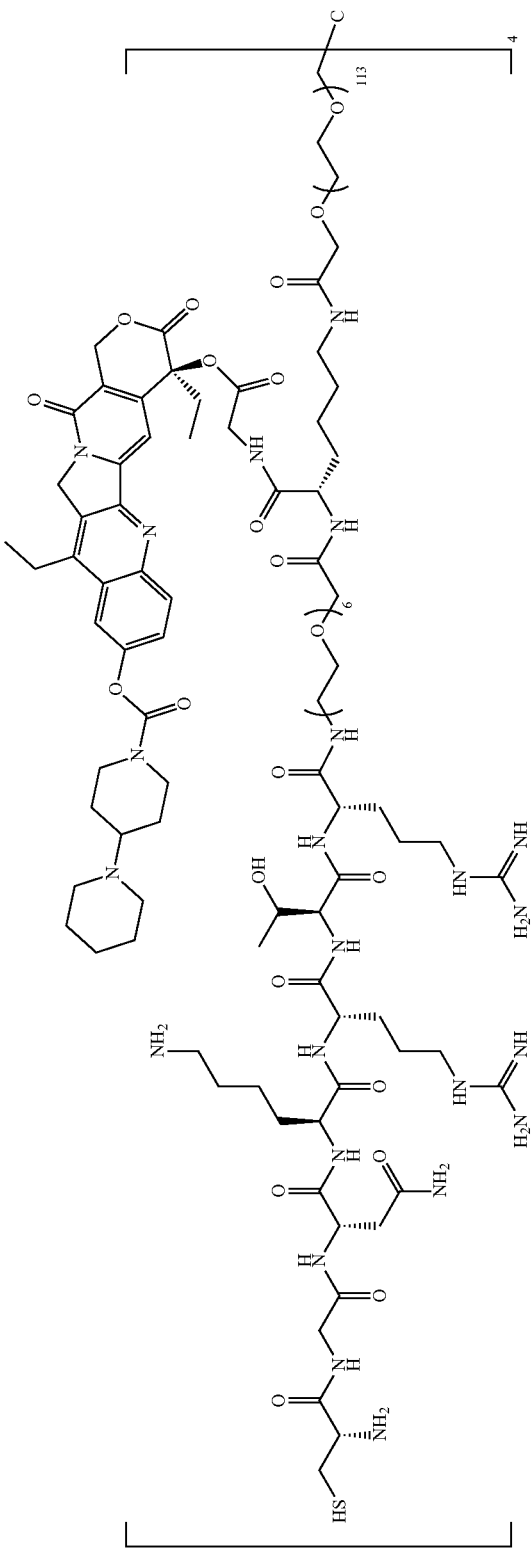
70

Preparation of Compound 31

To a 100 mL reaction flask, 5.60 g of Compound 30 (1.0 eq), 2.39 g of Compound 17 (1.1 eq), 60 mL of DMF, 1.03 g of DIEA (3.0 eq) and 0.65 g of DEPC (1.5 eq) were added, and the mixture was reacted at room temperature for 2 h. After the completion of the reaction was monitored by TLC, the mixture was poured into 300 mL of water, extracted twice with EA, and washed with an acetic acid aqueous solution, a sodium bicarbonate solution and a saturated sodium chloride solution. Afterwards, the mixture was dried over anhydrous sodium sulfate and concentrated to obtain 7.08 g of Compound 31 as a pale yellow solid, which was directly subjected to the next reaction.

Preparation of Compound 32

To a 200 mL hydrogenation reactor, 7.05 g of Compound 31, 150 mL of methanol and 0.35 g of Pd/C were added, and the mixture was subjected to hydrogenation overnight.

After the completion of the reaction was monitored by TLC, the mixture was filtered and concentrated to obtain 6.95 g of Compound 32 as a gray solid.

Preparation of Compound 33

To a 100 mL reaction flask, 6.80 g of Compound 32 (1.0 eq), 1.89 g of Compound 3 (1.05 eq), 70 mL of DMF, 0.94 g of DIEA (3.0 eq) and 0.59 g of DEPC (1.5 eq) were added, and the mixture was reacted at room temperature for 2 h. After the completion of the reaction was monitored by TLC, the mixture was poured into 700 mL of TBME and subjected to suction filtration after pulping. After the solid was dissolved in 100 mL of DCM, the mixture was poured into 1.0 L of TBME, subjected to pulping and suction filtration, and dried to obtain 8.20 g of Compound 33 as gray powder, which was directly subjected to the next reaction.

Preparation of Compound 34

8.20 g of Compound 33 was added into 160 mL of the cleavage reagent (acetic acid/TFE/DCM=1/2/7), and the reaction was carried out for 2 hours. Ice-cold MTBE was used for precipitation, and the mixture was washed, dried, and purified by HPLC to obtain 5.6 g of Compound 34 as an off-white solid.

Preparation of Compound 35

To a 50 mL reaction flask, 0.75 g of Compound 34 (4.5 eq), 1.00 g of 4ARM-PEG20K-SCM (1.0 eq), 10 mL of DMF and 0.05 g of TEA (9.0 eq) were added, and the mixture was reacted at room temperature. After there was no significant reaction progress monitored by HPLC, the mixture was poured into 200 mL of TBME, and subjected to pulping and suction filtration to obtain 1.69 g of Compound 35, which was directly subjected to the next reaction.

Preparation of Compound c

To a 50 mL reaction flask, 1.65 g of Compound 25 and 20 mL of the cleavage reagent (92.5% TFA/2.5% water/2.5% TIS) were added, and the mixture was stirred at room temperature for 2 h. Ice-cold MTBE was used for precipitation, and the mixture was centrifuged and washed. The crude product was desalted after being purified by reverse-phase HPLC. The organic solvent was removed by concentration, and the resultant was lyophilized to obtain 0.84 g of Compound c as off-white powder.

Preparation of Compound C

The crude product of Compound c was desalted after being purified by reverse-phase HPLC. The organic solvent was removed by concentration, pH was adjusted to 5 to 6 by dilute hydrochloric acid, and the resultant was lyophilized to obtain 0.84 g of Compound C as yellow-green powder.

The molecular weight detected by MALDI-TOF was 28076.21.

Example 12 Preparation of Compound d and Compound D

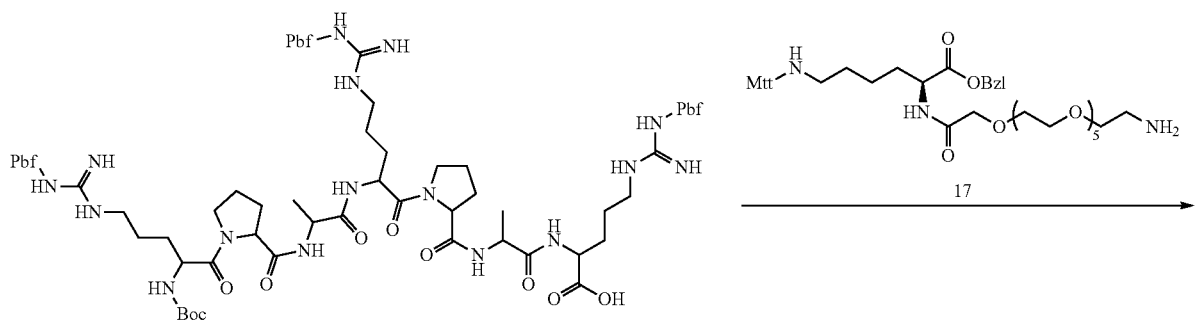

-continued
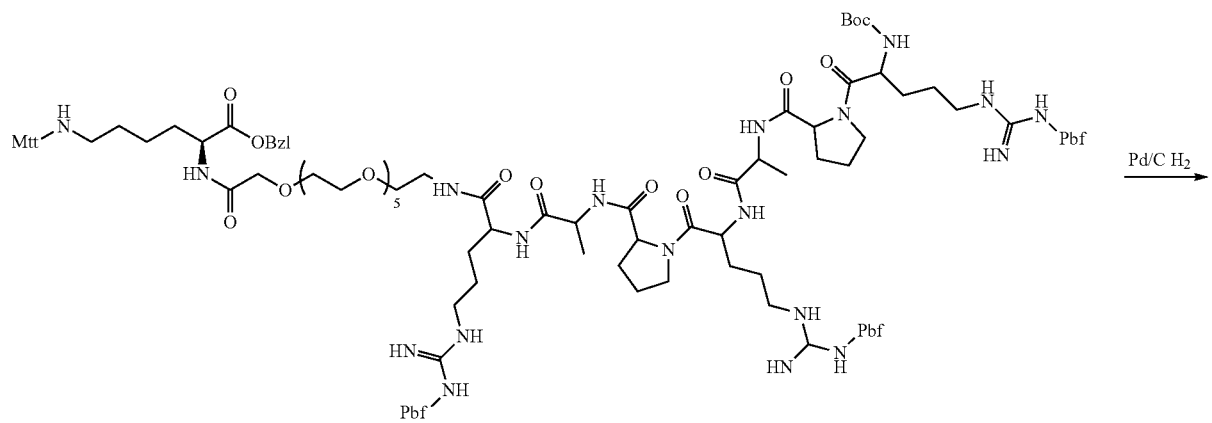
41
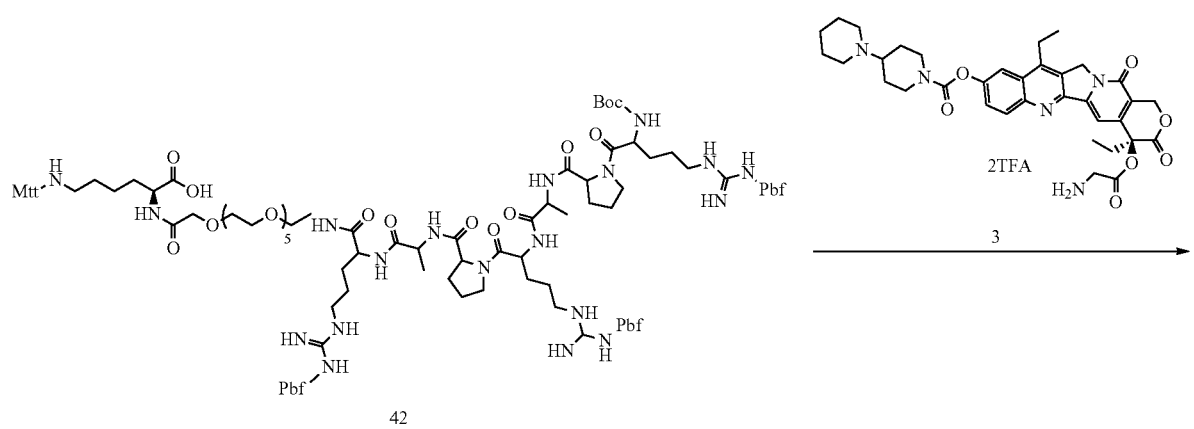
42
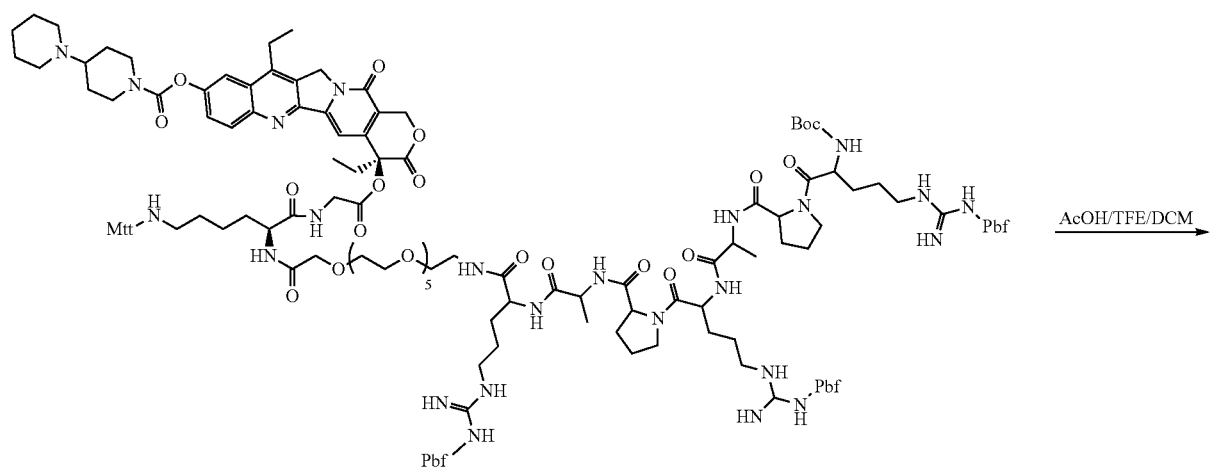
43

-continued
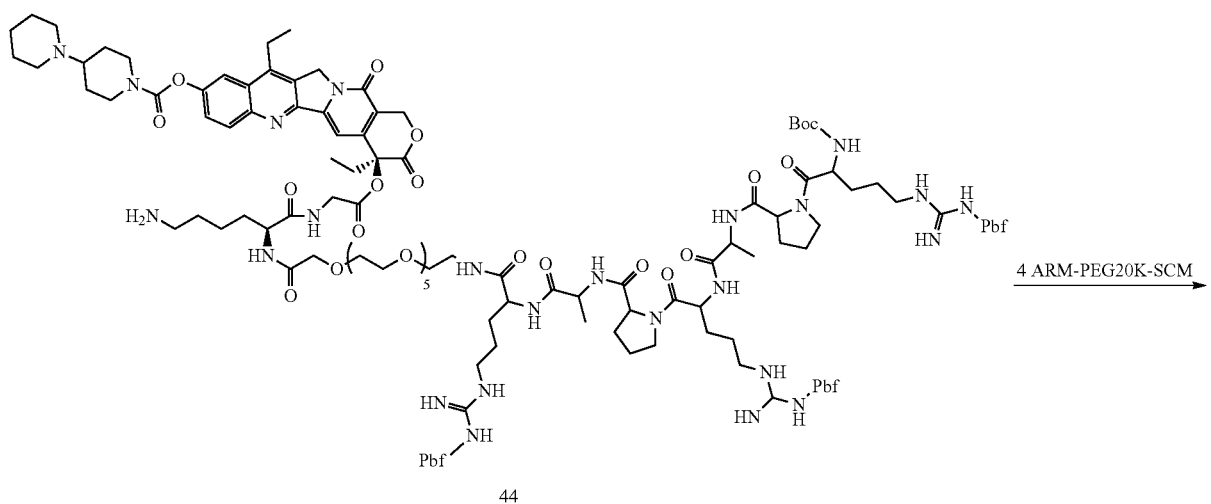
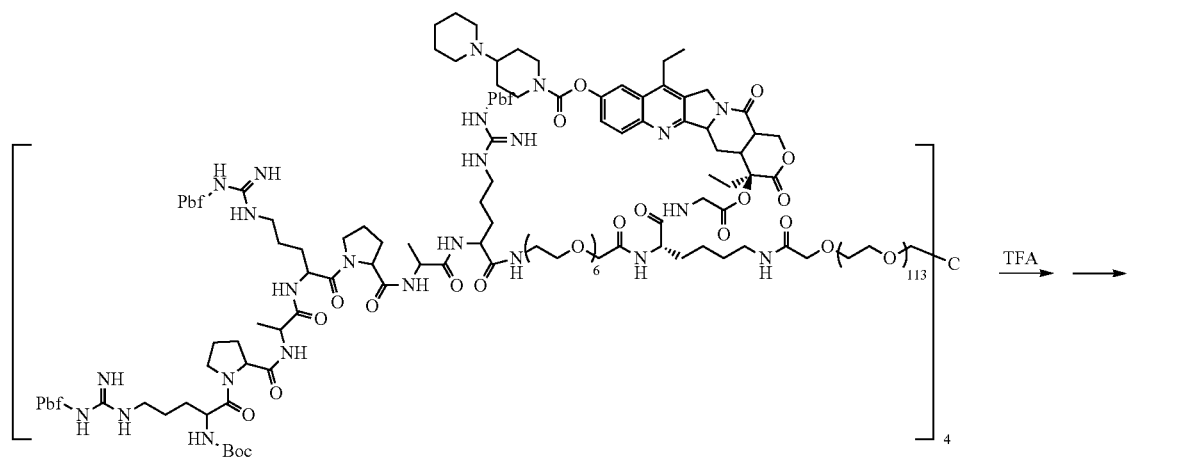
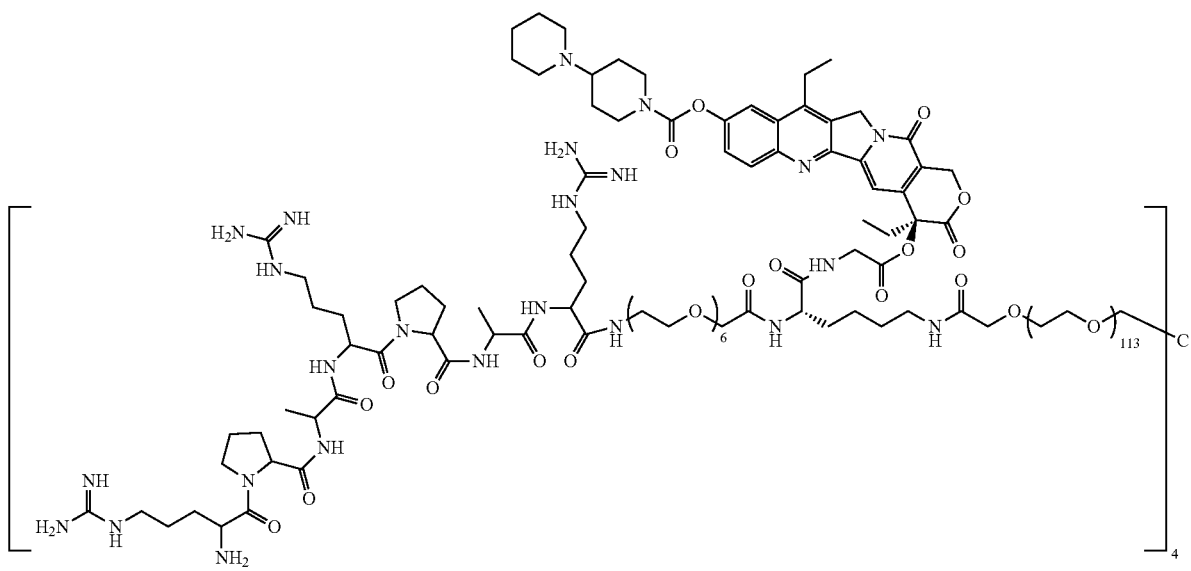

Preparation of Compound 41

To a 100 mL reaction flask, 6.20 g of Compound 40 (1.0 eq), 3.30 g of Compound 17 (1.1 eq), 62 mL of DMF, 1.43 g of DIEA (3.0 eq) and 0.90 g of DEPC (1.5 eq) were added, and the mixture was reacted at room temperature for 2 h. After the completion of the reaction was monitored by TLC, the mixture was poured into 310 mL of water, extracted twice with EA, and washed with an acetic acid aqueous solution, a sodium bicarbonate solution and a saturated sodium chloride solution. Afterwards, the mixture was dried over anhydrous sodium sulfate and concentrated to obtain 8.84 g of Compound 41 as a pale yellow solid, which was directly subjected to the next reaction.

Preparation of Compound 42

To a 200 mL hydrogenation reactor, 8.80 g of Compound 41, 150 mL of methanol and 0.44 g of Pd/C were added, and the mixture was subjected to hydrogenation overnight.

After the completion of the reaction was monitored by TLC, the mixture was filtered and concentrated to obtain 8.84 g of Compound 42 as a gray solid.

Preparation of Compound 43

To a 100 mL reaction flask, 8.50 g of Compound 42 (1.0 eq), 2.77 g of Compound 3 (1.05 eq), 85 mL of DMF, 1.38 g of DIEA (3.0 eq) and 0.87 g of DEPC (1.5 eq) were added, and the mixture was reacted at room temperature for 2 h. After the completion of the reaction was monitored by TLC, the mixture was poured into 850 mL of TBME and subjected to suction filtration after pulping. After the solid was dissolved in 110 mL of DCM, the mixture was poured into 1.1 L of TBME, subjected to pulping and suction filtration, and dried to obtain 9.86 g of Compound 43 as gray powder, which was directly subjected to the next reaction.

Preparation of Compound 44

9.80 g of Compound 43 was added to 200 mL of the cleavage reagent (acetic acid/TFE/DCM=1/2/7), and the reaction was carried out for 2 hours. Ice-cold MTBE was used for precipitation, and the mixture was washed, dried, and purified by HPLC to obtain 5.92 g of Compound 44 as an off-white solid.

Preparation of Compound 45

To a 50 mL reaction flask, 0.60 g of Compound 34 (4.5 eq), 1.00 g of 4ARM-PEG20K-SCM (1.0 eq), 10 mL of DMF and 0.05 g of TEA (9.0 eq) were added, and the mixture was reacted at room temperature. After there was no significant reaction progress monitored by HPLC, the mixture was poured into 200 mL of TBME, and subjected to pulping and suction filtration to obtain 1.45 g of Compound 45, which was directly subjected to the next reaction.

Preparation of Compound d

To a 50 mL reaction flask, 1.45 g of Compound 45 and 15 mL of the cleavage reagent (92.5% TFA/2.5% water/2.5% TIS) were added, and the mixture was stirred at room temperature for 2 h. Ice-cold MTBE was used for precipitation, and the mixture was centrifuged and washed. The crude product was desalted after being purified by reverse-phase HPLC. The organic solvent was removed by concentration, and the resultant was lyophilized to obtain 0.57 g of Compound d as off-white powder.

Preparation of Compound D

The crude product of Compound d was desalted after being purified by reverse-phase HPLC. The organic solvent was removed by concentration, pH was adjusted to 5 to 6 by dilute hydrochloric acid, and the resultant was lyophilized to obtain 0.57 g of Compound D as yellow-green powder.

The molecular weight detected by MALDI-TOF was 27963.54.

Example 13 Preparation of Compound e and Compound E

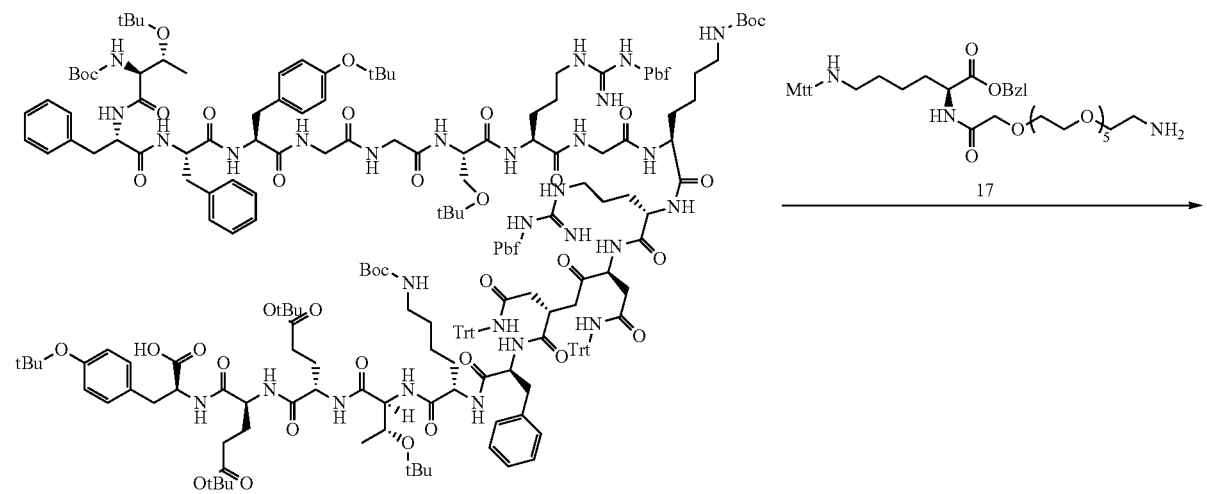

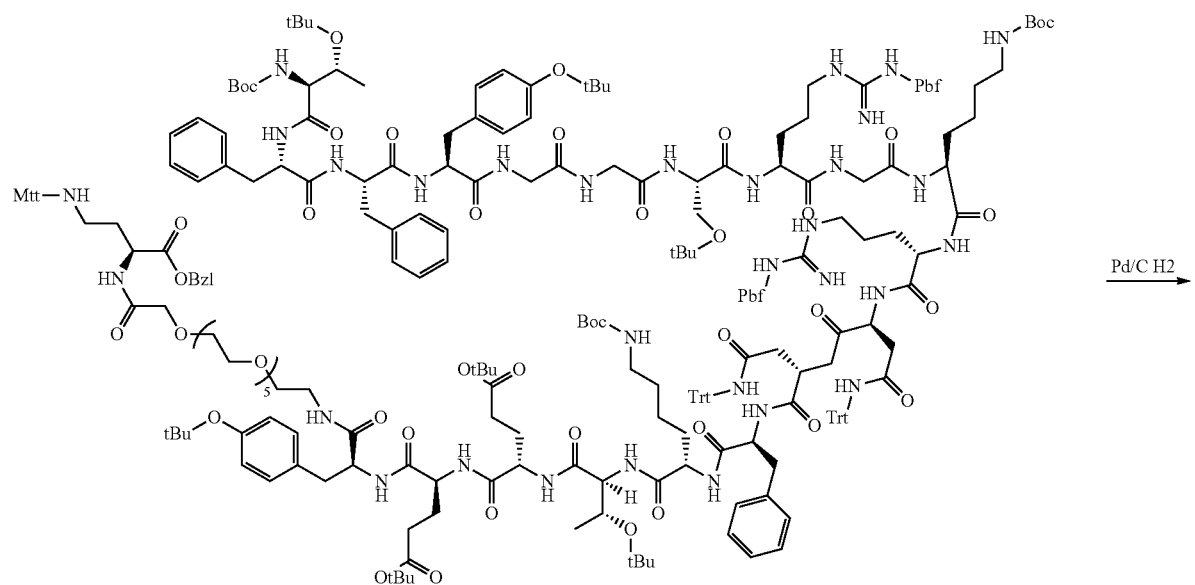
51
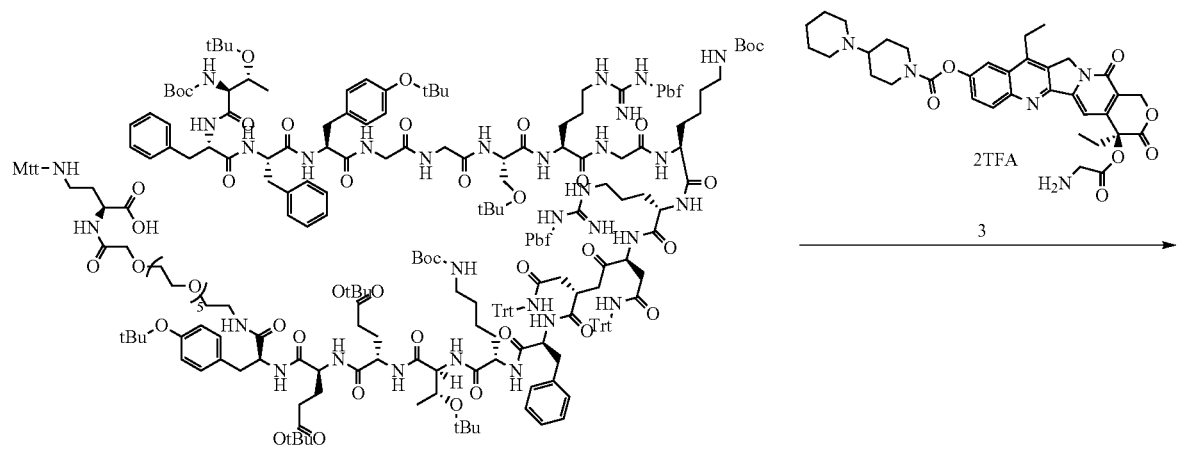
52

81
-continued
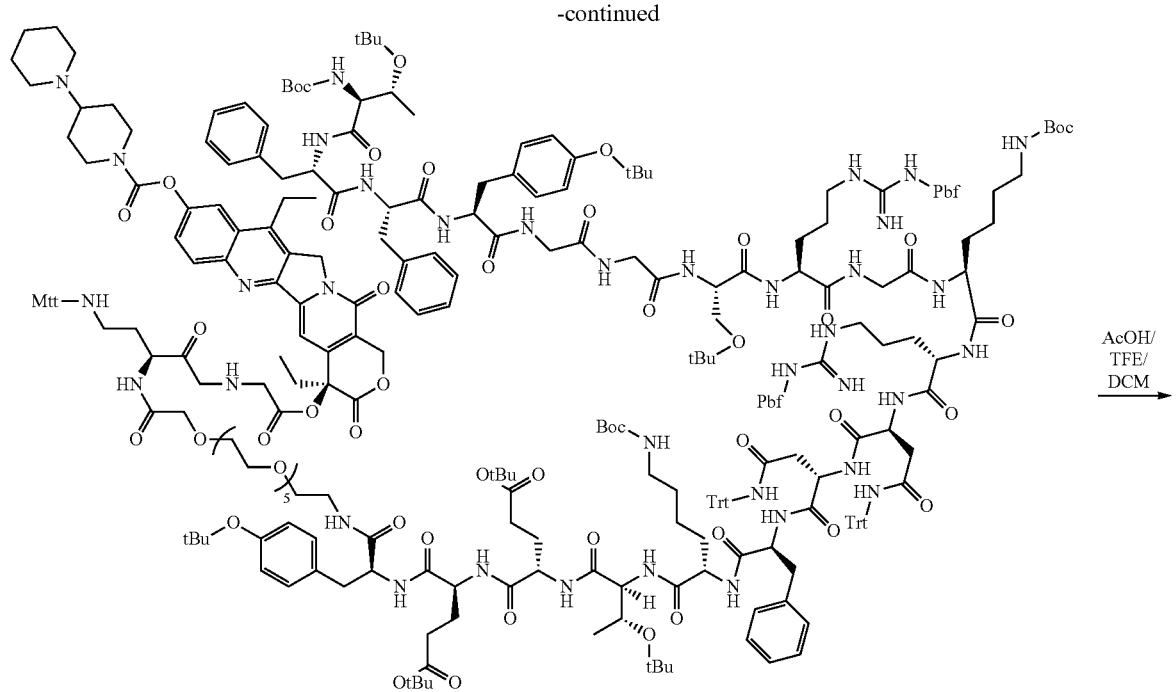
53
AcOH/
TFE/
DCM
→
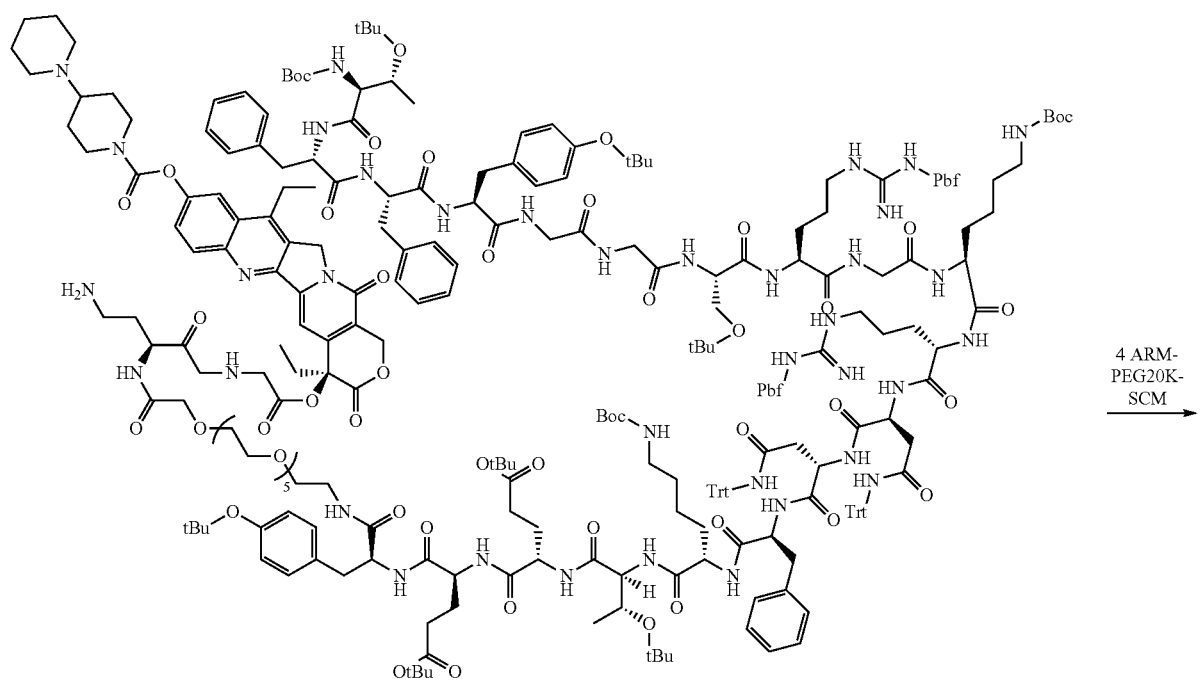
54
4 ARM-
PEG20K-
SCM
→

-continued

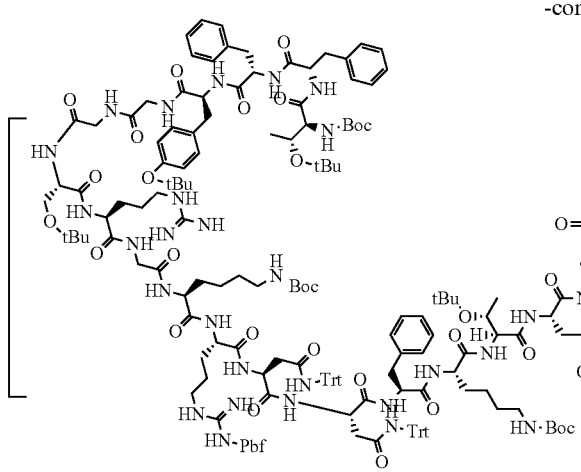
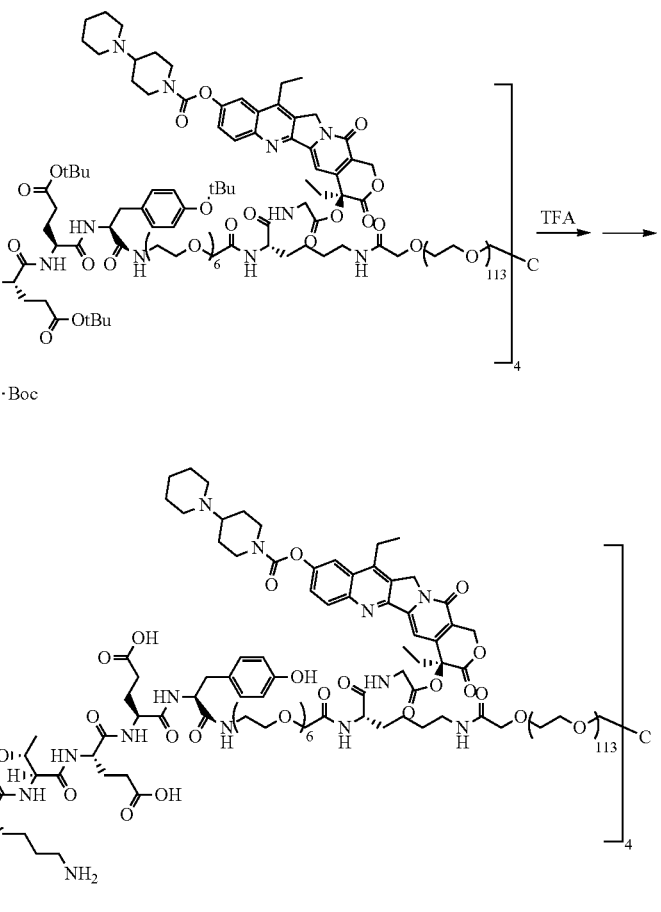

Preparation of Compound 51

To a 100 mL reaction flask, 6.20 g of Compound 50 (1.0 eq), 1.39 g of Compound 17 (1.1 eq), 62 mL of DMF, 0.60 g of DIEA (3.0 eq) and 0.38 g of DEPC (1.5 eq) were added, and the mixture was reacted at room temperature for 2 h. After the completion of the reaction was monitored by TLC, the mixture was poured into 10 mL of water, extracted twice with EA, and washed with an acetic acid aqueous solution, a sodium bicarbonate solution and a saturated sodium chloride solution. Afterwards, the mixture was dried over anhydrous sodium sulfate and concentrated to obtain 6.5 g of Compound 51 as a jelly-like solid, which was directly subjected to the next reaction.

Preparation of Compound 52

To a 200 mL hydrogenation reactor, 6.53 g of Compound 51, 150 mL of methanol and 0.33 g of Pd/C were added, and the mixture was subjected to hydrogenation overnight. After the completion of the reaction was monitored by TLC, the mixture was filtered and concentrated to obtain 6.50 g of Compound 52 as a gray solid.

Preparation of Compound 53

To a 100 mL reaction flask, 6.50 g of Compound 52 (1.0 eq), 1.08 g of Compound 3 (1.05 eq), 65 mL of DMF, 0.54 g of DIEA (3.0 eq) and 0.34 g of DEPC (1.5 eq) were added, and the mixture was reacted at room temperature for 2 h. After the completion of the reaction was monitored by TLC, the mixture was poured into 650 mL of TBME and subjected to suction filtration after pulping. After the solid was dissolved in 100 mL of DCM, the mixture was poured into 1.0 L of TBME, subjected to pulping and suction filtration, and dried to obtain 6.71 g of Compound 53 as gray powder, which was directly subjected to the next reaction.

Preparation of Compound 54

2.5 g of Compound 53 was added to 50 mL of the cleavage reagent (acetic acid/TFE/DCM=1/2/7), and the reaction was carried out for 2 hours. Ice-cold MTBE was used for precipitation, and the mixture was washed, dried, and purified by HPLC to obtain 0.97 g of Compound 54 as an off-white solid.

Preparation of Compound 55

To a 50 mL reaction flask, 2.91 g of Compound 54 (4.5 eq), 3.00 g of 4ARM-PEG20K-SCM (1.0 eq), 30 mL of DMF and 0.13 g of TEA (9.0 eq) were added, and the mixture was reacted at room temperature. After there was no significant reaction progress monitored by HPLC, the mixture was poured into 300 mL of TBME, and subjected to pulping and suction filtration to obtain 5.83 g of Compound 55, which was directly subjected to the next reaction.

Preparation of Compound e

To a 50 mL reaction flask, 2.04 g of Compound 55 and 30 mL of the cleavage reagent (92.5% TFA/2.5% water/2.5% TIS) were added, and the mixture was stirred at room temperature for 2 h. Ice-cold MTBE was used for precipitation, and the mixture was centrifuged and washed. The crude product was desalted after being purified by reverse-phase HPLC. The organic solvent was removed by concentration, and the resultant was lyophilized to obtain 0.42 g of off-white powder e. -

Preparation of Compound E

The crude product of Compound e was desalted after being purified by reverse-phase HPLC. The organic solvent was removed by concentration, pH was adjusted to 5 to 6 by dilute hydrochloric acid, and the resultant was lyophilized to obtain 0.42 g of yellow-green powder E.

The molecular weight detected by MALDI-TOF was 33812.65.

Example 14 Preparation of Compound f and Compound F

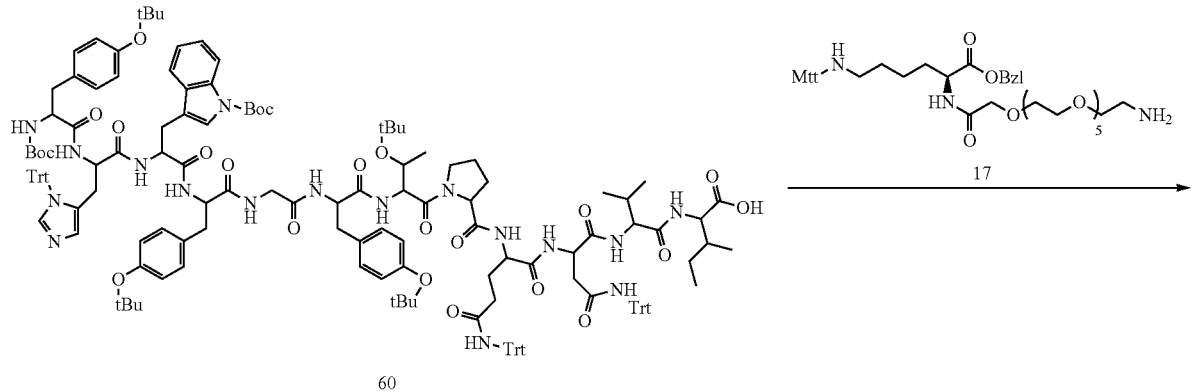

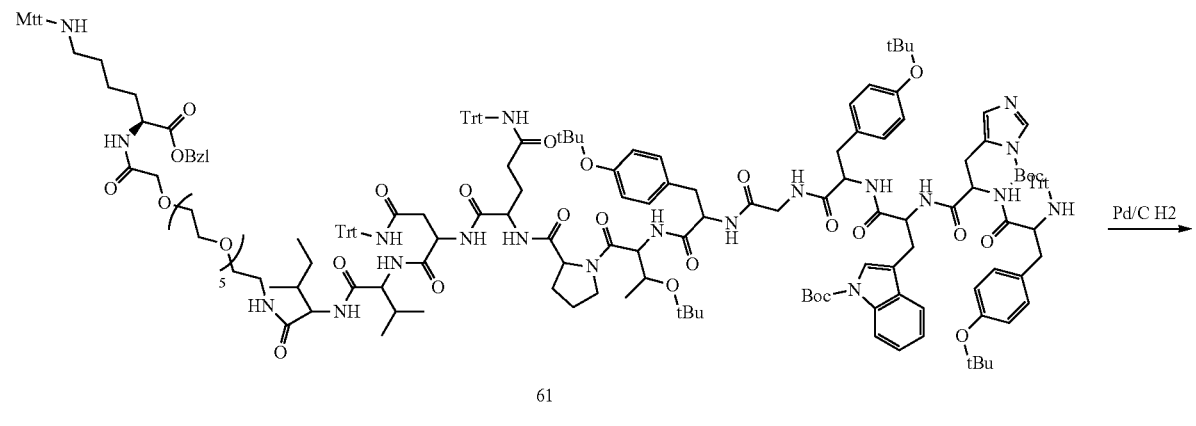

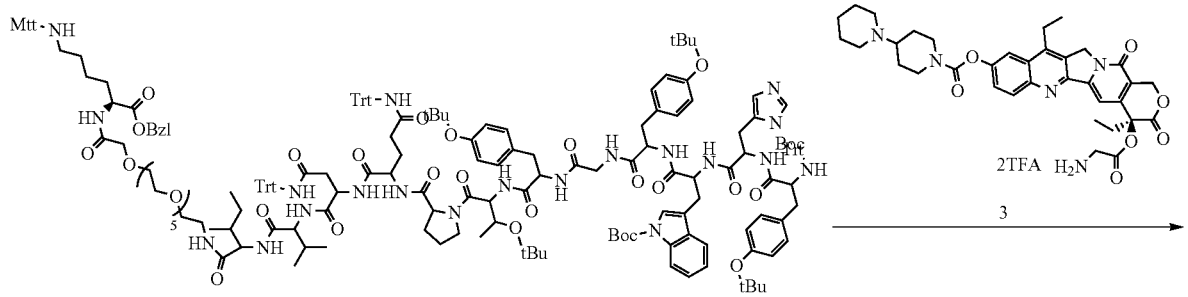

-continued
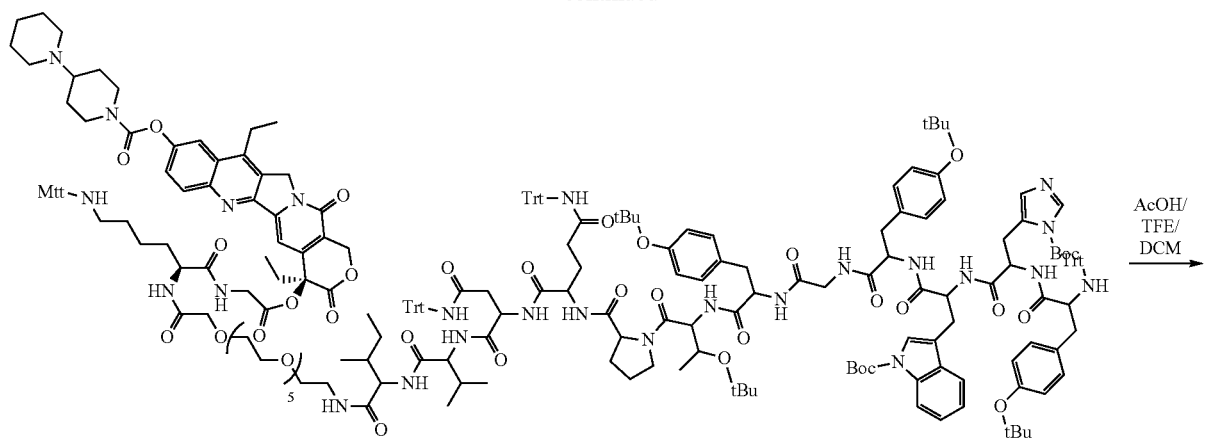
63
AcOH/
TFE/
DCM
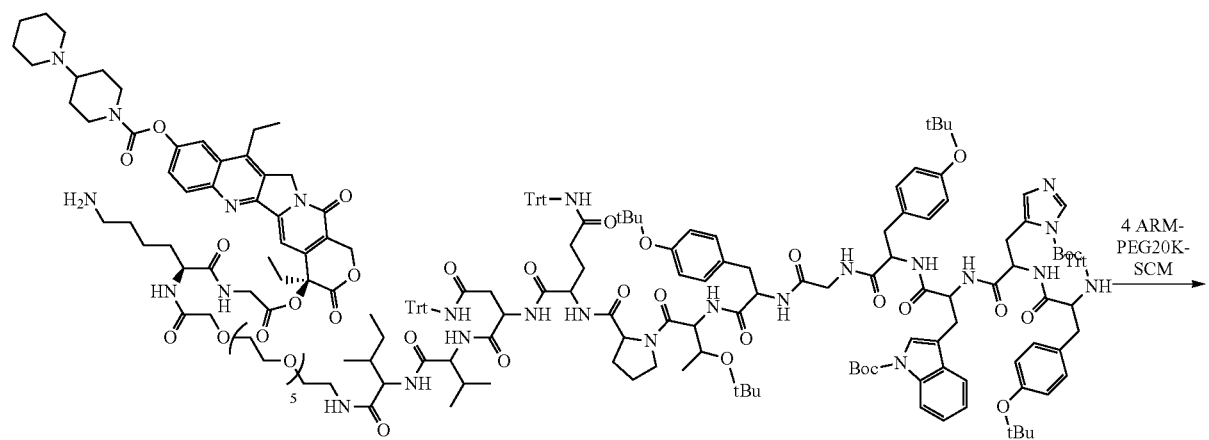
64
4 ARM-
PEG20K-
SCM
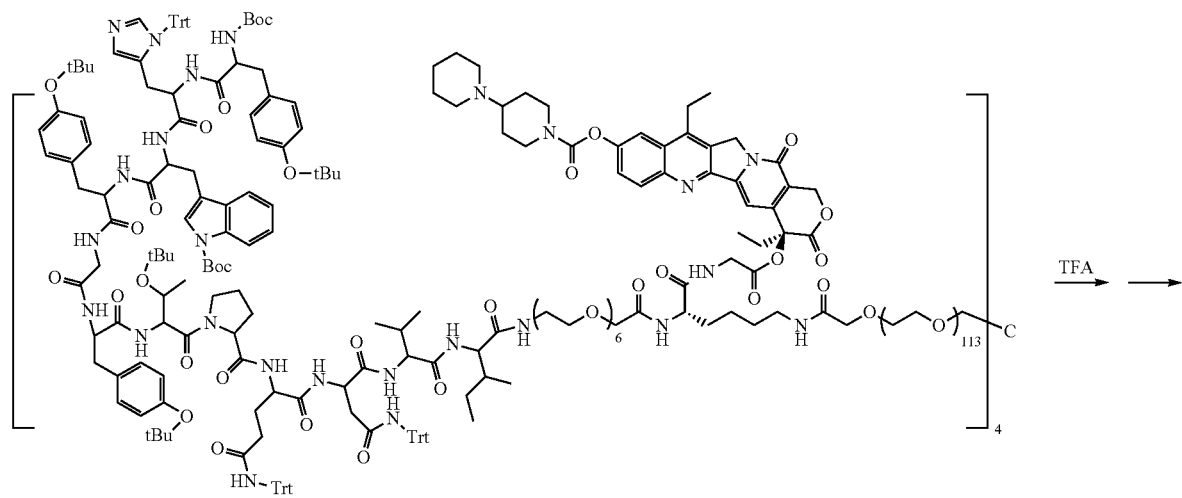
65
TFA -continued

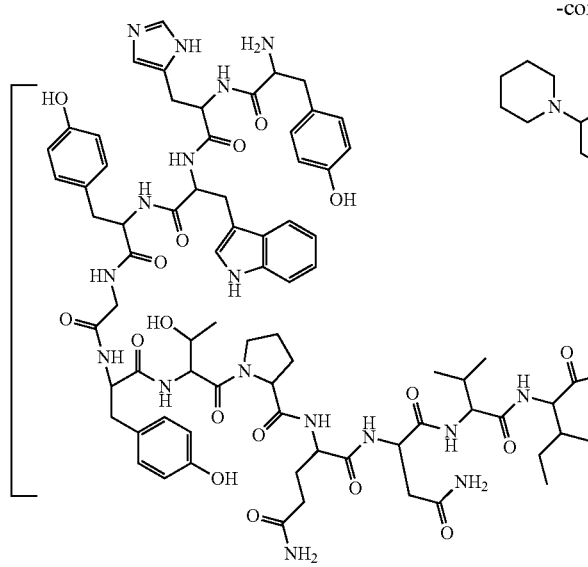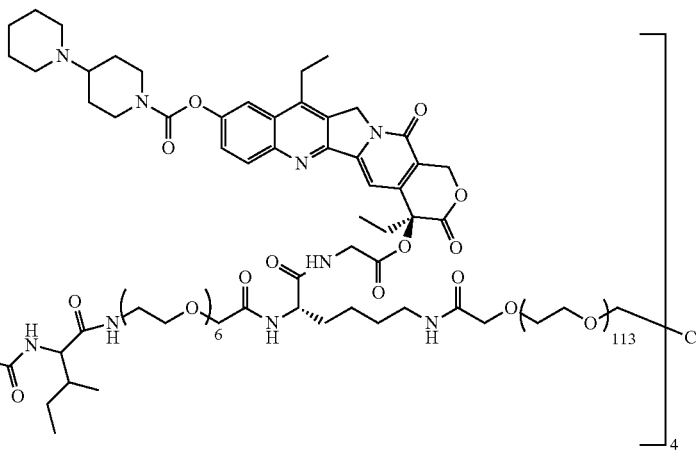

Preparation of Compound 61

To a 100 mL reaction flask, 5.00 g of Compound 60 (1.0 eq), 1.66 g of Compound 17 (1.1 eq), 50 mL of DMF, 0.72 g of DIEA (3.0 eq) and 0.45 g of DEPC (1.5 eq) were added, and the mixture was reacted at room temperature for 2 h. After the completion of the reaction was monitored by TLC, the mixture was poured into 10 mL of water, extracted twice with EA, and washed with an acetic acid aqueous solution, a sodium bicarbonate solution and a saturated sodium chloride solution. Afterwards, the mixture was dried over anhydrous sodium sulfate and concentrated to obtain 6.14 g of a jelly-like solid 61, which was directly subjected to the next reaction.

Preparation of Compound 62

To a 200 mL hydrogenation reactor, 6.10 g of Compound 61, 150 mL of methanol and 0.31 g of Pd/C were added, and the mixture was subjected to hydrogenation overnight. After the completion of the reaction was monitored by TLC, the mixture was filtered and concentrated to obtain 5.98 g of Compound 62 as a gray solid.

Preparation of Compound 63

To a 100 mL reaction flask, 5.95 g of Compound 62 (1.0 eq), 1.36 g of Compound 3 (1.05 eq), 60 mL of DMF, 0.68 g of DIEA (3.0 eq) and 0.43 g DEPC (1.5 eq) were added, and the mixture was reacted at room temperature for 2 h. After the completion of the reaction was monitored by TLC, the mixture was poured into 600 mL of TBME and subjected to suction filtration after pulping. After the solid was dissolved in 100 mL of DCM, the mixture was poured into 1.0 L of TBME, subjected to pulping and suction filtration, and dried to obtain 6.53 g of Compound 63 as gray powder, which was directly subjected to the next reaction.

Preparation of Compound 64

6.50 g of Compound 63 was added to 130 mL of the cleavage reagent (acetic acid/TFE/DCM=1/2/7), and the reaction was carried out for 2 hours. Ice-cold MTBE was used for precipitation, and the mixture was washed, dried, and purified by HPLC to obtain 3.63 g of Compound 64 as an off-white solid.

Preparation of Compound 65

To a 50 mL reaction flask, 2.06 g of Compound 64 (4.5 eq), 3.00 g of 4ARM-PEG20K-SCM (1.0 eq), 30 mL of DMF and 0.13 g of TEA (9.0 eq) were added, and the mixture was reacted at room temperature. After there was no significant reaction progress monitored by HPLC, the mixture was poured into 300 mL of TBME, and subjected to pulping and suction filtration to obtain 4.67 g of Compound 65, which was directly subjected to the next reaction.

Synthesis of Compound f

To a 200 mL reaction flask, 4.60 g of Compound 65 and 100 mL of the cleavage reagent (92.5% TFA/2.5% water/2.5% TIS) were added, and the mixture was stirred at room temperature for 2 h. Ice-cold MTBE was used for precipitation, and the mixture was centrifuged and washed. The crude product was desalted after being purified by reverse-phase HPLC. The organic solvent was removed by concentration, and the resultant was lyophilized to obtain 1.34 g of Compound f as off-white powder.

Synthesis of Compound F

The crude product of Compound f was desalted after being purified by reverse-phase HPLC. The organic solvent was removed by concentration, pH was adjusted to 5 to 6 by dilute hydrochloric acid, and the resultant was lyophilized to obtain 1.34 g of Compound F as yellow-green powder.

The molecular weight detected by MALDI-TOF was 30907.82.

The sources of the test articles, reagents, instruments, and the like which were used in Examples 15 to 19 of the present disclosure were as follows.

Irinotecan (bulk drug) was obtained by purchasing.

As for the preparation method of nktr-102, the method disclosed in CN102711837A was referred and the method was as follows.

Compound 3 (829 mg, 4.5 eq) in Example 1 was added to a 250 mL reaction flask, and DCM (50 mL) and triethylamine (221 mg, 9.0 eq) were added. After the mixture was dissolved, 4ARM-PEG20K-SCM (5.00 g, 1.0 eq) was added to this reaction flask. After there was no significant reaction progress monitored by HPLC, about 20 mL of DCM was distilled off under reduced pressure. The solution was poured into 300 mL of TBME, stirred, and subjected to precipitation and filtration, so as to obtain 5.4 g of crude product. The crude product was purified by HPLC and desalted. pH was adjusted to 5 to 6 by dilute hydrochloric acid, and the resultant was lyophilized to obtain 2.71 g of nktr-102 as pale green powder.

Physiological saline was purchased from Shanghai Huayuan Changfu Pharmaceutical (Group) Co., Ltd. 1 mL sterile syringes were purchased from Shanghai Kindly Enterprise Development Group Co., Ltd (Shanghai, China). MDA-MB-231 cells were cultured in DMEM culture medium (GIBCO, USA) containing 10% fetal bovine serum FBS (GIBCO, USA), and cultured in a 37° C. incubator containing 5% $CO_2$. Matrigel (BD Matrigel) was purchased from Becton, Dickinson and Company (BD, USA).

Biosafe cabinet (model: AC2-6E1) was purchased from ESCO; water-jacketed $CO_2$ cell incubator (model: 3111) was purchased from Thermo Scientific Forma; the inverted microscope (model: CKX41SF) was purchased from Olympus; electric suction apparatus (model: YX930D) was purchased from Shanghai Medical Instruments (Group) Co., Ltd.; balance (METTLER-TOLEDO AB135-S) was purchased from METTLER-TOLEDO; the low speed centrifuge (model: LD5-2A) was purchased from Beijing Lab Centrifuge Co., Ltd.; and digimatic caliper (model: SF2000) was purchased from Guilin Guanglu Measuring Instrument Co., Ltd.

In Examples 15 to 19 of the present disclosure, the operation of all animal experiments strictly adhered to the principles of the use and management of animals. For the calculation of the tumor-related parameters, "Technical guidelines for non-clinical research on cytotoxic antitumor drugs" by Chinese CFDA was referred. According to "Technical guidelines for non-clinical research on cytotoxic antitumor drugs" (November, 2006) by Chinese SFDA, the treatment was considered to be effective when % T/C≤40% and P<0.05 according to statistical analysis.

The calculation formula of the tumor volume (TV) was as follows: TV $(mm^3) = l \times w^2 / 2$ wherein l represented the long diameter of a tumor (mm), and w represented the short diameter of a tumor (mm).

The calculation formula of the relative tumor volume (RTV) was: $RTV = TV_t / TV_{initial}$ wherein $TV_{initial}$ was the tumor volume measured at the time of grouping and the first administration, and $TV_t$ was the tumor volume at each measurement during administration.

The calculation formula of the relative tumor proliferation rate (% T/C) was: % T/C=100%×($RTV_T / RTV_C$)

wherein $RTV_T$ represented the RTV of a treatment group, and $RTV_C$ represented the RTV of the solvent control group.

The calculation formula of the tumor growth inhibition rate (TGI (%)) was: TGI=100%×[1−($TV_{t(T)} - TV_{initial(T)}$)/($TV_{t(C)} - TV_{initial(C)}$)]

wherein $TV_{t(T)}$ represented the tumor volume of a treatment group at each measurement, $TV_{initial(T)}$ represented the tumor volume of a treatment group measured at the time of grouping and the first administration, $TV_{t(C)}$ represented the tumor volume of the solvent control group at each measurement, and $TV_{initial(C)}$ represented the tumor volume of the solvent control group measured at the time of grouping and the first administration.

The calculation formula of the decline rate of animal body weight was: decline rate of animal body weight=100%× ($BW_{initial} - BW_t$)/$BW_{initial}$ wherein $BW_t$ represented the animal body weight at each measurement during administration, and $BW_{initial}$ represented the animal body weight at the time of grouping and the first administration.

The calculation formula of the tumor weight inhibition rate (IR (%)) was: IR (%)=100%×($W_C - W_T$)/$W_C$ wherein $W_C$ represented the tumor weight of the control group, and $W_T$ represented the tumor weight of a treatment group.

The experimental data was subjected to calculation and related statistical treatments using Microsoft Office Excel 2007 Software. Unless otherwise specified, the data was represented by mean±standard error (Mean±SE), t-test was adopted for the comparison between groups, and P<0.05 was considered as having significant difference.

Example 15 In Vivo Efficacy Evaluation of a Series of Compounds in a Human Colon Cancer HT-29 Cell Strain Transplanted Tumor Model in Nude Mice Test articles: irinotecan, nktr-102, and 12 compounds of the present disclosure.

Reagents: McCoy's 5A liquid culture medium, fetal bovine serum (FBS), trypsin, penicillin-streptomycin, water for injection, physiological saline, lactic acid, and sorbitol.

Experimental animals: Female BALB/c nude mice (number of animals: 150; weeks of age: 6 to 7 weeks old) were purchased from Beijing Vital River Laboratory Animal Technology Co., Ltd., and housed in an SPF animal room. The temperature was 20° C. to 25° C., the relative humidity was 40% to 70%, and the light and dark were respectively 12 hours. The animals had free access to water and food. After about one week of normal feeding, upon a veterinary inspection, mice with good physical signs and conditions could be selected for this experiment. A marking pen was used to mark the base of the tails of the animals before the grouping, and each animal was marked by ear clipping after the grouping.

Transplantable tumor cell line: Human colon cancer cell HT-29, derived from Cell Bank of Committee on Type Culture Collection of Chinese Academy of Science (CAS, stored frozen in liquid nitrogen in the laboratory).

Culture of HT-29 cells: Under a culture condition of 5% $CO_2$ and 37° C., HT-29 cells were subjected to conventional cell cultivation in an McCoy's 5A liquid culture medium containing 10% fetal bovine serum, digested with 0.25% trypsin, and passaged. According to the condition of cell growth, the cells were passaged 2 to 3 times every week, and were passaged in a ratio of 1:4 to 1:6.

Preparation of the animal model: HT-29 cells in logarithmic phase of growth were collected. The cells were resuspended in an McCoy's 5A culture medium free of serum after being counted, and the concentration of the cells was adjusted to $4 \times 10^7$ cells/mL. The cells were charged into a 50 mL centrifuge tube after being pipetted with a pipettor to make them evenly dispersed, and the centrifuge tube was placed in an ice box. Cell suspension was aspirated with a 1 mL syringe, and injected subcutaneously to the anterior right armpit of the nude mice. Each animal was inoculated with 100 μL ($4 \times 10^6$ cells/animal), and an HT-29 transplanted tumor model in nude mice was established. Animal status and the condition of tumor growth were observed regularly after inoculation, an electronic vernier caliper was used to measure the tumor diameters, the data was directly input to an Excel spreadsheet, and the tumor volumes were calculated. When the tumor volumes reached 100 $mm^3$ to 300 $mm^3$, 90 animals with good health condition and similar tumor volumes were selected and divided into 15 groups (n=6) using randomized block method. The tumor diameters were measured twice a week after the initiation of the experiment, the tumor volumes were calculated, and the body weights of the animals were weighed and recorded at the same time.

Preparation of the solvent: 0.5 g of sorbitol was weighed and charged into a 50 mL centrifuge tube, 50 mL of water for injection was added to the centrifuge tube, and the solid substance was dissolved completely by vortexing, so that an aqueous sorbitol solution with a concentration of 1% (w/v) was formulated and stored in a refrigerator at 4° C. until use.

Preparation of the dosing formulation of irinotecan: 12.0 mg of irinotecan was weighed, 0.15 mL of 1% lactic acid was added, the drug was dissolved completely by vortexing, and 2.85 mL of 1% aqueous sorbitol solution was then added respectively. The mixture was mixed evenly by vortexing, and the ratio of 1% lactic acid to 1% aqueous sorbitol solution was approximately 5:95 (v/v) in the solution. The effective concentration of irinotecan in the solution was 4.0 mg·mL$^{-1}$.

Preparation of the dosing formulation of nktr-102: Before each administration, 101.5 mg of nktr-102 was weighed accurately, 2.5 mL of physiological saline was added, the drug was dissolved completely by vortexing, and the effective concentration of nktr-102 in the solution was 4.0 mg·mL$^{-1}$.

Preparation of the dosing formulations of the compounds of the present disclosure: Before each administration, 120.3 mg of Compound a and Compound A, 137.0 mg of Compound b and Compound B, 132.6 mg of Compound c and Compound C, 132.0 mg of Compound d and Compound D, 159.6 mg of Compound e and Compound E, and 145.9 mg of Compound f and Compound F were respectively weighed accurately. 2.5 mL of physiological saline was added, and the drug was dissolved completely by vortexing and sonication (if needed). The effective concentration of the compounds of the present disclosure in the solution was 4.0 mg·mL$^{-1}$.

Grouping of animals and dosage regimens: The first administration was initiated on the day of grouping, the experiment was ended after about 21 days, and the volumes of administration were all 10 mL·kg$^{-1}$. The equivalent effective doses of irinotecan were all 40 mg·kg$^{-1}$. Group 1 was a solvent control group, and physiological saline was administered by intravenous injection via tail once every 4 days for a total of 3 times (Q4D×3). Groups 2 to 15 were respectively given the following test samples by intravenous injection via tail once every 4 days, Q4D×3: irinotecan, nktr-102, Compound a, Compound A, Compound b, Compound B, Compound c, Compound C, Compound d, Compound D, Compound e, Compound E, Compound f, and Compound F.

On the last day of the experiment, the animals were euthanized (CO$_2$) after the body weights were weighed and the tumor diameters were measured. The tumor tissues were excised and weighed. As for the human cancer xenograft models, the relative tumor proliferation rate (% T/C) was recommended to be adopted as the evaluation index of the experiment. Lower relative tumor proliferation rate indicated better tumor inhibitory effect, and the results were as shown in Table 1.

TABLE 1

Relative tumor proliferation rate (% T/C)

| Group | Sample | Number of animals | Relative tumor volume (RTV) | Relative tumor proliferation rate (% T/C) |
|---|---|---|---|---|
| 1 | blank solvent | 6 | 15.04 | — |
| 2 | irinotecan | 6 | 9.52 | 69% |
| 3 | nktr-102 | 6 | 5.23 | 34.70% |
| 4 | Compound a | 6 | 2.57* | 17.08%$^\#$ |
| 5 | Compound A | 6 | 2.55* | 16.95%$^\#$ |
| 6 | Compound b | 6 | 3.00* | 20.01%$^\#$ |
| 7 | Compound B | 6 | 2.91* | 19.41%$^\#$ |
| 8 | Compound c | 6 | 3.18* | 21.29%$^\#$ |
| 9 | Compound C | 6 | 3.18* | 21.29%$^\#$ |
| 10 | Compound d | 6 | 2.69* | 17.98%$^\#$ |
| 11 | Compound D | 6 | 2.76* | 18.45%$^\#$ |
| 12 | Compound e | 6 | 3.40* | 22.70%$^\#$ |
| 13 | Compound E | 6 | 3.43* | 22.90%$^\#$ |
| 14 | Compound f | 6 | 3.71* | 24.73%$^\#$ |
| 15 | Compound F | 6 | 3.56* | 23.73%$^\#$ |

*$P < 0.05$, as compared with the RTV of the blank solvent group, irinotecan group and nktr-102 group.
$^\#P < 0.05$, as compared with % T/C of the blank solvent group, irinotecan group and nktr-102 group.

The experimental results showed that the compounds of the present disclosure had good inhibitory effects on in vivo tumor growth in the human colon cancer HT-29 transplanted tumor model in nude mice, and were superior to irinotecan and nktr-102.

Example 16 Inhibitory Effect in a Human Breast Cancer MDA-MB-231 Xenograft Model in Nude Mice Test articles: irinotecan, nktr-102, and 12 compounds of the present disclosure.

Experimental animals: Female BALB/c nude mice. 150 animals were inoculated, and 90 animals were used for the experiment. The animals were 6 to 8 week old and had a body weight of 20 g to 22 g f 20% of the average body weight. The animal source was Shanghai Xipuer-Bikai Experimental Animal Co., Ltd. (BK), license number: SCXK (Shanghai) 2008-0016. All experimental animals were housed in an SPF-level laboratory. Experimenters were responsible for daily care and experimental research. Each mice cage had an identification card with information such as the experimental number, experimental group, name(s) of the experimenter(s), and the strain and sex of mice. The mice were marked with earrings.

Random grouping: After the tumor volumes reached 150 mm$^3$ to 200 mm$^3$, the animals were divided into 15 groups with 6 mice in each group using randomized block method, so as to ensure that the tumor volumes and the body weights of the mice were uniform between each group. The difference between the mean value of the tumor volumes in each group and the mean value of the tumor volumes of all experimental animals was no more than +10%.

Feeding conditions: living condition: IVC system, 6 animals per cage; temperature: 20° C. to 26° C.; humidity: 40% f 70%; illumination: 12 hours light/dark cycle. Irradiated feed for rat and mice was purchased from Beijing Keao Xieli Feed Co., Ltd. The animals had free access to food. The drinking water was the city tap water, which was used for drinking after being filtered and autoclaved. The beddings were corn cobs (Shanghai Maoshengyan Biologic Science & Technology Co., Ltd.) which were used after being autoclaved. The beddings were changed twice a week. The mice were given at least one week of acclimation period for the environment before the experiment.

Other chemical reagents and materials: Human breast cancer MDA-MB-231 cells were purchased from Shanghai Institute of Biochemistry and Cell Biology of Chinese Academy of Sciences.

A human breast cancer MDA-MB-231 subcutaneous transplanted tumor model in nude mice was established, and each animal was inoculated with $1\times10^6$ cells. The volumes of administration were all 10 mL·kg$^{-1}$. The equivalent effective doses of irinotecan were all 40 mg·kg$^{-1}$. Group 1 was a solvent control group, and physiological saline was administered by intravenous injection via tail once every 4 days for a total of 3 times (Q4D×3). Groups 2 to 15 were respectively given the following test samples by intravenous injection via tail once every 4 days, Q4D×3: irinotecan, nktr-102, Compound a, Compound A, Compound b, Compound B, Compound c, Compound C, Compound d, Compound D, Compound e, Compound E, Compound f, and Compound F.

The formulation of the test articles was as shown in Example 15. The volume required for a single administration was 3 mL.

Experimental methods: MDA-MB-231 cells were cultured in DMEM containing 10% fetal bovine serum FBS (GIBCO, USA). The cells were placed in a 37° C. incubator containing 5% $CO_2$ for cultivation. A subcutaneous tumor xenograft model in nude mice was established by cell inoculation method: tumor cells in logarithmic phase of growth were collected, counted and then resuspended in 1×PBS, and the concentration of the cell suspension was adjusted to $1\times10^7$ cells/mL. 1 mL syringes (4 gauge needle) were used to inoculate the tumor cells to the right back of the nude mice subcutaneously, $1\times10^6$ cells/0.1 mL/mice. When the tumor volumes reached 100 mm$^3$ to 200 mm$^3$, the animals were subjected to random grouping according to randomized block method and divided into 15 groups, so that the difference of the tumor volumes between each group was less than 10% of the mean value. There were 6 animals in each group. Day 1 was the day when the animals were grouped, and the animals were administered on the same day when being grouped. The experimental period lasted for 3 weeks, and the body weights and the tumor sizes of the animals were measured twice a week during the experiment. The clinical symptoms were observed and recorded daily. On the last day of the experiment, the animals were sacrificed, the body weights were weighed, and the tumors were excised, weighed and recorded by photographing. The results were as shown in Table 2.

TABLE 2

Relative tumor proliferation rate (% T/C)

| Group | Sample | Number of animals | Relative tumor volume (RTV) | Relative tumor proliferation rate (% T/C) |
| --- | --- | --- | --- | --- |
| 1 | blank solvent | 6 | 12.78 | — |
| 2 | irinotecan | 6 | 6.25 | 45.23% |
| 3 | nktr-102 | 6 | 4.63 | 33.42% |
| 4 | Compound a | 6 | 1.25* | 9.32%# |
| 5 | Compound A | 6 | 1.26* | 9.39%# |
| 6 | Compound b | 6 | 1.72* | 12.82%# |
| 7 | Compound B | 6 | 1.70* | 12.67%# |
| 8 | Compound c | 6 | 1.56* | 11.63%# |
| 9 | Compound C | 6 | 1.64* | 12.22%# |
| 10 | Compound d | 6 | 1.87* | 13.94%# |
| 11 | Compound D | 6 | 1.90* | 14.16%# |
| 12 | Compound e | 6 | 1.78* | 13.27%# |
| 13 | Compound E | 6 | 1.69* | 12.60%# |
| 14 | Compound f | 6 | 1.88* | 14.02%# |
| 15 | Compound F | 6 | 1.93* | 14.39%# |

*$P < 0.05$, as compared with the RTV of the blank solvent group, irinotecan group and nktr-102 group.
$P < 0.05$, as compared with % T/C of the blank solvent group, irinotecan group and nktr-102 group.

The experimental results showed that the compounds of the present disclosure had good inhibitory effects on human breast cancer MDA-MB-231 transplanted tumor in nude mice, and were superior to irinotecan and nktr-102.

Example 17 Inhibitory Effect in a Human Pancreatic Cancer MIA Paca-2 Xenograft Model in Nude Mice Test articles: irinotecan, nktr-102, and 12 compounds of the present disclosure.

Experimental animals: Female BALB/c nude mice. 150 animals were inoculated, and 90 animals were used for the experiment. The animals were 6 to 8 week old and had a body weight of 20 g to 22 g±20% of the average body weight. The animal source was Shanghai Xipuer-Bikai Experimental Animal Co., Ltd. (BK), license number: SCXK (Shanghai) 2008-0016. All experimental animals were housed in an SPF-level laboratory. Experimenters were responsible for daily care and experimental research. Each mice cage had an identification card with information such as the experimental number, experimental group, name(s) of the experimenter(s), and the strain and sex of mice. The mice were marked with earrings. After the tumor volumes reached 150 mm$^3$ to 200 mm$^3$, the animals were divided into 15 groups with 6 mice in each group using randomized block method, so as to ensure that the tumor volumes and the body weights of the mice were uniform between each group. The difference between the mean value of the tumor volumes in each group and the mean value of the tumor volumes of all experimental animals was no more than ±10%.

Feeding conditions: the living condition was an IVC system, 6 animals per cage; temperature: 20° C. to 26° C.; humidity: 40%±70%; illumination: 12 hours light/dark cycle. Irradiated feed for rat and mice was purchased from Beijing Keao Xieli Feed Co., Ltd. The animals had free access to food. The drinking water was the city tap water which was used for drinking after being filtered and autoclaved. The beddings were corn cobs (Shanghai Maoshengyan Biologic Science & Technology Co., Ltd.) which were used after being autoclaved. The beddings were changed twice a week. The mice were given at least one week of acclimation period for the environment before the experiment.

Other chemical reagents and materials: Human pancreatic cancer MIA Paca-2 cells were purchased from Shanghai Institute of Biochemistry and Cell Biology of Chinese Academy of Sciences.

A human pancreatic cancer MIA Paca-2 subcutaneous transplanted tumor model in nude mice was established, and each animal was inoculated with $3\times10^6$ cells. The volumes of administration were all 10 mL·kg$^{-1}$. The equivalent effective doses of irinotecan were all 40 mg·kg$^{-1}$. Group 1 was a solvent control group, and physiological saline was administered by intravenous injection via tail once every 4 days for a total of 3 times (Q4D×3). Groups 2 to 15 were respectively given the following test samples by intravenous injection via tail once every 4 days, Q4D×3: irinotecan, nktr-102, Compound a, Compound A, Compound b, Compound B, Compound c, Compound C, Compound d, Compound D, Compound e, Compound E, Compound f, and Compound F.

The formulation of the test articles was as shown in Example 15. The volume required for a single administration was 3 mL.

Experimental methods: MIA Paca-2 cells were cultured in DMEM containing 10% fetal bovine serum FBS (GIBCO, USA) and 2.5% HS. The cells were placed in a 37° C. incubator containing 5% $CO_2$ for cultivation.

A subcutaneous tumor xenograft model in nude mice was established by cell inoculation method: tumor cells in logarithmic phase of growth were collected, counted and then resuspended in 1×PBS, and the concentration of the cell suspension was adjusted to $3\times10^7$ cells/mL. 1 mL syringes (4 gauge needle) were used to inoculate the tumor cells to the right back of the nude mice subcutaneously, $3\times10^6$ cells/0.1 mL/mice.

When the tumor volumes reached 100 $mm^3$ to 200 $mm^3$, the animals were subjected to random grouping according to randomized block method and divided into 15 groups, so that the difference of the tumor volumes between each group was less than 10% of the mean value. There were 6 animals in each group, Day 1 was the day when the animals were grouped, and the animals were administered on the same day when being grouped.

The experimental period lasted for 3 weeks, and the body weights and the tumor sizes of the animals were measured twice a week during the experiment. The clinical symptoms were observed and recorded daily. On the last day of the experiment, the animals were sacrificed, the body weights were weighed, and the tumors were excised, weighed and recorded by photographing. The results were as shown in Table 3.

TABLE 3

Relative tumor proliferation rate (% T/C)

| Group | Sample | Number of animals | Relative tumor volume (RTV) | Relative tumor proliferation rate (% T/C) |
|---|---|---|---|---|
| 1 | blank solvent | 6 | 11.82 | — |
| 2 | irinotecan | 6 | 8.01 | 61.08% |
| 3 | nktr-102 | 6 | 5.37 | 37.15% |
| 4 | Compound a | 6 | 2.38* | 13.02%[#] |
| 5 | Compound A | 6 | 2.45* | 13.41%[#] |
| 6 | Compound b | 6 | 2.90* | 15.86%[#] |
| 7 | Compound B | 6 | 2.87* | 15.70%[#] |
| 8 | Compound c | 6 | 2.65* | 13.71%[#] |
| 9 | Compound C | 6 | 2.66* | 13.76%[#] |
| 10 | Compound d | 6 | 3.12* | 16.06%[#] |
| 11 | Compound D | 6 | 3.07* | 15.80%[#] |
| 12 | Compound e | 6 | 2.78* | 14.31%[#] |
| 13 | Compound E | 6 | 2.84* | 14.62%[#] |
| 14 | Compound f | 6 | 2.69* | 14.70%[#] |
| 15 | Compound F | 6 | 2.71* | 14.81%[#] |

*$P < 0.05$, as compared with the RTV of the blank solvent group, irinotecan group and nktr-102 group.
[#]$P < 0.05$, as compared with % T/C of the blank solvent group, irinotecan group and nktr-102 group.

The experimental results showed that the compounds of the present disclosure had good inhibitory effects on the human pancreatic cancer MIA Paca-2 transplanted tumor in nude mice, and were superior to irinotecan and nktr-102.

Example 18 Inhibitory Effect on In Vivo Tumor Growth in a Human Gastric Cancer NCI-N87 Cell Strain Transplanted Tumor Model in Nude Mice Test articles: irinotecan, nktr-102, and 12 compounds of the present disclosure.

Reagents: RPMI-1640 liquid culture medium, fetal bovine serum (FBS), trypsin, penicillin-streptomycin, and physiological saline.

Experimental animals: Female BALB/c nude mice (number of animals: 150, weeks of age: 6 to 8 weeks) were purchased from Beijing Vital River Laboratory Animal Technology Co., Ltd., and housed in an SPF animal room in Suzhou Shengsu New Drug Development Co., Ltd. The temperature was 20° C. to 25° C., the relative humidity was 40% to 70%, and the light and dark were respectively 12 hours. The animals had free access to water and food. After about one week of normal feeding, upon a veterinary inspection, mice with good physical signs and conditions could be selected for this experiment. A marking pen was used to mark the base of the tails of the animals before the grouping, and each animal was marked by ear clipping after the grouping.

Transplantable tumor cell strain: Human gastric cancer cell NCI-N87, derived from Cell Bank of Committee on Type Culture Collection of Chinese Academy of Science (CAS, stored frozen in liquid nitrogen in the laboratory).

Experimental Methods

Culture of NCI-N87 cells: Under a culture condition of 5% $CO_2$ and 37° C., NCI-N87 cells were subjected to conventional cell cultivation in an RPMI-1640 liquid culture medium containing 10% fetal bovine serum, digested with 0.25% trypsin, and passaged. According to the condition of cell growth, the cells were passaged once or twice every week, and were passaged in a ratio of 1:2 to 1:6.

Preparation of the animal model: NCI-N87 cells in logarithmic phase of growth were collected. The cells were resuspended in an RPMI-1640 culture medium free of serum after being counted, and the concentration of the cells was adjusted to $5\times10^7$ cells/mL. The cells were charged into a 50 mL centrifuge tube after being pipetted with a pipettor to make them evenly dispersed, and the centrifuge tube was placed in an ice box. Cell suspension was aspirated with a 1 mL syringe, and injected subcutaneously to the anterior right armpit of the nude mice. Each animal was inoculated with 100 μL ($5\times10^6$ cells/animal), and an NCI-N87 transplanted tumor model in nude mice was established. Animal status and the condition of tumor growth were observed regularly after inoculation, an electronic vernier caliper was used to measure the tumor diameters, the data was directly input to an Excel spreadsheet, and the tumor volumes were calculated. When the tumor volumes reached 100 $mm^3$ to 300 $mm^3$, 90 animals with good health condition and similar tumor volumes were selected and divided into 15 groups (n=6) using randomized block method. The tumor diameters were measured twice a week after the initiation of the experiment, the tumor volumes were calculated, and the body weights of the animals were weighed and recorded at the same time.

The formulation of the test articles were as shown in Example 15. The volume required for a single administration was 3 mL.

Grouping of animals and administration: The first administration was initiated on the day of grouping, the experiment was ended after 21 days, and the volumes of administration were all 10 mL·kg$^{-1}$. Group 1 was a solvent control group, and was given blank solvent by intravenous injection via tail once every 4 days for a total of 3 times (Q4D×3). Groups 2 to 15 were respectively given the following test samples by intravenous injection via tail: irinotecan, nktr-102, Compound a, Compound A, Compound b, Compound B, Compound c, Compound C, Compound d, Compound D, Compound e, Compound E, Compound f, and Compound F; and the dosages of administration were all 40 mg·kg$^{-1}$ (calculated in terms of the content of irinotecan), Q4D×3.

After the experiment was ended, the animals were euthanized (CO$_2$) after the body weights were weighed and the tumor diameters were measured. The tumor tissues were excised and weighed. The results were as shown in Table 4.

TABLE 4

Relative tumor proliferation rate (% T/C)

| Group | Sample | Number of animals | Relative tumor volume (RTV, mm$^3$) | Average relative tumor proliferation rate (% T/C) |
|---|---|---|---|---|
| 1 | blank solvent | 6 | 3.01 | — |
| 2 | irinotecan | 6 | 8.02 | 65.15% |
| 3 | nktr-102 | 6 | 6.14 | 50.91% |
| 4 | Compound a | 6 | 2.80* | 23.27%# |
| 5 | Compound A | 6 | 2.87* | 23.86%# |
| 6 | Compound b | 6 | 3.30* | 27.43%# |
| 7 | Compound B | 6 | 3.25* | 27.01%# |
| 8 | Compound c | 6 | 3.44* | 28.61%# |
| 9 | Compound C | 6 | 3.49* | 29.03%# |
| 10 | Compound d | 6 | 3.41* | 28.37%# |
| 11 | Compound D | 6 | 3.27* | 27.21%# |
| 12 | Compound e | 6 | 3.79* | 31.51%# |
| 13 | Compound E | 6 | 3.80* | 31.60%# |
| 14 | Compound f | 6 | 3.59* | 29.87%# |
| 15 | Compound F | 6 | 3.54* | 29.45%# |

*P < 0.05, as compared with the RTV of the blank solvent group, irinotecan group and nktr-102 group.
P < 0.05, as compared with % T/C of the blank solvent group, irinotecan group and nktr-102 group.

The experimental results showed that the compounds of the present disclosure had good inhibitory effects on tumor growth in the human gastric cancer NCI-N87 cell strain transplanted tumor model in nude mice, and were superior to irinotecan and nktr-102.

Example 19 Effect on the Survival Rate of an Orthotopic U87MG Brain Glioma Model in Nude Mice Test articles: irinotecan, nktr-102, and 12 compounds of the present disclosure.

Reagents: RPMI-1640 liquid culture medium, trypsin, penicillin-streptomycin, and physiological saline.

Experimental animals: Female BALB/c nude mice (number of animals: 150, weeks of age: 6 to 8 weeks) were purchased from Beijing Vital River Laboratory Animal Technology Co., Ltd., and housed in an SPF animal room. The temperature was 20° C. to 25° C., the relative humidity was 40% to 70%, and the light and dark were respectively 12 hours. The animals had free access to water and food. After about one week of normal feeding, upon a veterinary inspection, mice with good physical signs and conditions could be selected for this experiment. A marking pen was used to mark the base of the tails of the animals before the grouping, and each animal was marked by ear clipping after the grouping.

Transplantable tumor cell strain: Brain glioma cell U87MG, derived from Cell Bank of Committee on Type Culture Collection of Chinese Academy of Science (CAS, stored frozen in liquid nitrogen in the laboratory).

Experimental Methods:

Culture of U87MG cells: Under a culture condition of 5% CO$_2$ and 37° C., U87MG cells were subjected to conventional cell cultivation in an RPMI-1640 liquid culture medium, digested with 0.25% trypsin, and passaged. According to the condition of cell growth, the cells were passaged once or twice every week, and were passaged in a ratio of 1:2 to 1:6.

Preparation of the animal model: U87MG cells in logarithmic phase of growth were collected. The cells were resuspended in an RPMI-1640 culture medium free of serum after being counted, and the concentration of the cells was adjusted to 1×10$^8$ cells/mL. The cells were charged into a 50 mL centrifuge tube after being pipetted with a pipettor to make them evenly dispersed, and the centrifuge tube was placed in an ice box. Cell suspension was aspirated with a 1 mL syringe, 1 μL of human brain glioma cell (U87MG cells) cultured in vitro was inoculated (1×10$^5$ cells/animal) using microinjection method via the guidance of a stereotactic apparatus for animals, the orthotopic U87MG brain glioma model was established, and the animal status was observed periodically after inoculation. On the 12th day after inoculation, 90 animals were selected and divided into 15 groups (n=6) using randomized block method.

Preparation of the dosing formulations: The formulation of the test articles was as shown in Example 15. The volume required for a single administration was 3 mL.

Grouping of animals and administration: The first administration was initiated on the day of grouping, the experiment was ended after 21 days, and the volumes of administration were all 10 mL·kg$^{-1}$. Group 1 was a solvent control group, and was given blank solvent by intravenous injection via tail once every 4 days for a total of 3 times (Q4D×3). Groups 2 to 15 were given irinotecan, nktr-102 and test compounds as test samples by intravenous injection via tail, respectively, and the dosages of administration were all 40 mg·kg$^{-1}$ (calculated in terms of the content of irinotecan), Q4D×3.

Data recording and calculation formula: The survival time of the animals were recorded. The experimental data was subjected to calculation and related statistical treatments using Microsoft Office Excel 2007 Software. t test was adopted for the comparison between two groups. The results were as shown in Table 5.

TABLE 5

Survival time of the animals (day)

| Group | Sample | Number of animals | Survival time | Median survival time |
|---|---|---|---|---|
| 1 | blank solvent | 6 | 16 to 22 | 20 |
| 2 | irinotecan | 6 | 22 to 32 | 27 |
| 3 | nktr-102 | 6 | 25 to 37 | 31 |
| 4 | Compound a | 6 | 34 to 46 | 40* |
| 5 | Compound A | 6 | 34 to 46 | 40* |
| 6 | Compound b | 6 | 34 to 41 | 38* |
| 7 | Compound B | 6 | 34 to 41 | 38* |
| 8 | Compound c | 6 | 34 to 45 | 38* |
| 9 | Compound C | 6 | 34 to 45 | 38* |
| 10 | Compound d | 6 | 30 to 39 | 35* |
| 11 | Compound D | 6 | 30 to 39 | 35* |
| 12 | Compound e | 6 | 33 to 44 | 39* |
| 13 | Compound E | 6 | 33 to 44 | 39* |

TABLE 5-continued

Survival time of the animals (day)

| Group | Sample | Number of animals | Survival time | Median survival time |
|---|---|---|---|---|
| 14 | Compound f | 6 | 30 to 42 | 38* |
| 15 | Compound F | 6 | 30 to 42 | 38* |

*P < 0.05, as compared with the median survival time of the blank solvent group, irinotecan group and nktr-102 group.

The experimental results showed that the compounds of the present disclosure had good inhibitory effects on brain glioma, and were superior to irinotecan and nktr-102.

What is claimed is:

1. A multi-branched drug conjugate having the following structural formula (I) or a pharmaceutically acceptable salt thereof:

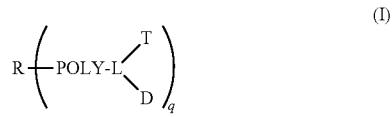

(I)

R is an organic core, POLY is a polymer, L is a multivalent linker, T is a targeting molecule, D is an active agent, and q is any integer between 3 and 8, wherein L is

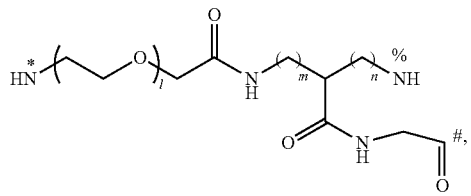

a symbol "*" represents an attachment point of the multivalent linker L and the targeting molecule T, "#" represents an attachment point of the multivalent linker L and the active agent D, and "%" represents an attachment point of the multivalent linker L and POLY, wherein l is any integer between 2 and 20, and m and n are any integer between 0 and 10 respectively;

T is an RGD peptide containing a sequence of "arginine-glycine-aspartic acid", tLyp-1, Lyp-1, RPARPAR, Angiopep2, or GE11;

D is a camptothecin-based drug as represented by formula (II):

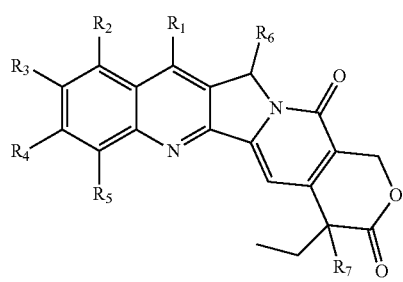

(II)

wherein $R_1$ to $R_5$ are selected from the following groups independently from each other: hydrogen, halogen, acyl, alkyl, substituted alkyl, alkoxy, substituted alkoxy, alkenyl, alkynyl, cycloalkyl, hydroxyl, cyano, nitro, azido, amido, hydrazine, amine group, substituted amine group, hydroxycarbonyl, alkoxycarbonyl, alkoxycarbonyloxy, carbamoyloxy, arylsulfonyloxy, and alkylsulfonyloxy; $R_6$ is H or $OR_8$; $R_8$ is alkyl, alkenyl, cycloalkyl, halogenated alkyl, or hydroxyalkyl; and $R_7$ is hydroxyl.

2. The multi-branched drug conjugate or the pharmaceutically acceptable salt thereof according to claim 1, wherein T is cRGD or iRGD.

3. The multi-branched drug conjugate or the pharmaceutically acceptable salt thereof according to claim 1, wherein POLY is polyethylene glycol.

4. The multi-branched drug conjugate or the pharmaceutically acceptable salt thereof according to claim 3, wherein POLY is

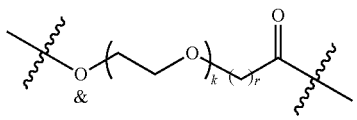

wherein " ⌇ " represents a site for attachment of atoms, an oxygen atom marked with "&" is the atom attached to the organic core "R", k is an integer in a range of 50 to 200, and r is any integer between 1 and 10.

5. The multi-branched drug conjugate or the pharmaceutically acceptable salt thereof according to claim 4, which is as represented by structural formula (III), (IV), or (V):

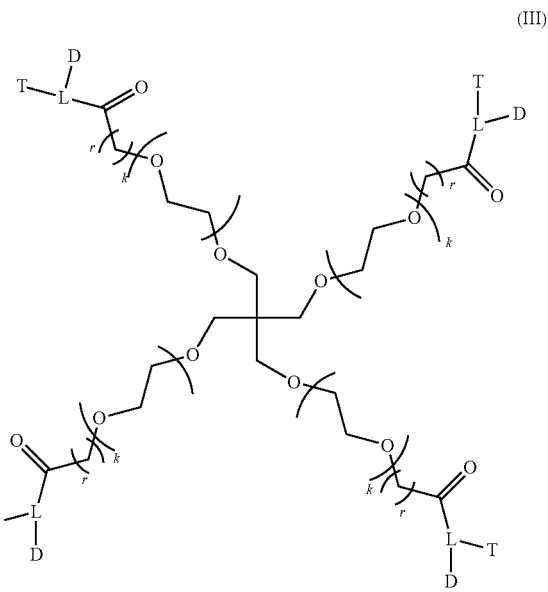

(III)

(IV)

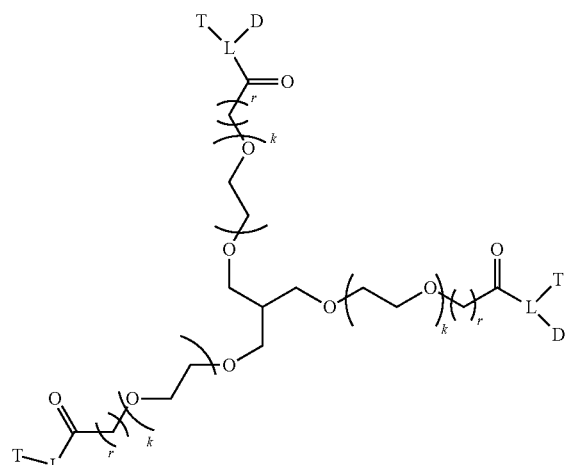

(V)

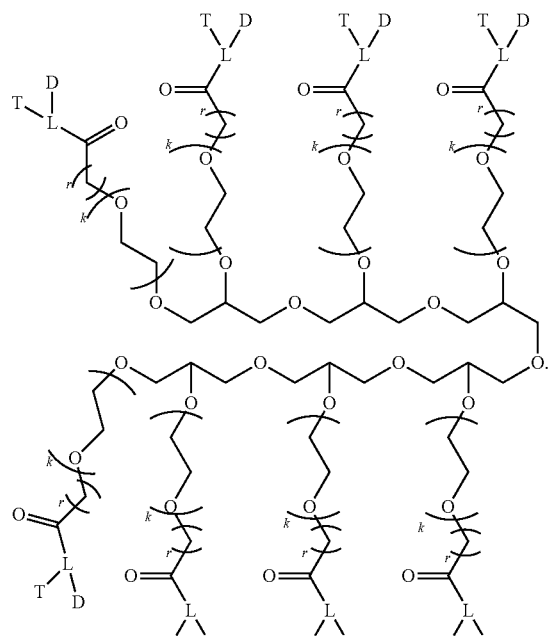

6. The multi-branched drug conjugate or the pharmaceutically acceptable salt thereof according to claim 5, wherein POLY is

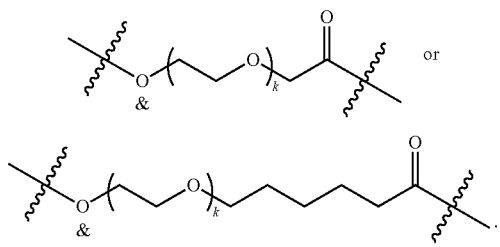

7. The multi-branched drug conjugate or the pharmaceutically acceptable salt thereof according to claim 6, which is

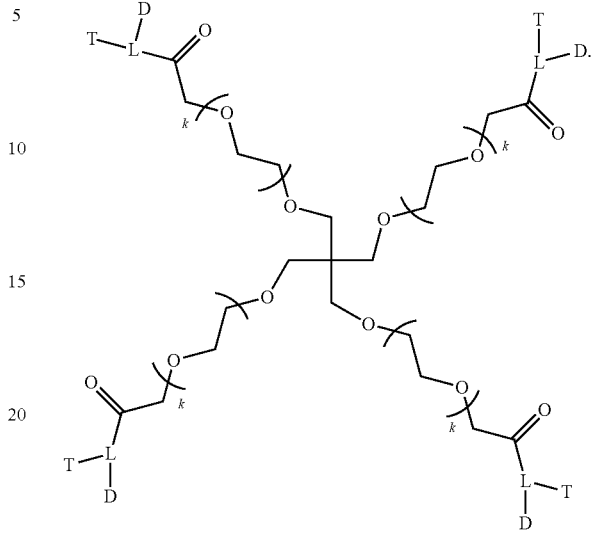

8. The multi-branched drug conjugate or the pharmaceutically acceptable salt thereof according to claim 7, wherein k has an average value of 113.

9. The multi-branched drug conjugate or the pharmaceutically acceptable salt thereof according to claim 8, wherein L is

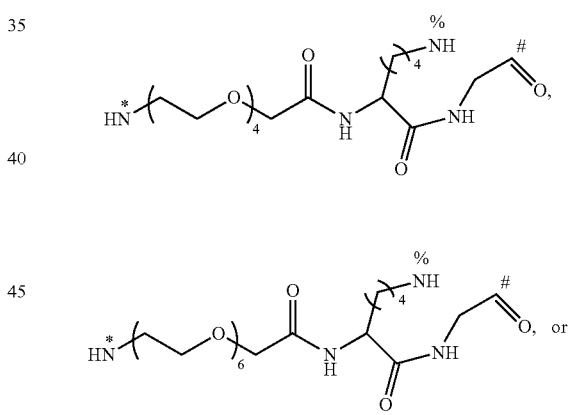

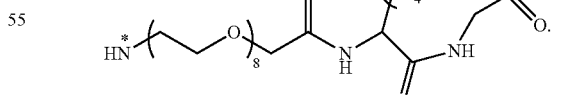

10. The multi-branched drug conjugate or the pharmaceutically acceptable salt thereof according to claim 9, wherein D is irinotecan, SN-38, 10-hydroxycamptothecin, or rubitecan.

11. The multi-branched drug conjugate or the pharmaceutically acceptable salt thereof according to claim 10, which is Compound a
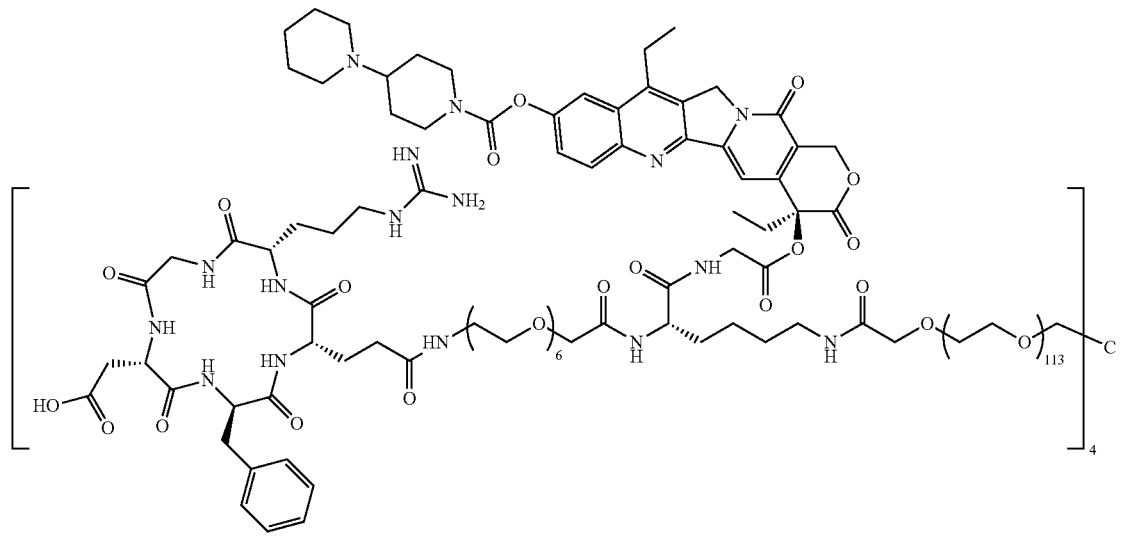
Compound b
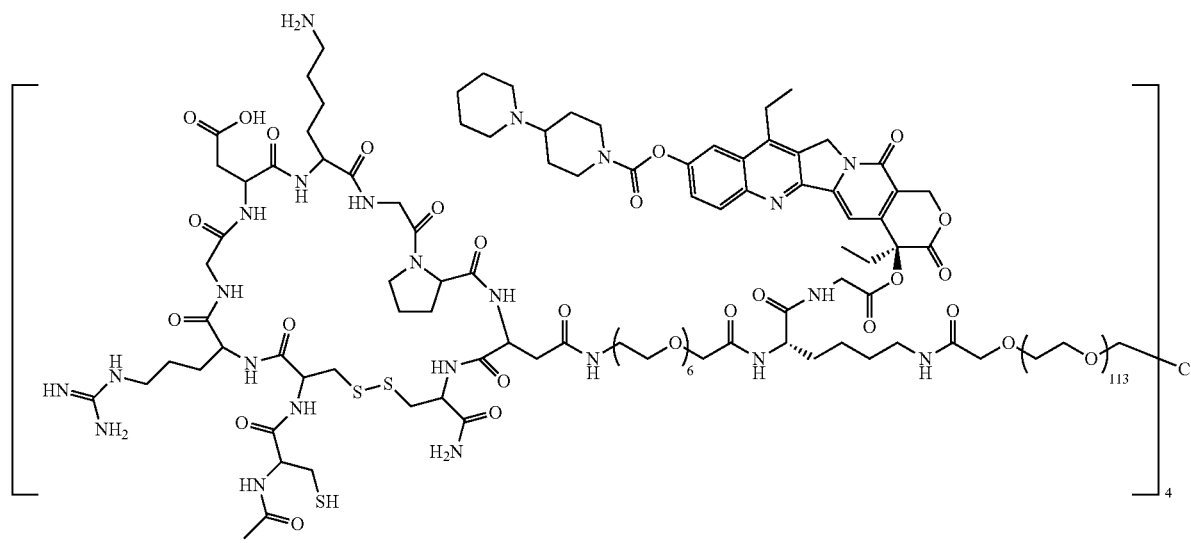
Compound c
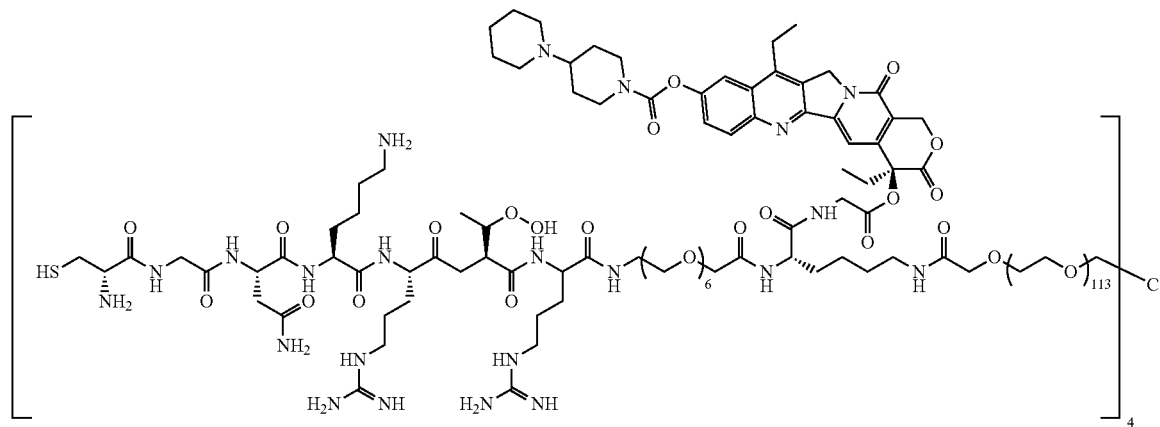

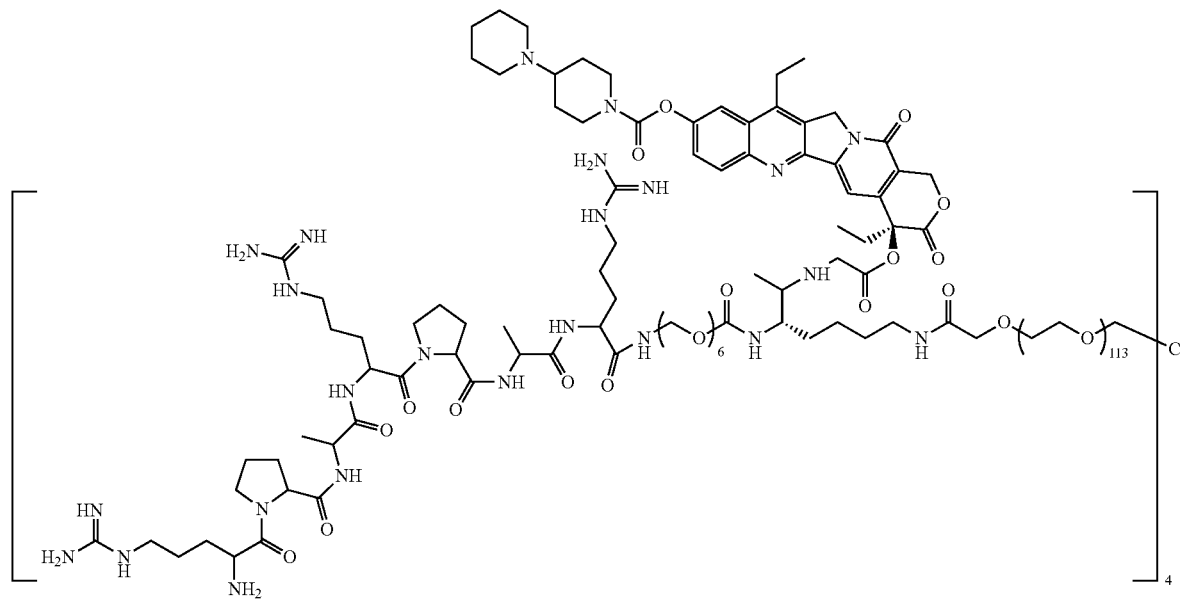
Compound d
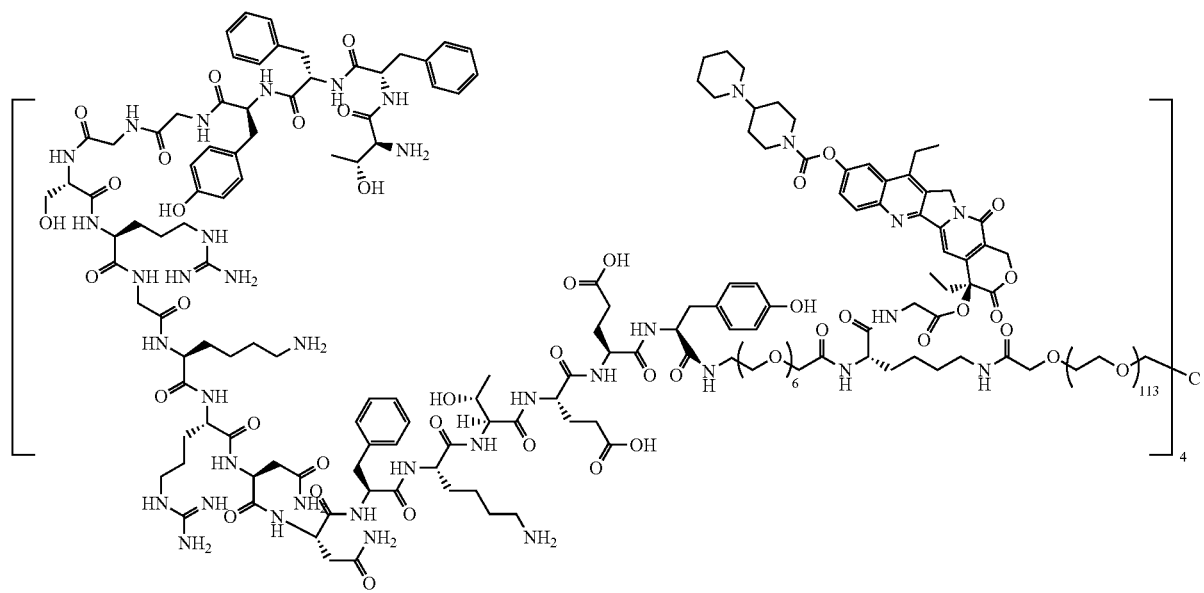
Compound e

Compound f
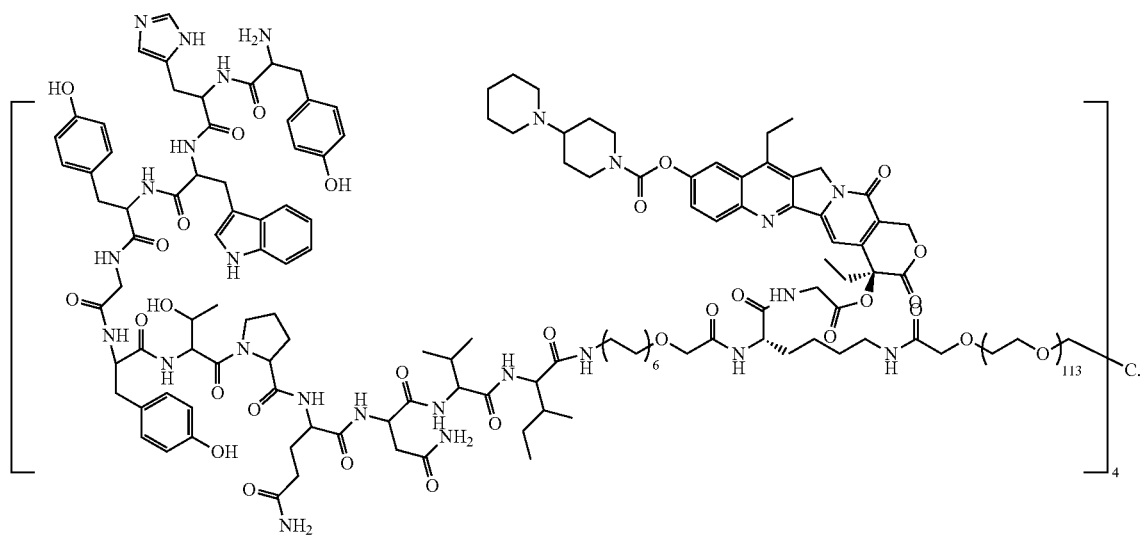
12. The multi-branched drug conjugate or the pharmaceutically acceptable salt thereof according to claim 11, which is
Compound A
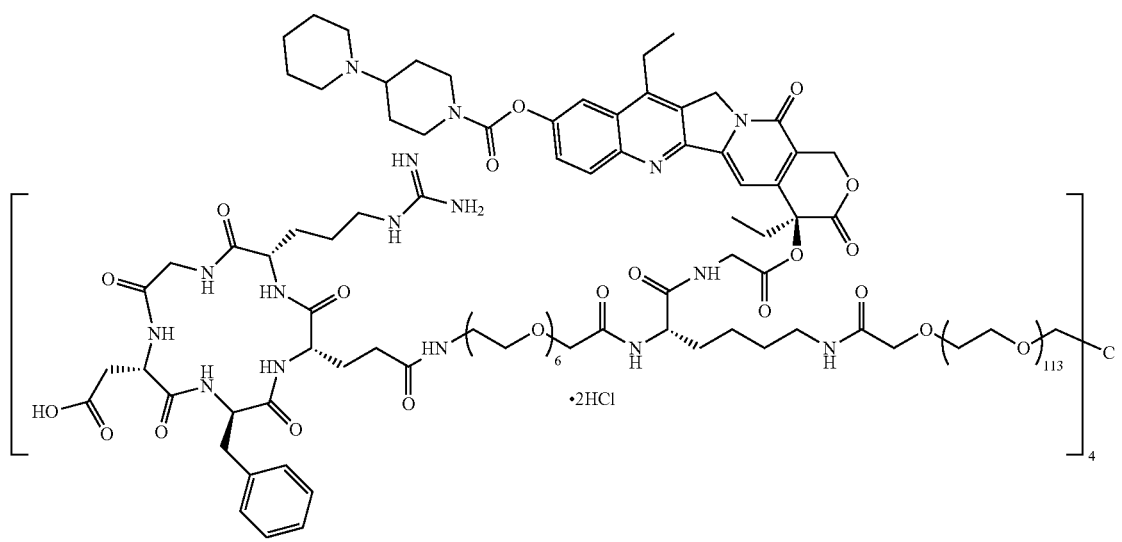

-continued
Compound B
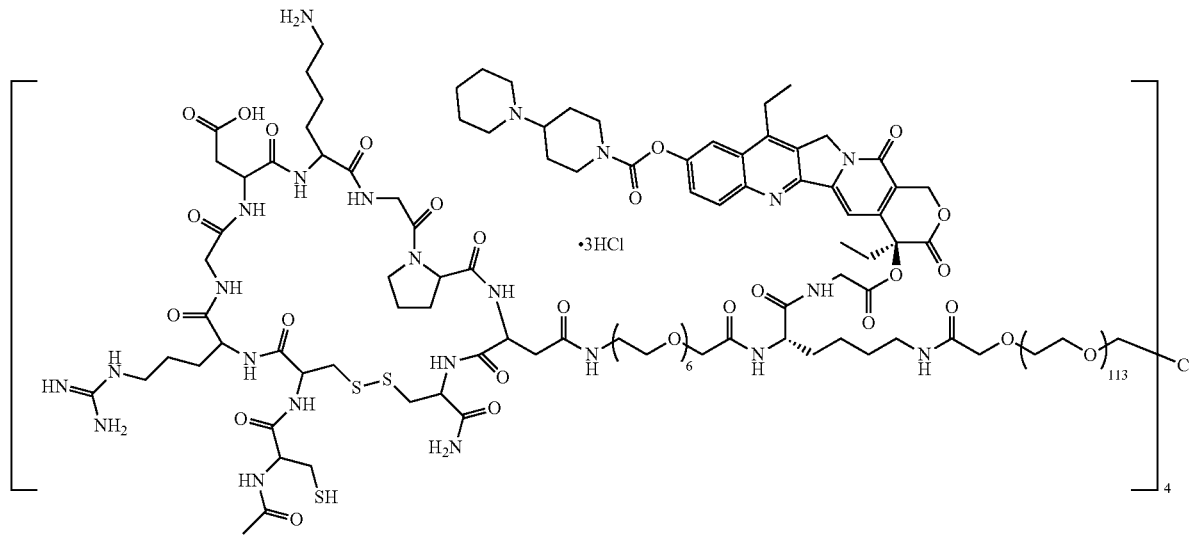
Compound C
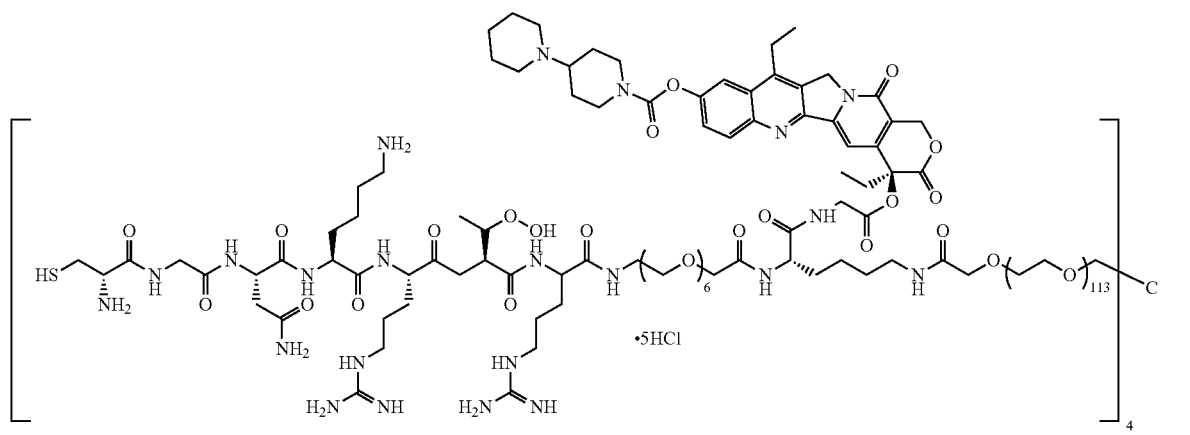
Compound D
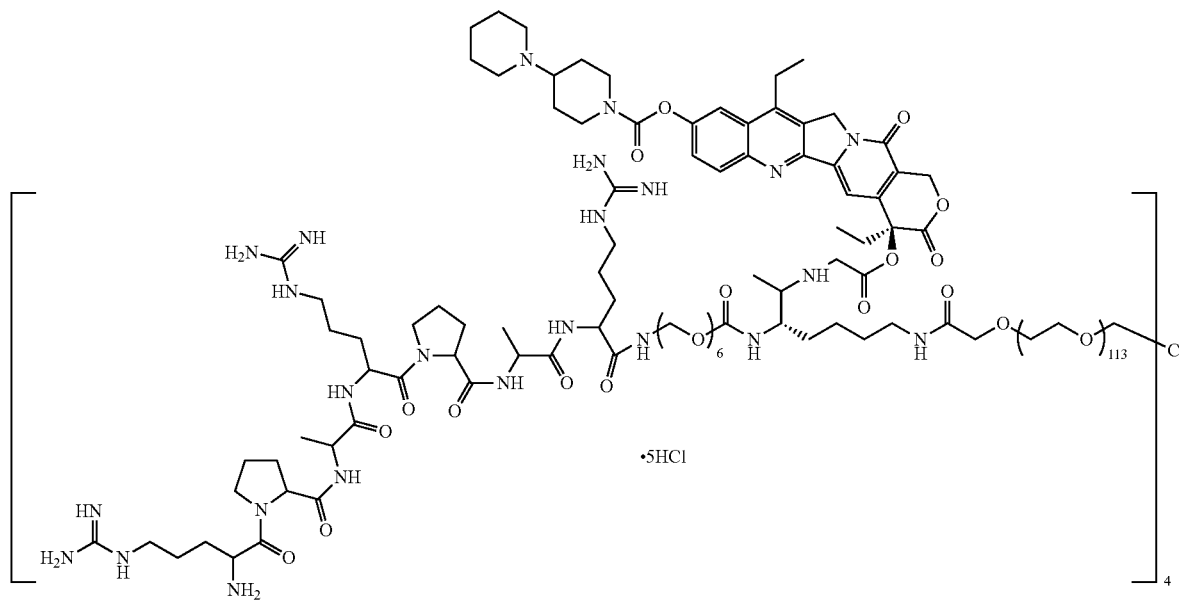

-continued

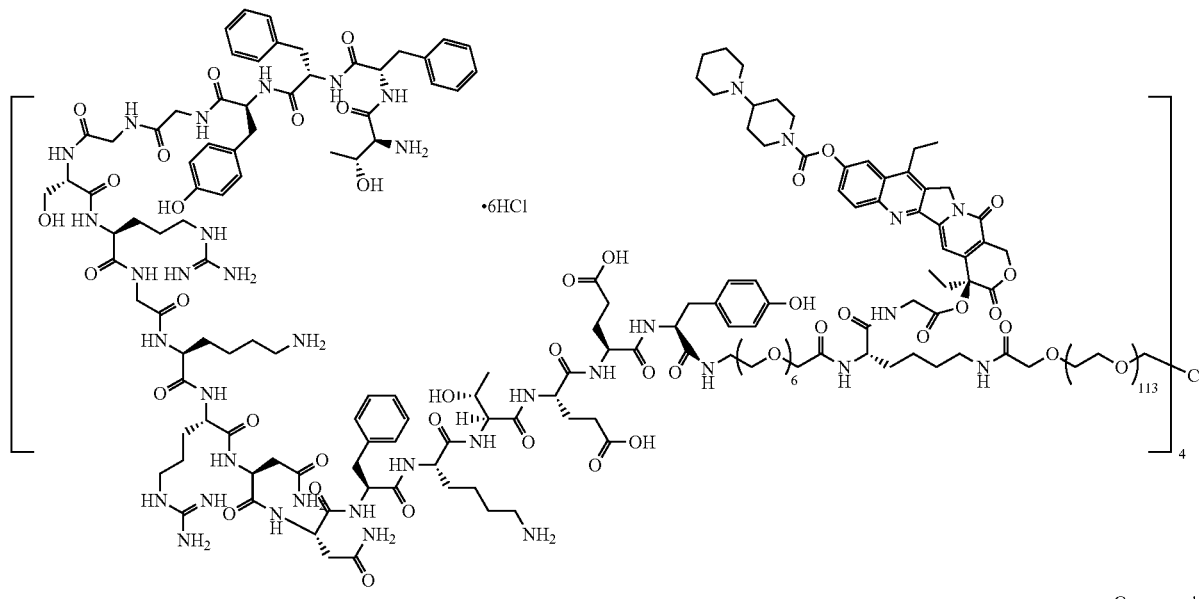

Compound E

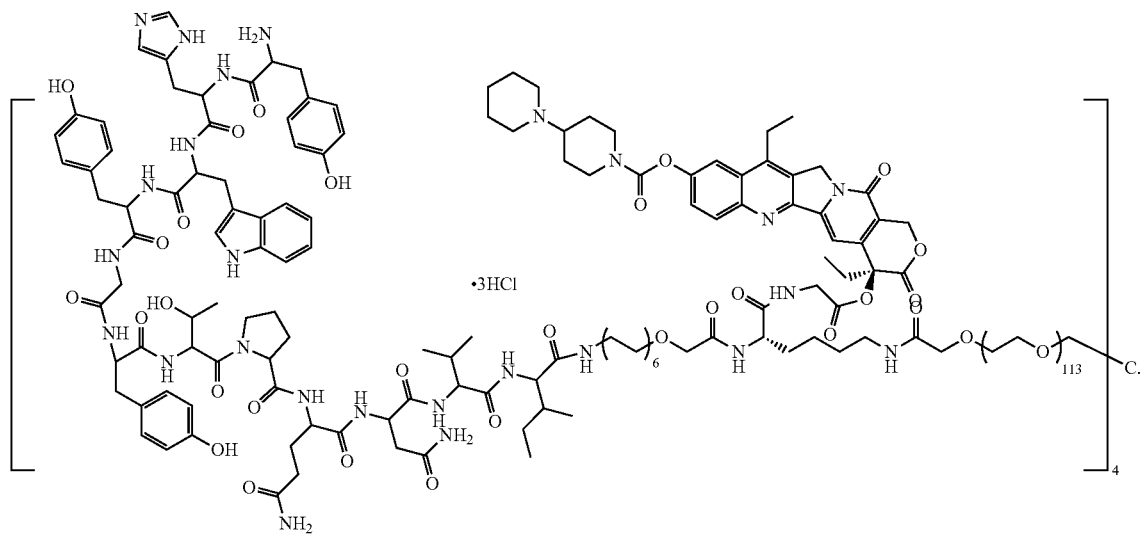

Compound F

13. A pharmaceutical composition, comprising the multi-branched drug conjugate or the pharmaceutically acceptable salt thereof according claim 1, and a pharmaceutically acceptable excipient.

14. A method for treating a cancer selected from the group consisting of colon cancer, lung cancer, breast cancer, ovarian cancer, pancreatic cancer, gastric cancer, brain glioma, and a malignant sarcoma, a cancer and a lymphoma of breast, ovary, colon, kidney, bile duct, lung and brain, comprising administering to a subject in need thereof a therapeutic effective amount of the multi-branched drug conjugate or the pharmaceutically acceptable salt thereof according to claim 1.

15. A method for treating a cancer selected from the group consisting of colon cancer, lung cancer, breast cancer, ovarian cancer, pancreatic cancer, gastric cancer, brain glioma, and a malignant sarcoma, a cancer and a lymphoma of breast, ovary, colon, kidney, bile duct, lung and brain, comprising administering to a subject in need thereof a therapeutic effective amount of the pharmaceutical composition according to claim 13.

16. A pharmaceutical composition, comprising the multi-branched drug conjugate or the pharmaceutically acceptable salt thereof according to claim 5, and a pharmaceutically acceptable excipient.

17. A pharmaceutical composition, comprising the multi-branched drug conjugate or the pharmaceutically acceptable salt thereof according to claim 11, and a pharmaceutically acceptable excipient.

18. A pharmaceutical composition, comprising the multi-branched drug conjugate or the pharmaceutically acceptable salt thereof according to claim 12, and a pharmaceutically acceptable excipient.

* * * * *

UNITED STATES PATENT AND TRADEMARK OFFICE
CERTIFICATE OF CORRECTION

Page 1 of 7

PATENT NO. : 11,191,843 B2
APPLICATION NO. : 16/498765
DATED : December 7, 2021
INVENTOR(S) : Jiandong Yuan et al.

It is certified that error appears in the above-identified patent and that said Letters Patent is hereby corrected as shown below:

On the Title Page

Column 2, item (57), Abstract, Line 9, please delete "l is" and insert therefor -- 1 is --;

In the Claims

Column 101, Line 46, Claim 1, please delete "I is" and insert therefor -- 1 is --;

Columns 105-106, Lines 5-6, Claim 11, please delete

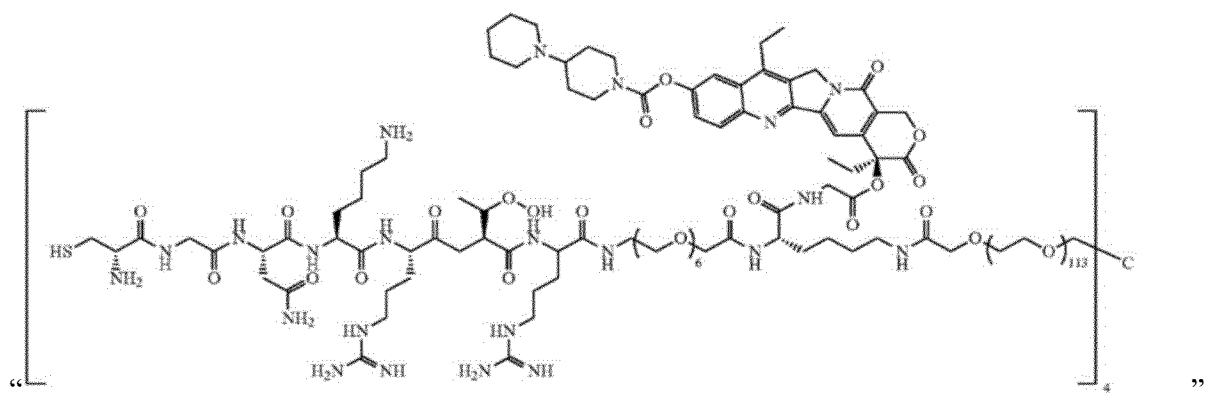

Signed and Sealed this
Third Day of May, 2022

Katherine Kelly Vidal
*Director of the United States Patent and Trademark Office*

CERTIFICATE OF CORRECTION (continued)
U.S. Pat. No. 11,191,843 B2 and insert therefor

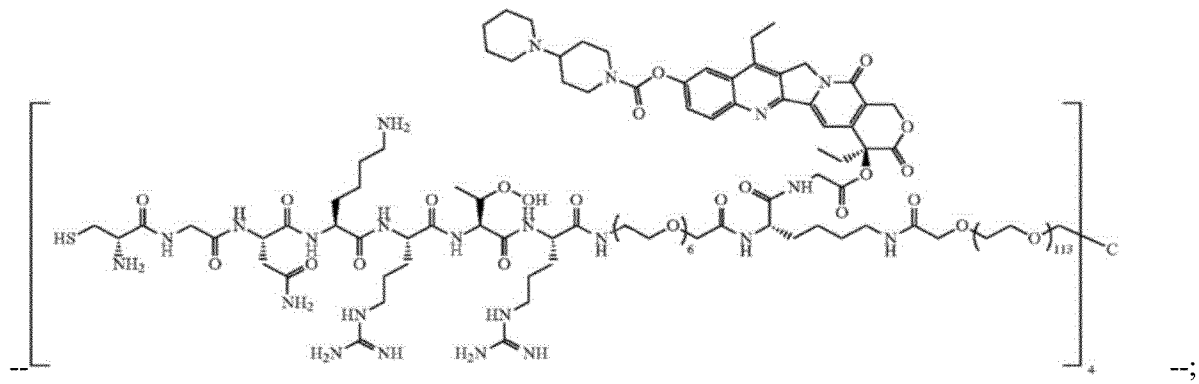

Columns 107-108, Lines 2-3, Claim 11, please delete

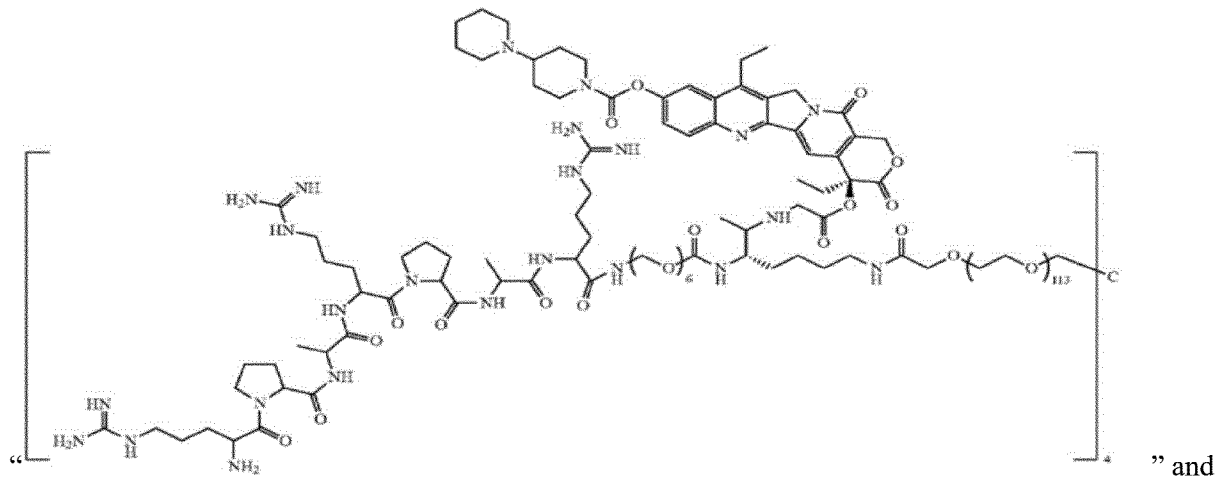

" and insert therefor

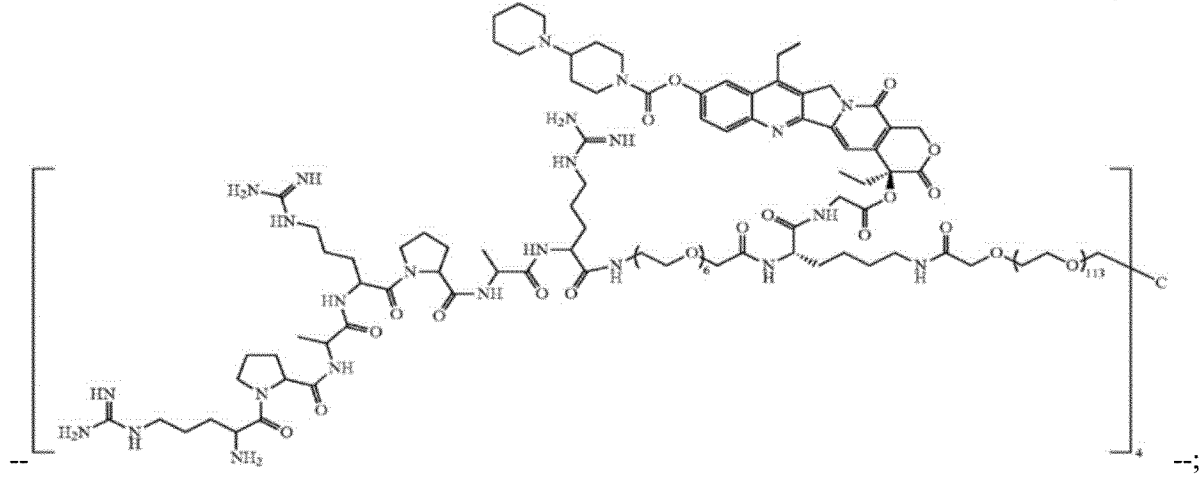

CERTIFICATE OF CORRECTION (continued)
U.S. Pat. No. 11,191,843 B2

Columns 107-108, Lines 4-5, Claim 11, please delete

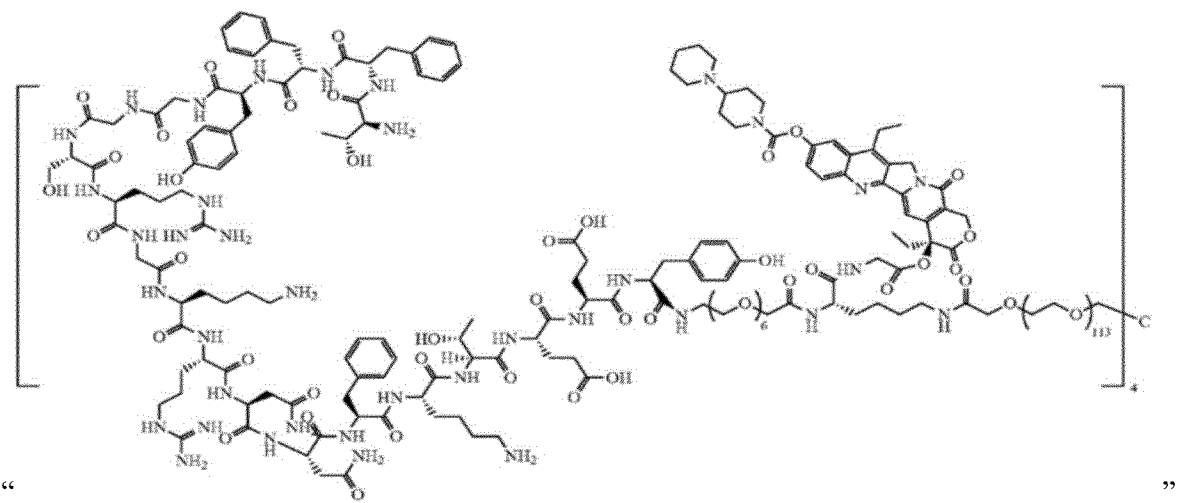

"

"

and insert therefor

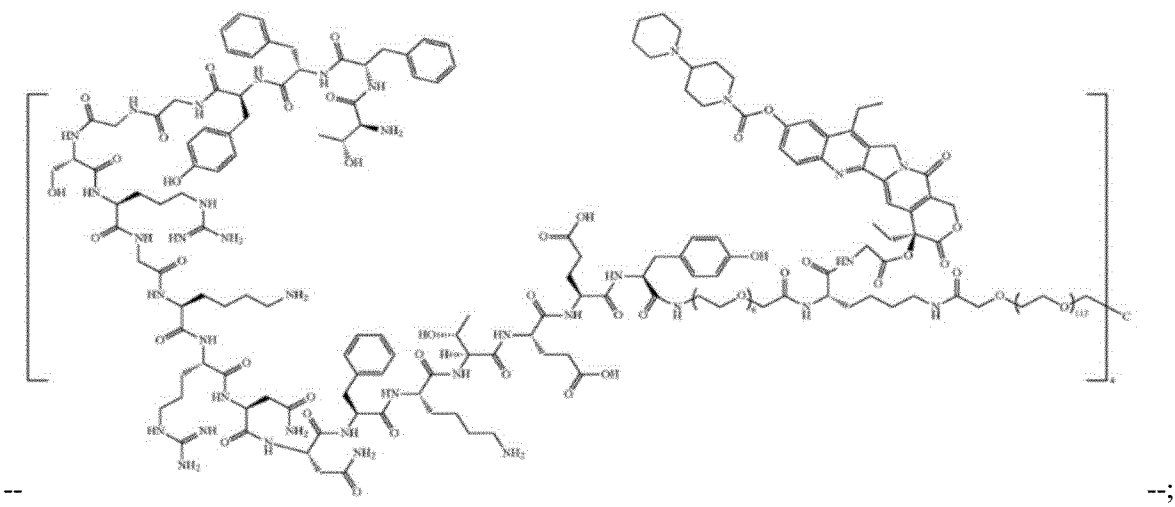

--                                                                                              --;

CERTIFICATE OF CORRECTION (continued)
U.S. Pat. No. 11,191,843 B2

Columns 109-110, Lines 2-3, Claim 11, please delete

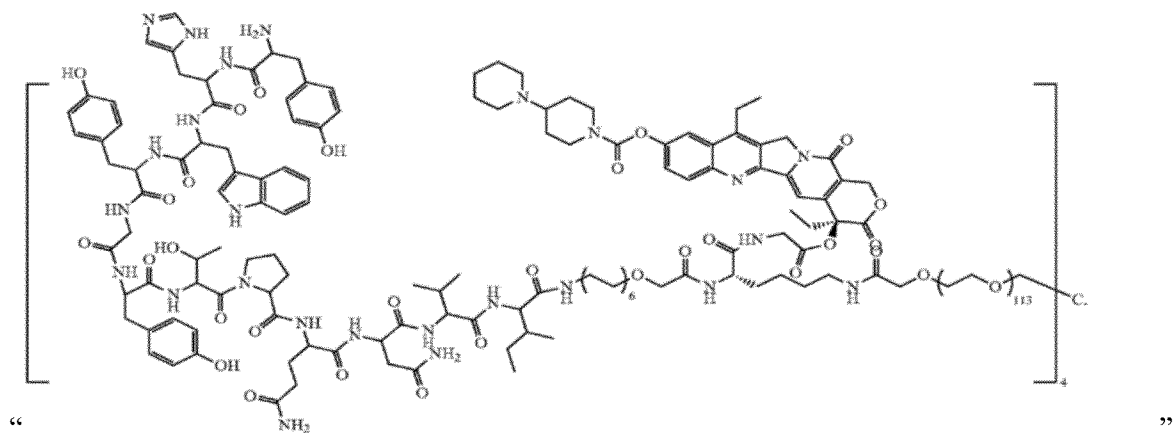

" and insert therefor

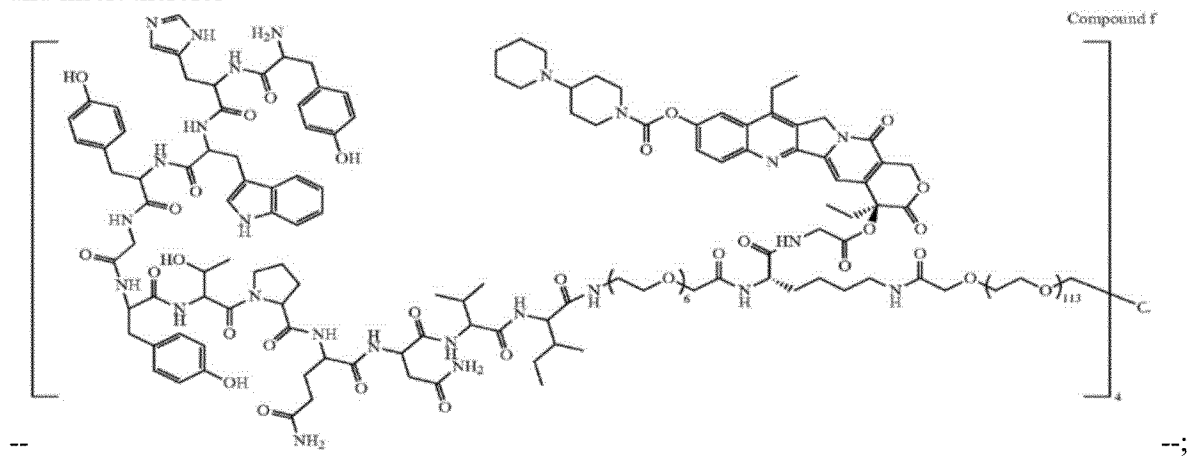

--;

Columns 111-112, Lines 4-5, Claim 12, please delete

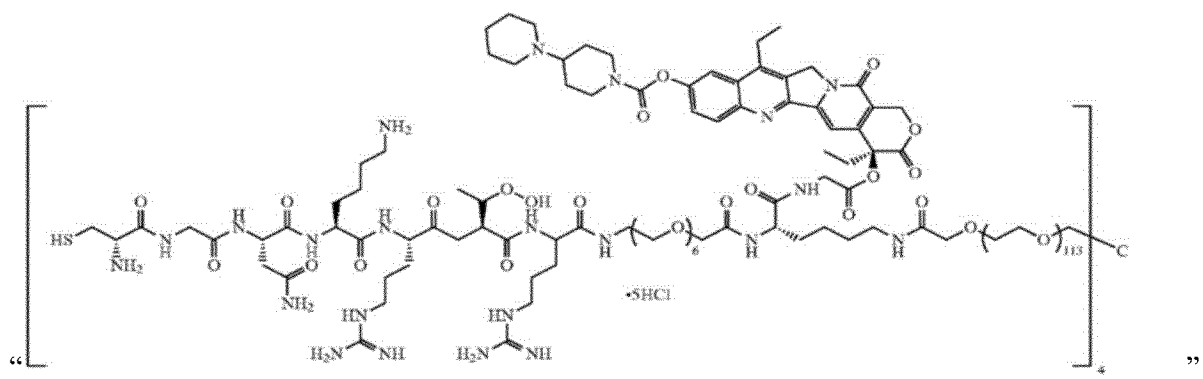

" and insert therefor

CERTIFICATE OF CORRECTION (continued)
U.S. Pat. No. 11,191,843 B2

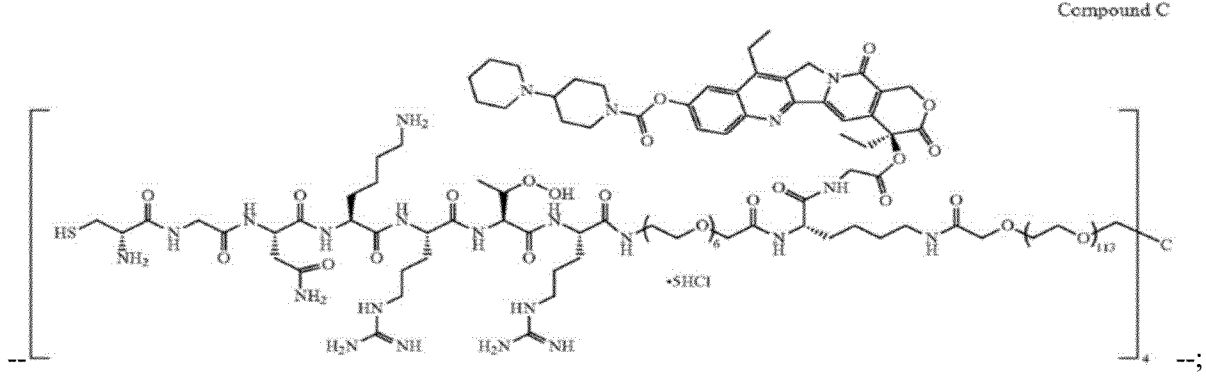

Column 111-112, Lines 6-7, Claim 12, please delete

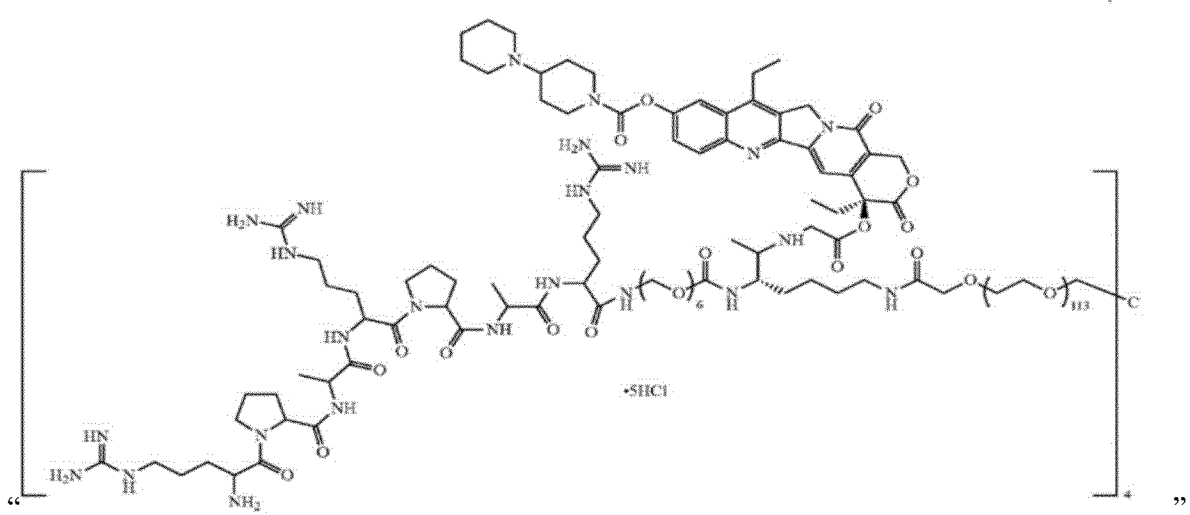

" and insert therefor

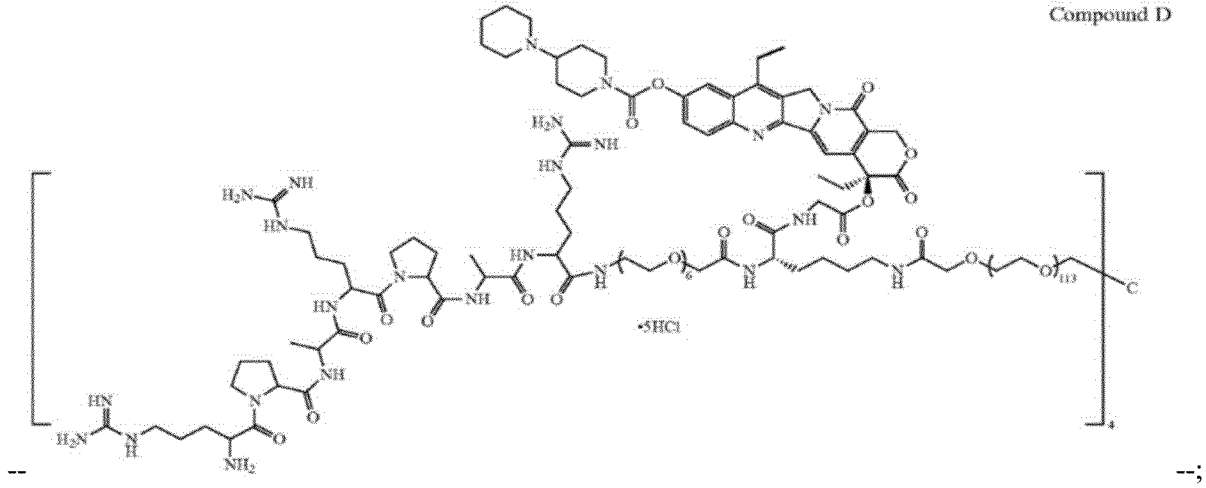

CERTIFICATE OF CORRECTION (continued)
U.S. Pat. No. 11,191,843 B2

Page 6 of 7

Column 113-114, Lines 2-3, Claim 12, please delete

"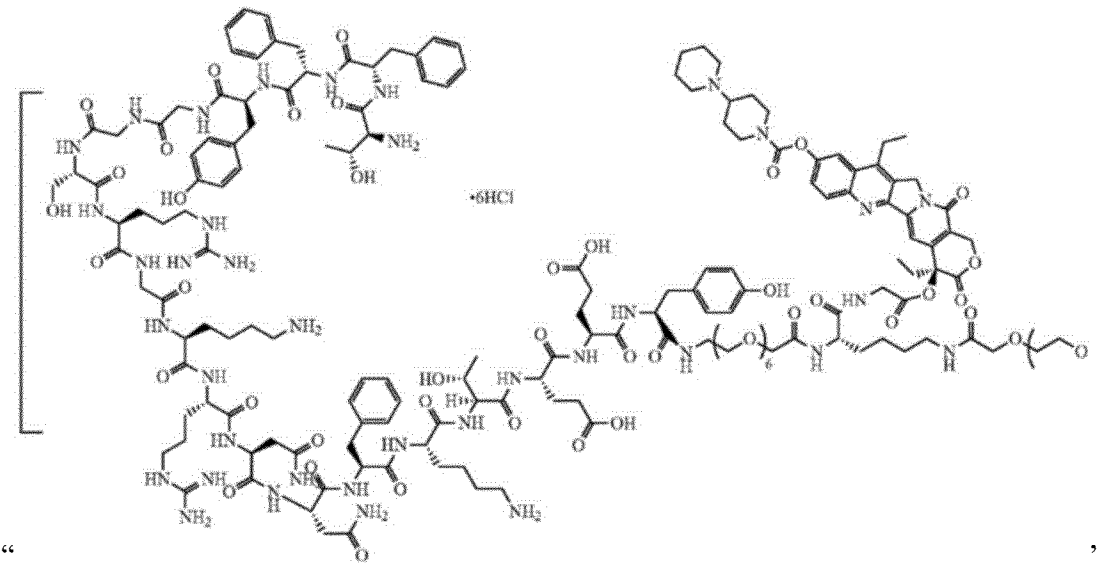" and insert therefor

--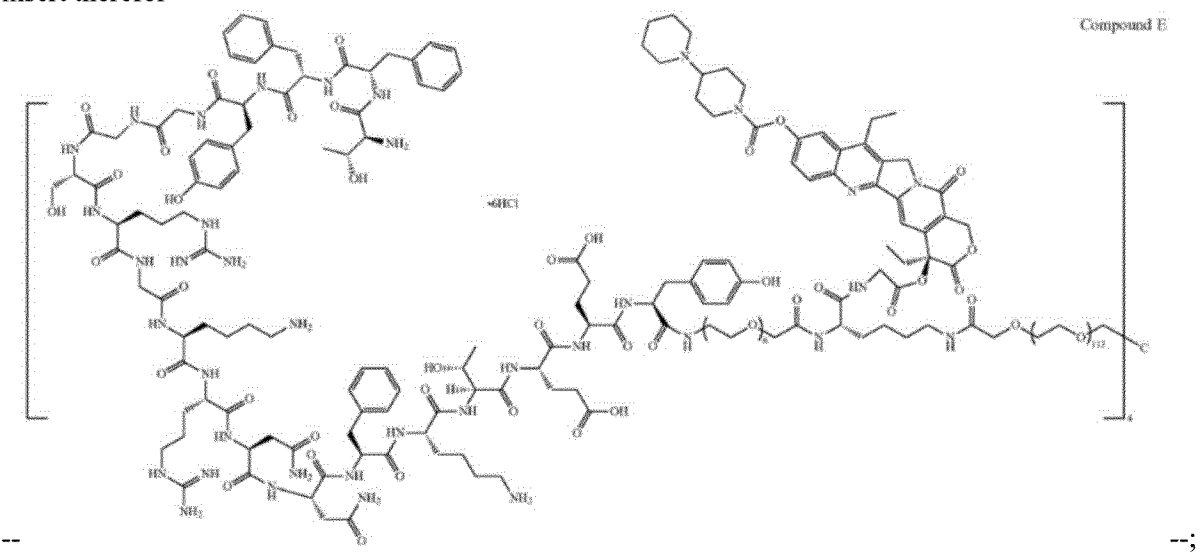--;

Columns 113-114, Lines 4-5, Claim 12, please delete
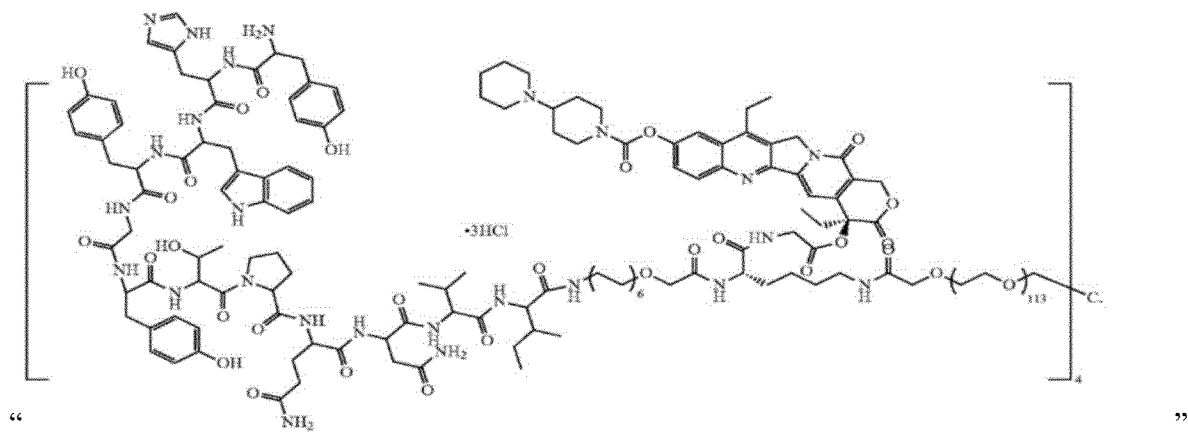
" "
and insert therefor
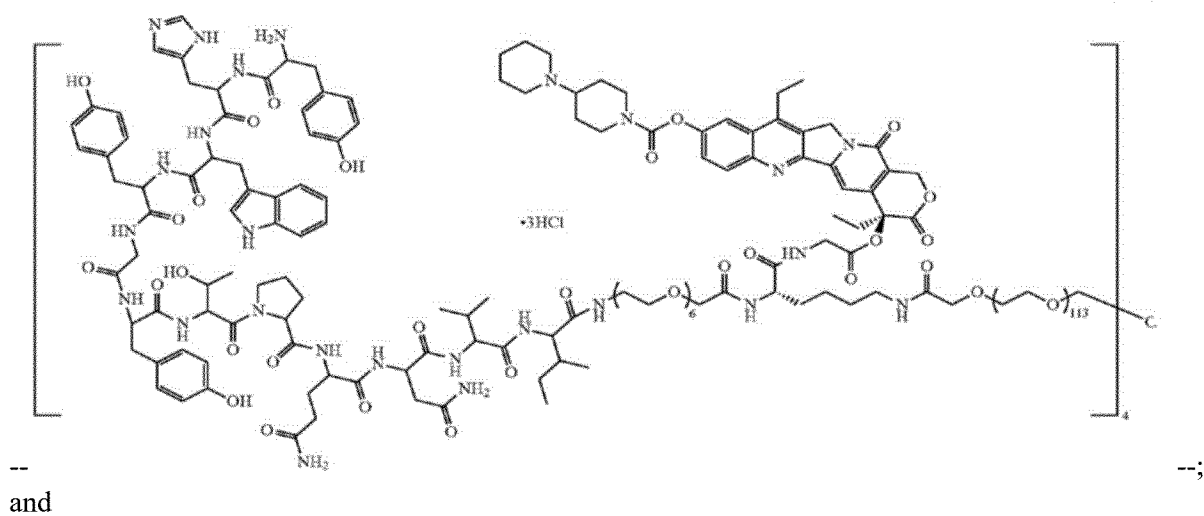
-- --;
and
Column 113, Line 52, Claim 13, after "according" please insert -- to --.